United States Patent
Chan et al.

(10) Patent No.: US 10,905,684 B2
(45) Date of Patent: Feb. 2, 2021

(54) AMINOAMIDE COMPOUNDS

(71) Applicant: BioTheryX, Inc., Chappaqua, NY (US)

(72) Inventors: Kyle W. H. Chan, San Diego, CA (US); Aparajita Hoskote Chourasia, San Diego, CA (US); Paul E. Erdman, San Diego, CA (US); Leah Fung, San Diego, CA (US); Frank Mercurio, Rancho Santa Fe, CA (US); Robert Sullivan, Vista, CA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

(21) Appl. No.: 16/438,185

(22) Filed: Jun. 11, 2019

(65) Prior Publication Data

US 2020/0009120 A1 Jan. 9, 2020

Related U.S. Application Data

(60) Provisional application No. 62/684,541, filed on Jun. 13, 2018, provisional application No. 62/731,596, filed on Sep. 14, 2018.

(51) Int. Cl.

| | | |
|---|---|---|
| *C07D 401/04* | (2006.01) | |
| *C07D 403/04* | (2006.01) | |
| *A61K 31/4439* | (2006.01) | |
| *A61P 35/00* | (2006.01) | |
| *A61K 31/454* | (2006.01) | |
| *A61K 31/4545* | (2006.01) | |
| *A61K 31/5377* | (2006.01) | |
| *A61K 31/55* | (2006.01) | |
| *C07D 413/14* | (2006.01) | |
| *C07D 495/04* | (2006.01) | |

(52) U.S. Cl.
CPC ........ *A61K 31/4439* (2013.01); *A61K 31/454* (2013.01); *A61K 31/4545* (2013.01); *A61K 31/5377* (2013.01); *A61K 31/55* (2013.01); *A61P 35/00* (2018.01); *C07D 401/04* (2013.01); *C07D 403/04* (2013.01); *C07D 413/14* (2013.01); *C07D 495/04* (2013.01)

(58) Field of Classification Search
CPC .......................... C07D 401/04; C07D 403/04
See application file for complete search history.

(56) References Cited

U.S. PATENT DOCUMENTS

2011/0223611 A1* 9/2011 Salamone .............. C07K 16/44
435/7.1
2014/0314752 A1 10/2014 Lopez-Girona et al.

FOREIGN PATENT DOCUMENTS

CN 103396397 11/2013

OTHER PUBLICATIONS

Amit et al., 2002, Axin-mediated CKI phosphorylation of β-catenin at Ser 45: a molecular switch for the Wnt pathway, Genes & Development, 16:1066-1076.
Brito et al., 2005, Polyglycine expansions in eRF3/GSPT1 are associated with gastric cancer susceptibility, Carcinogenesis, 26(12):2046-2049.
Chauvin et al., Aug. 2007, Human eukaryotic release factor 3a depletion causes cell cycle arrest at $G_1$ phase through inhibition of the mTOR pathway, Mol. Cell. Bio., 27(16):5619-5629.
Cheong et al,, 2011, Casein kinase 1: complexity in the family, J. Biochem. Cell Biol., 43:465-469.
Elyada et al., Feb. 17, 2011, CK1α ablation highlights a critical role for p53 in invasiveness control, Nature, 470:409-413.
Hashimoto et al., 2012, Translation termination factor eRF3 is targeted for caspase-mediated proteolytic cleavage and degradation during DNA damage-induced apoptosis, Apoptosis, 17:1287-1299.
Huart et al., Nov. 20, 2009, CK1α plays a central role in mediating MDM2 control of p53 and E2F-1 protein stability, J. Biol. Chem., 284(47):32384-32394.
Ishii et al., Jan. 27, 2017, A novel Rac1-GSPT1 signaling pathway controls astrogliosis following central nervous system injury, J. Biol. Chem., 292(4):1240-1250.
Levine et al., Oct. 2009, The first 30 years of p53: growing ever more complex, Nat. Rev. Cancer, 9(10):749-758.
Li et. al., Jan. 2014, eRF3b, a biomarker for hepatocellular carcinoma, influences cell cycle and phosphoralation status of 4E-BP1, PLOS One, 9(1):e86371.
Liu et al., Sep. 27, 2017, Thalidomide and its analogues: a review of the potential for immunomodulation of fibrosis diseases and opthalmopathy (review); Experimental and Therapeutic Medicine, 14:5251-5257.
Malta-Vacas et al., 2009, Differential expression of GSPT1 $GGC_n$ alleles in cancer, Canc. Geneti. Cytogen., 195:132-142.
Matyskiela et al., Jan. 25, 2018, A cereblon modulator (CC-220) with improved degradation of ikaros and aiolos, Journal of Medicinal Chemistry, 61(2):535-542.
Miri et al., 2012, GGCn polymorphism of eRF3a/GSPT1 gene and breast cancer susceptibility, Med. Oncol., 29:1581-1585.
Schittek et al., 2014 Biological functions of casein kinase 1 isoforms and putative roles in tumorigenesis, Mol. Cancer., 13:231.
Schneider et al., Oct. 13, 2014, Role of casein kinase 1A1 in the biology and targeted therapy of del(5q) MDS, Cancer Cell, 26:509-520.
Stern, Mar. 2010, Prevalence of a history of skin cancer in 2007, Arch Dermatol., 146(3):279-282.
Wright et al., 2007, Newer potential biomarkers in prostate cancer, Rev. Urol., 9(4):207-213.
International Search Report and Written Opinion dated Sep. 24, 2019 in application No. PCT/US2019/036586.

* cited by examiner

*Primary Examiner* — Shawquia Jackson
(74) *Attorney, Agent, or Firm* — Lin Yu, Esq.; Juniv LLP

(57) ABSTRACT

Compounds with amino amide linkers and pharmaceutical compositions and medicaments comprising such compounds are disclosed. In addition, methods of making such compounds and their uses for treating or ameliorating diseases, disorders, or conditions associated with protein malfunction, such as cancer, are provided.

29 Claims, No Drawings

AMINOAMIDE COMPOUNDS

INCORPORATION BY REFERENCE TO PRIORITY APPLICATION

The present application claims the benefit of priority to U.S. Provisional Application No. 62/684,541, filed Jun. 13, 2018, and 62/731,596, filed Sep. 14, 2018, both of which are hereby incorporated by reference in their entireties.

BACKGROUND

Field

Compounds, methods of making such compounds, pharmaceutical compositions and medicaments comprising such compounds, and uses of such compounds to treat, prevent or diagnose diseases, disorders, or conditions associated with protein malfunction are provided.

Aberrant protein function, and/or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Tumor necrosis factor-alpha (TNF-alpha, or TNF-α) and interleukin-1 (IL-1) are pro-inflammatory cytokines that mediate inflammatory responses associated with infectious agents and other cellular stresses. Overproduction of these cytokines is believed to underlie the progression of many inflammatory diseases including rheumatoid arthritis (RA), Crohn's disease, inflammatory bowel disease, endotoxin shock, osteoporosis, neurodegenerative diseases (such as multiple sclerosis, Alzheimer's disease, Parkinson's disease), congestive heart failure, and psoriasis among others.

Recent data from clinical trials support the use of protein antagonists of cytokines, for example soluble TNF-α receptor fusion protein (etanercept) or the monoclonal TNF-α antibody (infliximab), for the treatment of rheumatoid arthritis, Crohn's disease, juvenile chronic arthritis and psoriatic arthritis. Thus, the reduction of pro-inflammatory cytokines such as TNF-α and interleukin-1 (IL-1) has become an accepted therapeutic approach for potential drug intervention in these conditions.

Moreover, IL-2 is now FDA approved for the treatment of renal cancer and melanoma patients, with durable, complete remissions achieved with IL-2 up to 148 months. However, the short half-life of IL-2 in serum requires that large amounts of IL-2 be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional targets include several candidate genes involved in apoptosis and cell survival, including the translation termination factor GSPT1 (eRF3a), casein kinase 1α (CK1α), and the zinc-finger transcription factors aiolos, helios, and ikaros. Aiolos, helios, and ikaros are transcription factors whose expression is restricted to lymphoid lineages. For example, aiolos binds to the Bcl-2 promoter, and also interacts with the Bcl-2 and Bcl-XL proteins to promote cell survival. Upregulation of aiolos expression, for example, can reduce apoptosis of HIV-1 infected cells.

Likewise, expression of aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Similarly, aberrant ikaros and helios expression may promote Bcl-XL expression, driving the development of hematopoietic malignancies. Thus, downregulation of aiolos, ikaros, and/or helios may reduce or eliminate metastasis.

GSPT1 mediates stop codon recognition and facilitates release of a nascent peptide from the ribosome and is also involved in several other critical cellular processes, such as cell cycle regulation, cytoskeleton organization and apoptosis. Accordingly, decreased levels of GSPT1 may impair control of cell proliferation and facilitate cell migration and scar formation. Indeed, GSPT1 has been implicated as an oncogenic driver of several different cancer types, including breast cancer, hepatocellular carcinoma, gastric cancer, and prostate cancer. See, e.g., Brito, et al., *Carcinogenesis, Vol.* 26, No. 12, pp. 2046-49 (2005); Brito, et al., *Canc. Geneti. Cytogen.*, Vol. 195, pp. 132-42 (2009); Tavassoli, et al., *Med. Oncol.*, Vol. 29, pp. 1581-85 (2011); Wright and Lange, *Rev. Urol.*, Vol. 9, No. 4, pp. 207-213 (2007); Hoshino, et al., *Apoptosis*, Vol. 17, pp. 1287-99 (2012); Liu, et. al., PLOS One, Vol. 9, No. 1, e86371 (2014); and Jean-Jean, et al., *Mol. Cell. Bio.*, Vol. 27, No. 16, pp. 5619-29 (2007). GSPT1 also contributes to glial scar formation and astrogliosis after a central nervous system (CNS) injury. See, e.g., Ishii et al., *J. Biol. Chem.*, Vol. 292, No. 4, pp. 1240-50 (2017).

Casein kinase 1α (CK1α) is a component of the β-catenin-degradation complex and a critical regulator of the Wnt signaling pathway, and its ablation induces both Wnt and p53 activation. Schittek and Sinnberg, *Mol. Cancer.* 2014, 13, 231; Cheong and Virshup, *J. Biochem. Cell Biol.* 2011, 43, 465-469; Elyada et al., *Nature* 2011, 470, 409-413. CK1α phosphorylates β-catenin, which is subsequently further phosphorylated by GSK-3β. This destabilizes β-catenin and marks the protein for ubiquitination and proteasomal degradation. Thus, CK1α functions as a molecular switch for the Wnt pathway. Amit et al., *Genes Dev.* 2002, 16, 1066-1076. CK1α is critical for embryogenesis and plays an important role in tissue development and response to DNA damage, at least partly coordinated with p53. Elyada et al., *Nature* 2011, 470, 409-413; Schneider et al., *Cancer Cell* 2014, 26, 509-520. Levine and Oren, *Nat. Rev. Cancer* 2009, 9, 749-758.

Indeed, CK1α also phosphorylates p53, which inhibits binding to MDM2 (a p53 inhibitor) and stabilizes p53's binding interactions with the transcriptional machinery. Huart, et al., *J. Biol. Chem.* 2009, 284, 32384-32394. Thus, inhibiting CK1α activity increases cellular levels of p53. This is of particular importance for skin cancer, which has killed more people since 1980 than all other types of cancer combined. Stern, *Arch Dermatol.* 2010, 146, 279-282.

One mechanism to disrupt protein drivers of disease is to decrease the cellular concentration of these proteins. For example, proteolytic degradation of cellular proteins is essential to normal cell function. Hijacking this process, by targeting specific disease-related proteins, presents a novel mechanism for the treatment of disease. The irreversible nature of proteolysis makes it well-suited to serve as a regulatory switch for controlling unidirectional processes.

Ubiquitin-mediated proteolysis begins with ligation of one or more ubiquitin molecules to a particular protein substrate. Ubiquitination occurs through the activity of ubiquitin-activating enzymes (E1), ubiquitin-conjugating enzymes (E2), and ubiquitin-protein ligases (E3), acting sequentially to attach ubiquitin to lysine residues of substrate proteins. The E3 ligases confer specificity to ubiquitination reactions by binding directly to particular substrates.

SUMMARY

The compounds disclosed in the present application have been discovered to exert surprising and unexpected biological effects. In particular, the compounds disclosed in the present application modulate protein function and/or modulate protein levels to restore protein homeostasis.

Some embodiments provide a compound of Formula (I):

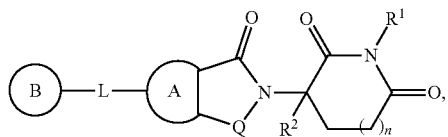
(I)

or a pharmaceutically acceptable salt thereof, wherein n is 0, 1, or 2;

$R^1$ is H, deuterium, $C_1$-$C_6$ alkyl,

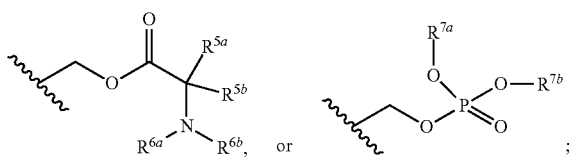

$R^2$ is H, deuterium, fluoro, or $C_1$-$C_6$ alkyl;

Q is C=O or $CR^{4a}R^{4b}$;

Ring A is

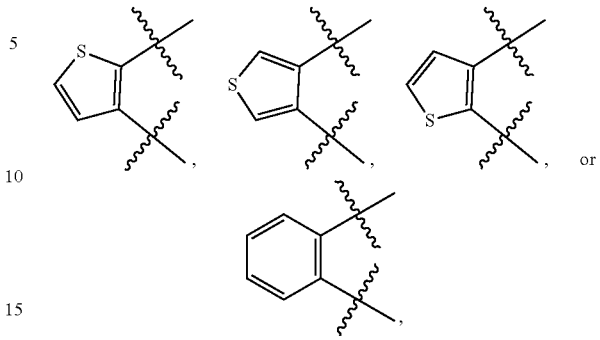

wherein Ring A is optionally substituted with one or more $R^A$;

Ring B is $C_6$-$C_{10}$ aryl, 5 to 10 membered heteroaryl, $C_3$ to $C_8$ carbocyclyl, or 3 to 10 membered heterocyclyl, each optionally substituted with one or more $R^B$;

L is

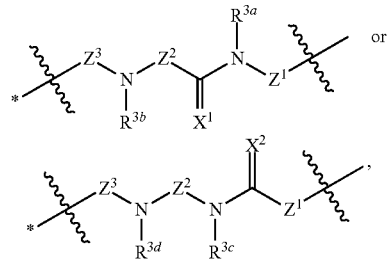

wherein the asterisk * indicates the point of connection to ring B;

each $X^1$ and $X^2$ is independently O, S, or NH;

$Z^1$ is a bond or —$(CR^{8a}R^{8b})_{m1}$—;

$Z^2$ is —$(CR^{8c}R^{8d})_{m2}$—;

$Z^3$ is a bond or —$(CR^{8e}R^{8f})_{m3}$—;

each $R^{3a}$, $R^{3b}$, $R^{3c}$, $R^{3d}$, $R^{4a}$, and $R^{4b}$ is independently H, deuterium, or $C_1$-$C_6$ alkyl;

each $R^{5a}$, $R^{6a}$, $R^{6b}$, $R^{7a}$, each $R^{7b}$, and $R^{7b}$ is independently H, optionally substituted $C_1$-$C_6$ alkyl or optionally substituted $C_3$-$C_6$ cycloalkyl; or $R^{6a}$ and $R^{6b}$ together with the nitrogen atom to which they are attached form an optionally substituted 5 or 6 membered heterocyclyl;

each $R^{8a}$, $R^{8b}$, $R^{8c}$, $R^{8d}$, $R^{8e}$ and $R^{8f}$ is independently H, deuterium, halogen, hydroxy, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl; and each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, amino($C_1$-$C_6$ alkyl), —(C=O)$NR^{10a}R^{10b}$, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each $R^B$ is independently halogen, hydroxyl, cyano, nitro, acyl, optionally substituted $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, amino($C_1$-$C_6$ alkyl), —(C=O)$NR^{10a}R^{10b}$, ($C_1$-$C_6$ alkoxy)$C_1$-$C_6$ alkyl, —O—($C_1$-$C_6$ alkoxy)$C_1$-$C_6$ alkyl, optionally substituted $C_3$-$C_7$ cycloalkyl, optionally substituted $C_3$-$C_7$ cycloalkyl($C_1$-$C_6$ alkyl), optionally substituted $C_6$-$C_{10}$ aryl, optionally substituted $C_6$-$C_{10}$ aryl($C_1$-$C_6$ alkyl), optionally substituted 5 to 10 membered heteroaryl, optionally substituted 5 to 10 membered heteroaryl($C_1$-$C_6$ alkyl), optionally substituted heterocyclyl, or optionally substituted heterocyclyl($C_1$-$C_6$ alkyl);

each $R^{10a}$ and $R^{10b}$ is independently H or $C_1$-$C_6$ alkyl, or $R^{10a}$ and $R^{10b}$ together with the nitrogen atom to which they are attached form an optionally substituted 5 or 6 membered heterocyclyl optionally substituted with one or more $R^9$;

each $R^9$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, halogen, or cyano; or two geminal $R^9$ form oxo (=O); and each of m1, m2, and m3 is independently 1, 2, 3, 4, or 5.

In some embodiments, each $R^B$ is independently halogen, hydroxyl, cyano, nitro, acyl, optionally substituted $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, amino($C_1$-$C_6$ alkyl), —(C=O)NR$^{10a}$R$^{10b}$, ($C_1$-$C_6$ alkoxy)$C_1$-$C_6$ alkyl, —O—($C_1$-$C_6$ alkoxy)$C_1$-$C_6$ alkyl, $C_3$-$C_7$ cycloalkyl optionally substituted with one or more $R^9$, $C_3$-$C_7$ cycloalkyl($C_1$-$C_6$ alkyl) optionally substituted with one or more $R^9$, $C_6$-$C_{10}$ aryl optionally substituted with one or more $R^9$, $C_6$-$C_{10}$ aryl($C_1$-$C_6$ alkyl) optionally substituted with one or more $R^9$, 5 or 6 membered heteroaryl optionally substituted with one or more $R^9$, 5 or 6 membered heteroaryl($C_1$-$C_6$ alkyl) optionally substituted with one or more $R^9$, heterocyclyl optionally substituted with one or more $R^9$, and heterocyclyl($C_1$-$C_6$ alkyl) optionally substituted with one or more $R^9$.

In some embodiments, the compound of Formula (I) is also represented by Formula (Ia), (Ib), (Ic), (Id), (Ie), (If), (Ig), (Ih), or (Ii):

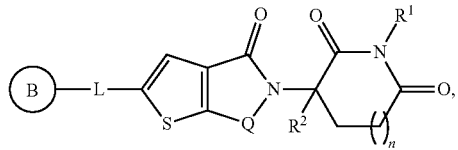
(Ia)

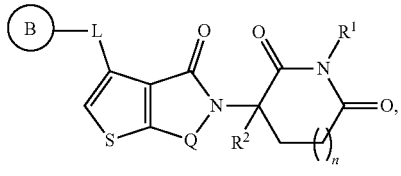
(Ib)

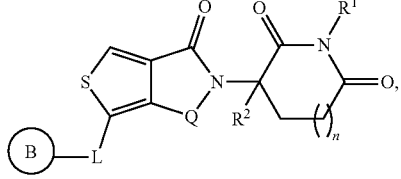
(Ic)

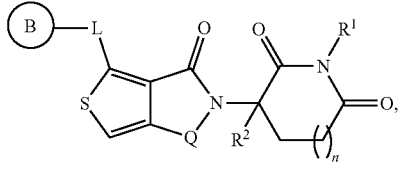
(Id)

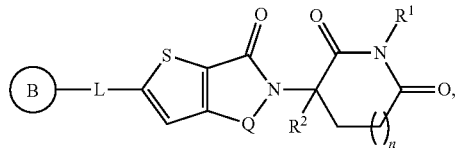
(Ie)

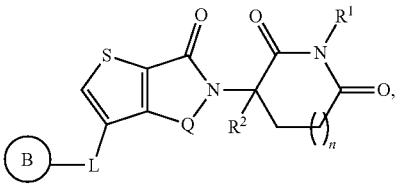
(If)

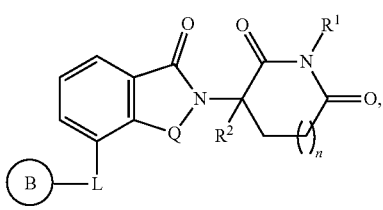
(Ig)

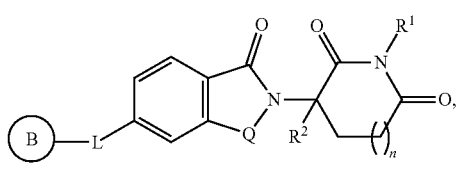
(Ih)

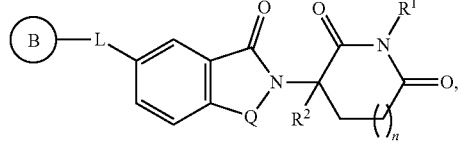
(Ii)

or a pharmaceutically acceptable salt thereof.

Some embodiments of the present disclosure provide a pharmaceutical composition, comprising a compound of Formula (I), (Ia), (Ib), (Ic), (Id), (Ie), (If), (Ig), (Ih), or (Ii), or a pharmaceutically acceptable salt thereof, and at least one pharmaceutically acceptable carrier.

Some embodiments of the present disclosure provide a method of modulating the activity of a protein in a biological sample, comprising contacting the biological sample with a compound of Formula (I), (Ia), (Ib), (Ic), (Id), (Ie), (If), (Ig), (Ih), or (Ii), or a pharmaceutically acceptable salt thereof, or a pharmaceutical composition thereof; wherein the protein is IL-1β, IL-2, IL-6, TNFα, CK1α, GSPT1, aiolos, ikaros, or helios. In some embodiments, the method inhibits the activity of the protein. In some embodiments, the step of contacting comprises contacting the biological sample with an effective amount of the compound of Formula (I), (Ia), (Ib), (Ic), (Id), (Ie), (If), (Ig), (Ih), or (Ii), or a pharmaceutically acceptable salt thereof, or a pharmaceutical composition thereof.

Some embodiments of the present disclosure provide a method of treating, ameliorating, or preventing a hematological malignancy or a solid tumor in a subject, the method comprising administering a therapeutically effective amount of a compound of Formula (I), (Ia), (Ib), (Ic), (Id), (Ie), (If), (Ig), (Ih), or (Ii), or a pharmaceutically acceptable salt thereof, or a pharmaceutical composition thereof to the subject in need thereof. In some embodiments, the hematological malignancy or the solid tumor is associated with one or more proteins selected from a IL-1β, IL-2, IL-6, TNFα, CK1α, GSPT1, aiolos, ikaros, and helios, and combinations of any of the foregoing. In some further embodiments, the hematological malignancy is leukemia, lymphoma, or multiple myeloma.

Some embodiments of the present disclosure provide a method of treating, ameliorating, or preventing a disease, disorder, or condition, the method comprising administering a therapeutically effective amount of a compound of Formula (I), (Ia), (Ib), (Ic), (Id), (Ie), (If), (Ig), (Ih), or (Ii), or a pharmaceutically acceptable salt thereof, or a pharmaceutical composition thereof to the subject in need thereof; wherein the disease, disorder, or condition is a neurodegenerative disease, fibrosis, lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, and chronic obstructive pulmonary disease. In some embodiments, the disease, disorder or condition is associated with one or more proteins selected from the group consisting of IL-1β, IL-2, IL-6, TNFα, CK1α, GSPT1, aiolos, ikaros, helios, and any combinations thereof.

DETAILED DESCRIPTION

Disclosed herein are compounds useful for the treatment of various diseases, disorders, or conditions, such as inflammatory diseases and cancers. In some embodiments, these compounds are modulators of various protein activities, for example, a cytokine (such as IL-1β, IL-2, and IL-6), TNFα, aiolos, ikaros, helios, CK1α, or GSPT1. In some aspects, these compounds are inhibitors of the protein activities. In other aspects, certain compounds described herein may induce protein activities (e.g., IL-2).

The section headings used herein are for organizational purposes only and are not to be construed as limiting the subject matter described.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, common organic abbreviations are defined as follows:

ACN acetonitrile
AcOH acetic acid
$CCl_4$ carbon tetrachloride
CDI 1,1'-carbonyldiimidazole, N,N'-carbonyldiimidazole
d day, days
DCM dichloromethane, methylene chloride
DEAD diethyl azodicarboxylate
DIEA N,N-diisopropylethylamine
DMA N,N-dimethylamide
DMF N,N-dimethylformamide
DMSO dimethylsulfoxide
EDAC.HCl 1-(3-dimethylaminopropyl)-3-ethylcarbodiimide hydrochloride
EDCI 1-ethyl-3-(3-dimethylaminopropyl)carbodiimide
Ether diethyl ether
EA ethyl acetate
EtOH ethanol
$K_2CO_3$ potassium carbonate
LiAH lithium aluminium hydride
LiCl lithium chloride
LiOH lithium hydroxide
h hour, hours
$H_2$ hydrogen
HCl hydrochloric acid, hydrochloride
HOBt 1-hydroxybenzotriazole
MeOH MeOH
m minute, minutes
$NaHCO_3$ sodium bicarbonate
$Na_2SO_4$ sodium sulfate
NBS N-bromosuccinimide
$N_2$ nitrogen
Pd/C palladium on activated carbon
PE petroleum ether
RT room temperature
T3P propylphosphonic anhydride
TEA triethylamine
TFA trifluoroacetic acid
THF tetrahydrofuran
quant quantitative yield The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^a$ and $R^b$, and the atom to which it is attached, are indicated to be "taken together" or "joined together" it means that they are covalently bonded to one another to form a ring:

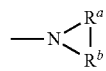

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from alkyl, cycloalkyl, aryl, heteroaryl, heterocyclyl, aralkyl, heteroaralkyl, heterocyclyl (alkyl), hydroxy, alkoxy, cycloalkoxy, aryloxy, acyl, mercapto, alkylthio, arylthio, cyano, halogen, C-amido, N-amido, C-carboxy, O-carboxy, isocyanato, thiocyanato, isothiocyanato, nitro, haloalkyl, haloalkoxy, amino, and alkylamino. When a group is not described as "optionally substituted," "unsubstituted" or "substituted," such group is unsubstituted unless the definition of such group states otherwise.

As used herein, "$C_a$ to $C_b$" in which "a" and "b" are integers refer to the number of carbon atoms in an alkyl group, or the number of ring atoms of a cycloalkyl, aryl, heteroaryl or heterocyclyl group. That is, the alkyl, ring of the cycloalkyl, and ring of the aryl, can contain from "a" to "b", inclusive, carbon atoms. Likewise, the ring of the heteroaryl and ring of the heterocyclyl can contain from "a" to "b", inclusive, total ring atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, cycloalkyl aryl, heteroaryl or heterocyclyl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro[3.3]heptane and spiro[4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogen in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

"Alkylene groups" are straight-chained —$CH_2$— tethering groups, forming bonds to connect molecular fragments via their terminal carbon atoms. Alkylene groups contain from 1 to 10 carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). An alkylene group can be substituted by replacing one or more hydrogen of the alkylene group with a substituent(s) listed under the definition of "substituted."

As used herein, "aralkyl" and "aryl(alkyl)" refer to an aryl group, as defined above, connected, as a substituent, via an alkylene group, as described above. The alkylene and aryl group of an aralkyl may be substituted or unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group, as defined above, connected, as a substituent, via an alkylene group, as defined above. The alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

As used herein, a "heterocyclyl(alkyl)" or "heterocyclylalkyl" refers to a heterocyclic or a heterocyclyl group, as defined above, connected, as a substituent, via an alkylene group, as defined above. The alkylene and heterocyclyl groups of a heterocyclyl(alkyl) may be substituted or unsubstituted. Examples include but are not limited to tetrahydrofuranylmethyl, piperazinylmethyl, and morpholinylethyl. When a heterocyclylalkyl group contains a secondary amino group (i.e., —NH—), the alkyl portion of the heterocyclylalkyl may replace the hydrogen on the nitrogen in the heterocyclyl ring, such that the heterocyclyl ring is linked to the alkyl potion of the heterocyclylalkyl group via the nitrogen atom.

As used herein, "N—($C_1$-$C_6$ alkyl) unsubstituted heterocyclyl" refers to a heterocyclyl group, as defined herein, substituted on one nitrogen atom with an alkyl group, as defined herein. The heterocyclyl portion of the N—($C_1$-$C_6$ alkyl) unsubstituted heterocyclyl and the alkyl portion of the N—($C_1$-$C_6$ alkyl) unsubstituted heterocyclyl are otherwise unsubstituted (i.e., the alkyl group is the sole substitution on the heterocyclyl group). Examples of such "N—($C_1$-$C_6$ alkyl) unsubstituted heterocyclyl" groups include but are not limited to, N-methyl-isoxazolidine, N-isopropyl-morpholine, N-methyl-piperidine, N-ethyl-piperazine, N-methyl-pyrrolidine, N-methyl-pyrrolidone, and N-propyl-pyrrolidione.

As used herein, a "cycloalkyl(alkyl)" refers to a cycloalkyl group, as defined above, connected, as a substituent, via an alkylene group, as defined above. The alkylene and cycloalkyl portion of a cycloalkyl(alkyl) may be substituted or unsubstituted. Examples include but are not limited to

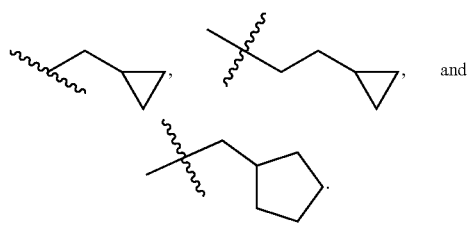

As used herein, "alkoxy" refers to the formula —OR wherein R is an alkyl group, as defined herein. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "cycloalkoxy" refers to the formula —OR wherein R is a cycloalkyl group, as defined herein. A non-limiting list of cycloalkoxys is cyclopropoxy, cyclobutoxy, cyclopentoxy, and cyclohexoxy. A cycloalkoxy may be substituted or unsubstituted.

As used herein, "acyl" refers to a hydrogen, alkyl, aryl, heteroaryl, or heterocyclyl group, as defined above, connected, as substituents, via a carbonyl group. Examples include formyl, acetyl, propanoyl, and benzoyl. An acyl may be substituted or unsubstituted. A "carbonyl" group refers to a C=O group.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl, 1-chloro-2-fluoromethyl, and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy, and 2-fluoroisobutoxy. A haloalkoxy may be substituted or unsubstituted.

As used herein, "alkoxyalkyl" or "(alkoxy)alkyl" refers to an alkoxy group connected via an lower alkylene group, such as $C_2$-$C_8$ alkoxyalkyl, or ($C_1$-$C_6$ alkoxy)$C_1$-$C_6$ alkyl, for example, —($CH_2$)$_{1-3}$—$OCH_3$.

As used herein, "—O-alkoxyalkyl" or "—O-(alkoxy)alkyl" refers to an alkoxy group connected via an —O-(lower alkylene) group, such as —O—($C_1$-$C_6$ alkoxy)$C_1$-$C_6$ alkyl, for example, —O—($CH_2$)$_{1-3}$—$OCH_3$.

As used herein, "aryloxy" and "arylthio" refers to RO— and RS—, in which R is an aryl, as defined above, such as but not limited to phenyl. Both an aryloxy and arylthio may be substituted or unsubstituted.

As used herein, an "O-carboxy" group refers to a "RC(=O)O—*" group in which R can be hydrogen, alkyl, cycloalkyl, aryl, heteroaryl, heterocyclyl, aralkyl, or heterocyclyl(alkyl), as defined herein, and wherein "*" denotes the connect of the 0-carboxy group to the rest of the molecule. An O-carboxy may be substituted or unsubstituted.

As used herein "ester" and "C-carboxy" refer to a "*—C(=O)OR" group in which R can be hydrogen, alkyl, cycloalkyl, aryl, heteroaryl, heterocyclyl, aralkyl, or heterocyclyl(alkyl), as defined herein, and wherein "*" denotes the connect of the C-carboxy (or ester) group to the rest of the molecule. A C-carboxy or ester group may be substituted or unsubstituted.

As used herein, "amino" or "optionally substituted amino," as used herein refer to —$NR_AR_B$ where $R_A$ and $R_B$ are independently hydrogen, alkyl, cycloalkyl, aryl, heteroaryl, heterocyclyl, aralkyl, or heterocyclyl(alkyl), as defined herein. An unsubstituted amino is —$NH_2$.

As used herein, "alkylamino" or "(alkyl)amino" refers to a —$NR_AR_B$ group where $R_A$ and $R_B$ are hydrogen or alkyl as defined above, and at least one of $R_A$ and $R_B$ is alkyl. The alkyl portion of the (alkyl)amine, includes, for example, $C_1$-$C_6$ alkyl groups. Examples of alkylamino groups include, but are not limited to methylamino (—NHMe), ethylamino (—NHEt), dimethylamino (—N(Me)$_2$, methylethylamino (—N(Me)(Et)), and isopropylamino (—NHiPr).

As used herein, "aminoalkyl" or "amino(alkyl)" refers to an alkyl group in which one or more of the hydrogen atoms are replaced by an amino group or "—NR$_A$R$_B$" group as defined herein. The alkyl portion of the amino(alkyl), includes, for example, C$_1$-C$_6$ alkyl. Examples of aminoalkyl groups include, but are not limited to —(CH$_2$)$_{1-4}$NH$_2$, —(CH$_2$)$_{1-4}$—NHCH$_3$, —(CH$_2$)$_{1-4}$—NHC$_2$H$_5$, —(CH$_2$)$_{1-4}$—N(CH$_3$)$_2$, —(CH$_2$)$_{1-4}$—N(C$_2$H$_5$)$_2$, —(CH$_2$)$_{1-4}$—NH—CH(CH$_3$)$_2$, —(CH$_2$)$_{1-4}$N(CH$_3$)C$_2$H$_5$, and —CH(NH$_2$)CH$_3$.

As used herein, the term "hydroxy" refers to a —OH group.

A "cyano" group refers to a "—CN" group.

The term "azido" as used herein refers to a —N$_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "C-amido" group refers to a "*—C(=O)N(R$_A$R$_B$)" group in which R and R$_A$ can be independently hydrogen, alkyl, cycloalkyl, aryl, heteroaryl, heterocyclyl, aralkyl, or heterocyclyl(alkyl), as defined above, and wherein "*" denotes the connect of the C-amido group to the rest of the molecule. A C-amido may be substituted or unsubstituted.

An "N-amido" group refers to a "RC(=O)N(R$_A$)—*" group in which R and R$_A$ can be independently hydrogen, alkyl, cycloalkyl, aryl, heteroaryl, heterocyclyl, aralkyl, or heterocyclyl(alkyl), as defined above, and wherein "*" denotes the connect of the N-amido group to the rest of the molecule. An N-amido may be substituted or unsubstituted.

A "urea" group refers to a "—N(R$_A$R$_B$)—C(=O)—N(R$_A$R$_B$)—" group in which R$_A$ and R$_B$ can be independently hydrogen, alkyl, cycloalkyl, aryl, heteroaryl, heterocyclyl, aralkyl, or heterocyclyl(alkyl), as defined above. A urea group may be substituted or unsubstituted.

A "thiourea" group refers to a "—N(R$_A$R$_B$)—C(=S)—N(R$_A$R$_B$)—" group in which R$_A$ and R$_B$ can be independently hydrogen, alkyl, cycloalkyl, aryl, heteroaryl, heterocyclyl, aralkyl, or heterocyclyl(alkyl), as defined above. A thiourea group may be substituted or unsubstituted.

The term "halogen atom" or "halogen" as used herein, means any one of the radio-stable atoms of column 7 of the Periodic Table of the Elements, such as, fluorine, chlorine, bromine, and iodine.

Where the numbers of substituents is not specified (e.g., haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The term "prodrug" as used herein is a broad term, and is to be given its ordinary and customary meaning to a person of ordinary skill in the art (and is not to be limited to a special or customized meaning), and refers without limitation to a compound or a pharmaceutical composition that can be administered to a patient in a less active or inactive form, which can then be metabolized in vivo into a more active metabolite. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound. Certain compounds described herein are prodrugs.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

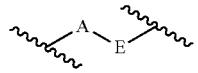

includes the substituent being oriented such that the A is attached at the leftmost attachment point of the molecule as well as the case in which A is attached at the rightmost attachment point of the molecule.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of pharmaceutically acceptable salts and/or conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond.

Likewise, it is understood that the compounds described herein, such as compounds of preferred embodiments, include the compound in any of the forms described herein (e.g., pharmaceutically acceptable salts, prodrugs, enantiomeric forms, tautomeric forms, and the like).

Compounds

Some embodiments provide a compound of Formula (I):

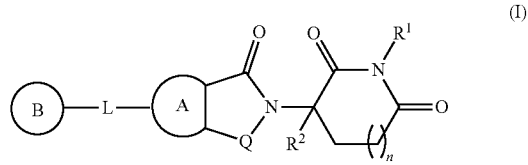

or a pharmaceutically acceptable salt thereof as described herein. In some embodiments, Ring A is

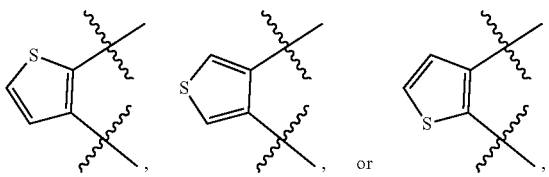 [SMILES: *c1ccsc1* ; *c1cscc1* ; *c1ccsc1*]

each optionally substituted with one substituent selected from the group consisting of deuterium, hydroxyl, halogen, cyano, nitro, optionally substituted amino, $C_1$-$C_6$ alkoxy, $C_1$-$C_6$ alkyl, $C_1$-$C_6$ alkylamino, and $C_1$-$C_6$ haloalkyl; each $R^{3a}$ and $R^{3c}$ is H; each $R^{8a}$ and $R^{8b}$ is H; each $R^{8c}$, $R^{8d}$, $R^{8e}$ and $R^{8f}$ is independently H, deuterium, fluoro or $C_1$ to $C_6$ alkyl; and Ring B is phenyl or naphthyl, each substituted with one, two or three substituents selected from the group consisting of halogen, $C_1$-$C_6$ alkyl, $C_1$-$C_6$ haloalkyl, $C_1$-$C_6$ alkylamino, an unsubstituted heterocyclyl, a heterocyclyl substituted with $C_1$-$C_6$ alkyl, an unsubstituted heterocyclyl ($C_1$-$C_6$ alkyl), and a heterocyclyl($C_1$-$C_6$ alkyl) substituted with $C_1$-$C_6$ alkyl.

In some embodiments, Ring A is

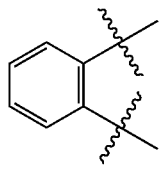 [SMILES: *c1ccccc1*]

and Ring A is not substituted with any $R^A$; Q is $CH_2$; $R^1$ is H; $R^2$ is H, deuterium, fluoro, or methyl; L is

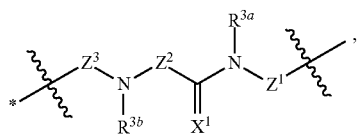

wherein each $R^{3a}$ and $R^{3b}$ is H; $X^1$ is O; $Z^1$ is —$(CH_2)_{m1}$—; $Z^2$ is —$(CH_2)_{m2}$—; $Z^3$ is a bond; each m1 and m2 is independently 1, 2, 3 or 4; and Ring B is phenyl, naphthyl, $C_4$-$C_6$ cycloalkyl, 4 to 6 membered heterocyclyl, or 5 to 6 membered heteroaryl, each optionally substituted with one, two, three or four substituents selected from the group consisting of fluoro, chloro, amino, —$CH_2N(CH_3)_2$, di($C_1$-$C_6$ alkyl)amino, $C_1$-$C_6$ alkyl, $C_1$-$C_6$ alkoxy, $C_1$-$C_6$ haloalkyl, $C_1$-$C_6$ haloalkoxy, acyl, 4 to 6 membered heterocyclyl, or N—($C_1$-$C_6$ alkyl)heterocyclyl.

In some embodiments, the compound of Formula (I) is represented by Formula (Ia)-(Ii):

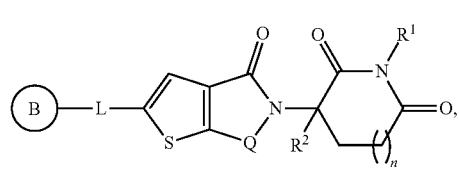

(Ia)

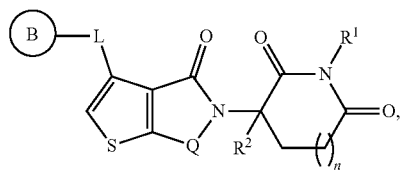

(Ib)

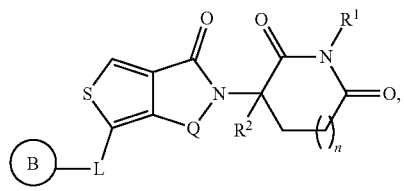

(Ic)

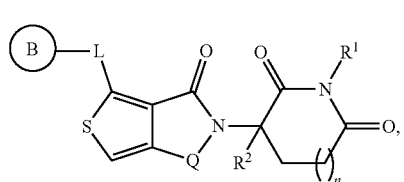

(Id)

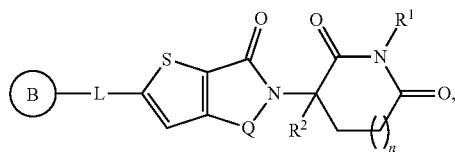

(Ie)

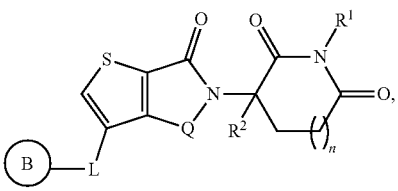

(If)

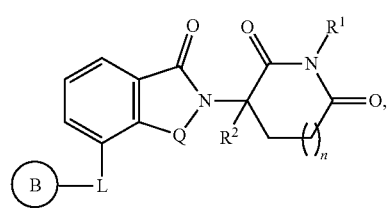

(Ig)

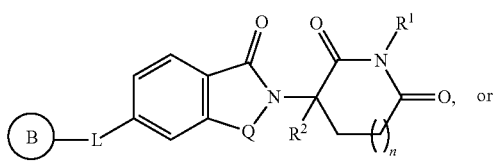

(Ih)

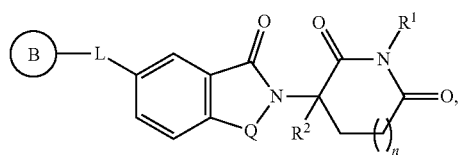

(Ii)

or a pharmaceutically acceptable salt thereof.

In some embodiments of the compounds of Formula (I), Ring A is

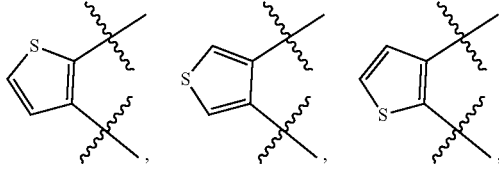

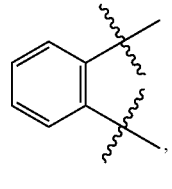

each optionally substituted with one or more $R^A$. In some other embodiments, Ring A is not substituted with any $R^A$. In some embodiments, each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, amino($C_1$-$C_6$ alkyl), —(C═O)NR$^{10a}$R$^{10b}$, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl. In some embodiments of the compounds of Formula (I), Ring A is

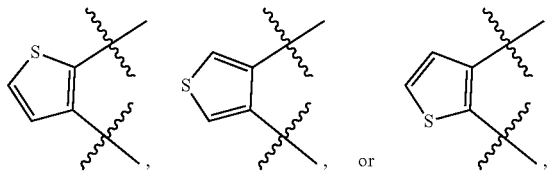 [SMILES: *c1ccsc1* ; *c1cscc1* ; *c1ccsc1*]

(for example, compounds with Formula (Ia)-(If)), each unsubstituted or substituted with one $R^4$. In some other embodiments of the compounds of Formula (I), Ring A is

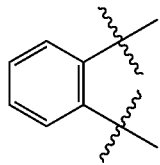 [SMILES: *c1ccccc1*]

(for example, compounds with Formula (Ig)-(Ii)), unsubstituted or substituted with one or more $R^4$. In some such embodiments, each $R^4$ is independently deuterium, hydroxyl, halogen, cyano, nitro, optionally substituted amino (e.g, —$NH_2$, or an amino substituted with one or two substituents selected from the group consisting of $C_1$-$C_6$ alkyl, $C_3$-$C_6$ cycloalkyl, $C_6$ aryl, 3- to 6-membered heterocyclyl, and 5- to 6-membered heteroaryl), $C_1$-$C_6$ alkoxy (e.g., methoxy, ethoxy, n-propoxy, isopropoxy, n-butoxy, sec-butoxy, t-butoxy, pentoxy (straight chain or branched), or hexoxy (straight chain or branched)), optionally substituted $C_1$-$C_6$ alkyl (such as those described herein), $C_1$-$C_6$ alkylamino, or $C_1$-$C_6$ haloalkyl. In some further embodiments, each $R^4$ is independently deuterium, hydroxyl, halogen, cyano, nitro, optionally substituted amino (such as those described herein), $C_1$-$C_6$ alkoxy, $C_1$-$C_6$ alkyl, $C_1$-$C_6$ alkylamino, or $C_1$-$C_6$ haloalkyl. In some further embodiments, $R^4$ is halogen, —$NH_2$, —$NH(C_1$-$C_4$ alkyl), —$N(C_1$-$C_4$ alkyl)$_2$, $C_1$-$C_6$ alkyl, or $C_1$-$C_6$ alkoxy. In one embodiment, $R^4$ is fluoro, for example, Ring A is

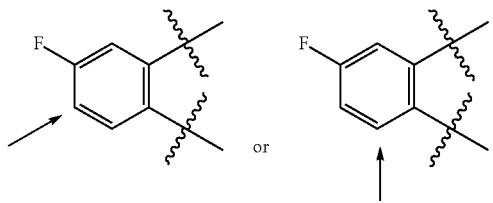 [SMILES: *c1ccc(F)cc1* ; *c1ccc(F)cc1*]

where the arrow indicate the attachment position of L.

In some embodiments of the compounds of Formula (I), (Ia), (Ib), (Ic), (Id), (Ie), (If), (Ig), (Ih), or (Ii), n is 0, 1, or 2. In some further embodiments, n is 1. In some further embodiments, n is 2. In some other embodiments, n is 0.

In some embodiments of the compounds of Formula (I), (Ia), (Ib), (Ic), (Id), (Ie), (If), (Ig), (Ih), or (Ii), $R^1$ is H, deuterium, or $C_1$-$C_6$ alkyl. In some embodiments, $R^1$ is H. In some embodiments, $R^1$ is deuterium. In some embodiments, $R^1$ is $C_1$-$C_6$ alkyl (for example, methyl, ethyl, n-propyl, isopropyl, n-butyl, sec-butyl, t-butyl, pentyl (straight chain or branched), or hexyl (straight chain or branched)). In some embodiments, $R^1$ is methyl. In some embodiments, $R^1$ is

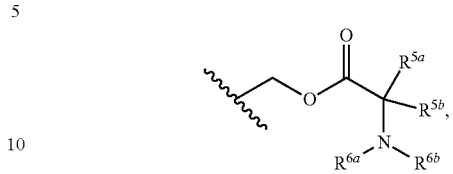

wherein each of $R^{5a}$, $R^{5b}$, $R^{6a}$, and $R^{6b}$ is independently H, optionally substituted $C_1$-$C_6$ alkyl (such as those described herein), optionally substituted $C_3$-$C_6$ cycloalkyl (such as those described herein), or $R^{6a}$ and $R^{6b}$, together with the nitrogen atom to which they are attached, form an optionally substituted 5- or 6-membered heterocyclyl containing zero or one additional heteroatom that is oxygen or nitrogen. In some further embodiments, each of $R^{5a}$, $R^{5b}$, $R^{6a}$, and $R^{6b}$ is independently H, $C_1$-$C_6$ alkyl, or $C_3$-$C_6$ cycloalkyl (such as cyclopropyl, cyclobutyl, cyclopentyl, and cyclohexyl), or $R^{6a}$ and $R^{6b}$, together with the nitrogen atom to which they are attached, form a 5- or 6-membered monocyclic heterocyclyl containing no more than one additional nitrogen or oxygen (such as a pyrrolidinyl, piperidinyl, piperazinyl, or morpholinyl). In some embodiments, one of $R^{5a}$ and $R^{5b}$ is H, and the other of $R^{5a}$ and $R^{5b}$ is $C_1$-$C_6$ alkyl (such as isopropyl or t-butyl). In some embodiments, both $R^{5a}$ and $R^{5b}$ are H. In some embodiments, both $R^{6a}$ and $R^{6b}$ are H. In some embodiments, one of $R^{6a}$ and $R^{6b}$ is H, and the other of $R^{6a}$ and $R^{6b}$ is $C_1$-$C_6$ alkyl (such as isopropyl or t-butyl). In some other embodiments, $R^1$ is

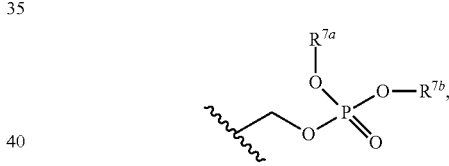

wherein each $R^{7a}$ and $R^{7b}$ is independently H, optionally substituted $C_1$-$C_6$ alkyl (such as those described herein), or optionally substituted $C_3$-$C_6$ cycloalkyl (such as those described herein). In some such embodiments, each $R^{7a}$ and $R^{7b}$ is independently H, $C_1$-$C_6$ alkyl, $C_3$-$C_6$ cycloalkyl. In some such embodiments, at least one of $R^{7a}$ and $R^{7b}$ is $C_1$-$C_6$ alkyl. In one embodiment, $R^{7a}$ and $R^{7b}$ are identical $C_1$-$C_6$ alkyl (such as isopropyl or t-butyl). In another embodiment, $R^{7a}$ and $R^{7b}$ are different $C_1$-$C_6$ alkyl.

In some embodiments of the compounds of Formula (I), (Ia), (Ib), (Ic), (Id), (Ie), (If), (Ig), (Ih), or (Ii), $R^2$ is H, deuterium, fluoro, or $C_1$-$C_6$ alkyl (such as those described herein). In some embodiments, $R^2$ is H, deuterium, fluoro, or methyl. In some embodiments, $R^2$ is H.

In some embodiments of the compounds of Formula (I), (Ia), (Ib), (Ic), (Id), (Ie), (If), (Ig), (Ih), or (Ii), Q is C=O or $CR^{4a}R^{4b}$, wherein each $R^{4a}$ and $R^{4b}$ is H, deuterium, or $C_1$-$C_6$ alkyl (for example, methyl, ethyl, n-propyl, isopropyl, n-butyl, sec-butyl, t-butyl, pentyl (straight chain or branched), or hexyl (straight chain or branched)). In some embodiments, Q is C=O, $CH_2$, or $CHCH_3$. In some embodiments, Q is C=O. In some embodiments, Q is $CH_2$. In some embodiments, Q is $CHCH_3$. In some embodiments, Q is CHD. In some embodiments, Q is $CR^{4a}R^{4b}$, wherein one of $R^{4a}$ and $R^{4b}$ is H or D, and the other of $R^{4a}$ and $R^{4b}$ is $C_1$-$C_6$ alkyl. In some embodiments, Q is $CR^{4a}R^{4b}$, wherein $R^{4a}$ and $R^{4b}$ are identical or different $C_1$-$C_6$ alkyl.

In some embodiments of the compounds of Formula (I), (Ia), (Ib), (Ic), (Id), (Ie), (If), (Ig), (Ih), or (Ii), L is

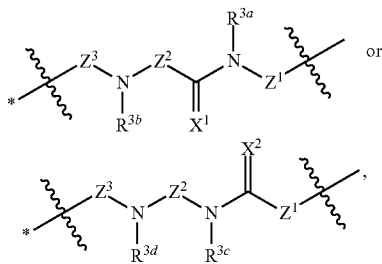

wherein the asterisk * indicates the point of connection to Ring B. In some embodiments, L is

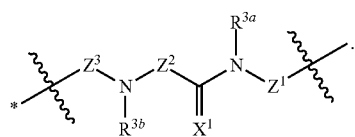

In some embodiments, L is

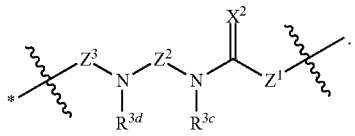

In some such embodiments, $Z^1$ is a bond or —$(CR^{8a}R^{8b})_{m1}$—, where one or both of $R^{8a}$ and $R^{8b}$ is H. In some embodiments, m1 is 1 or 2. In some embodiments, $R^{3a}$ is H. In some embodiments, $R^{3c}$ is H. In some embodiments, $X^1$ is O, NH, or S. In some embodiments, $X^1$ is O. In some embodiments, $X^1$ is NH. In some embodiments, $X^1$ is S. In some embodiments, $X^2$ is O, NH, or S. In some embodiments, $X^2$ is O. In some embodiments, $X^2$ is NH. In some embodiments, $X^2$ is S. In some embodiments, $R^{3b}$ is H, deuterium or $C_1$ to $C_6$ alkyl. In some embodiments, $R^{3b}$ is H. In some embodiments, $R^{3b}$ is methyl. In some embodiments, $R^{3b}$ is isopropyl. In some embodiments, $R^{3d}$ is H, deuterium, or a $C_1$ to $C_6$ alkyl. In some embodiments, $R^{3d}$ is H, methyl or isopropyl. In some embodiments, $Z^2$ is —$(CR^{8c}R^{8d})_{m2}$—, where each $R^{8c}$ and $R^{8d}$ is independently H, deuterium, halogen or $C_1$ to $C_6$ alkyl. In some further embodiments, one or both of $R^{8c}$ and $R^{8d}$ is H. In some embodiments, m2 is 1 or 2. In some embodiments, m2 is 1; and one of $R^{8c}$ and $R^{8d}$ is H, and the other of $R^{8c}$ and $R^{8d}$ is $C_1$-$C_3$ alkyl or halogen (e.g., methyl or fluoro). In one embodiment, $Z^2$ is —$CH_2$—. In another embodiment, $Z^2$ is —$CHCH_3$—. In another embodiment, $Z^2$ is —$CF_2$—. In some embodiments, $Z^3$ is a bond or —$(CR^{8e}R^{8f})_{m3}$—. In some embodiments, $Z^3$ is a bond. In some embodiments, $Z^3$ is —$(CR^{8e}R^{8f})_{m3}$— where each $R^{8e}$ and $R^{8f}$ is independently H, deuterium, halogen, or $C_1$ to $C_6$ alkyl. In some embodiments, m3 is 1 or 2. In some further embodiments, one or both of $R^{8e}$ and $R^{8f}$ is H. In some embodiments, m3 is 1; and one of $R^{8e}$ and $R^{8f}$ is H, and the other of $R^{8e}$ and $R^{8f}$ is $C_1$-$C_3$ alkyl or halogen (e.g., methyl or fluoro). In some embodiments, each $Z^1$ and $Z^3$ is a bond. In some such embodiments, $Z^1$ is a bond and $Z^3$ is —$(CR^{8e}R^{8f})_{m3}$—. In some other embodiments, $Z^1$ is —$(R^{8a}R^{8b})^{m1}$— and $Z^3$ is a bond. In some embodiments, $Z^1$ is —$(CR^{8a}R^{8b})^{m1}$— and $Z^3$ is —$(CR^{8e}R^{8f})_{m3}$—. In some such embodiments, $Z^1$ is —$(CH_2)_{m1}$—; and each of $R^{8c}$, $R^{8d}$, $R^{8e}$ and $R^{8f}$ is independently H, deuterium, halogen or $C_1$ to $C_6$ alkyl. In some embodiments, $Z^1$ is —$(CH_2)_{m1}$—; $Z^3$ is —$(CH_2)_{m3}$—; and each of of $R^{8c}$ and $R^{8d}$ is H or at least one of $R^{8c}$ and $R^{8d}$ is halogen or $C_1$-$C_6$ alkyl (e.g., fluoro or methyl). In some embodiments, each m1, m2 and m3 is independently 1 or 2. In some embodiments, $Z^1$ is —$CH_2$—; $Z^2$ is —$(CHR^{8c})_{m2}$—; and $Z^3$ is a bond. In some embodiments, $Z^1$ is $CH_2$; $Z^2$ is $CH_2$ or $CHCH_3$; and $Z^3$ is a bond. In some embodiments, $Z^1$ is a bond; $Z^2$ is $CH_2$ or $CHCH_3$; and $Z^3$ is $CH_2$.

In some further embodiments of the compounds of Formula (I), (Ia), (Ib), (Ic), (Id), (Ie) or (If), Ring A is

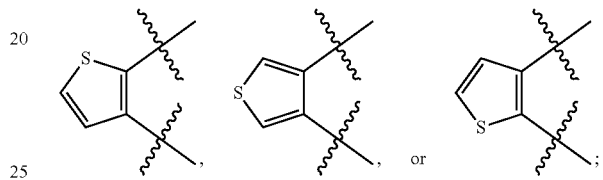

L is

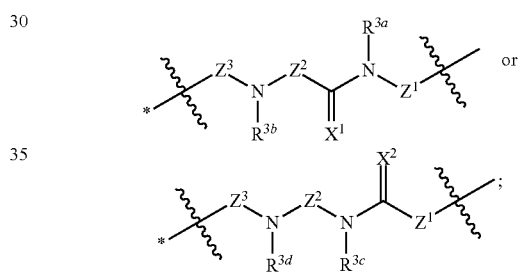

$Z^3$ is a bond or —$(CR^{8e}R^{8f})_{m3}$—; each of $R^{3a}$, $R^{3b}$, $R^{8a}$, and $R^{8b}$ is H; and each of $R^{8c}$, $R^{8d}$, $R^{8e}$, and $R^{8f}$ is independently H, deuterium, fluoro, or $C_1$ to $C_6$ alkyl. In some such embodiments, $Z^3$ is a bond. In some other such embodiments, $Z^3$ is —$CH_2$—.

In some other further embodiments of the compounds of Formula (I), (Ig), (Ih), or (Ii), Ring A is

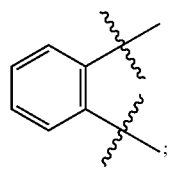 [SMILES: *c1ccccc1*]

L is

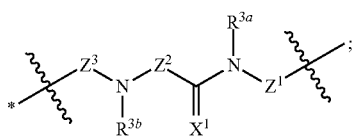

each $R^{3a}$ and $R^{3b}$ is H; $X^1$ is O; $Z^1$ is —$(CH_2)_{m1}$—; $Z^2$ is —$(CH_2)_{m2}$—; $Z^3$ is a bond; and each m1 and m2 is independently 1, 2, 3 or 4.

In some embodiments of the compounds of Formula (I), (Ia), (Ib), (Ic), (Id), (Ie), (If), (Ig), (Ih), or (Ii), Ring B is $C_6$-$C_{10}$ aryl (e.g., phenyl, or naphthyl), 5 to 10 membered heteroaryl (e.g., five or six-membered heteroaryl containing one, two or three heteroatoms selected from O, N or S; including but not limited to pyridyl, pyrimidyl, thienyl, furyl, pyrrolyl, pyrazolyl, imidazolyl, thiazolyl, isothiazolyl, diathiazolyl, oxazolyl, and isoxazolyl), $C_3$ to $C_8$ carbocyclyl (e.g., cyclopropyl, cyclobutyl, cyclopentyl, or cyclohexyl), or 3 to 10 membered heterocyclyl (e.g., four to six-membered monocyclic heterocyclyl containing one, two or three heteroatoms selected from O, N or S; including but not limited to pyrrolidine, piperidine, piperazine, or morpholine), each optionally substituted with one or more $R^B$ described herein. In some embodiments, each $R^B$ is independently halogen, hydroxyl, cyano, nitro, acyl, optionally substituted $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, amino($C_1$-$C_6$ alkyl), —(C=O)$NR^{10a}R^{10b}$, ($C_1$-$C_6$ alkoxy)$C_1$-$C_6$ alkyl, —O—($C_1$-$C_6$ alkoxy)$C_1$-$C_6$ alkyl, $C_3$-$C_7$ cycloalkyl optionally substituted with one or more $R^9$, $C_3$-$C_7$ cycloalkyl($C_1$-$C_6$ alkyl) optionally substituted with one or more $R^9$, $C_6$-$C_{10}$ aryl optionally substituted with one or more $R^9$, $C_6$-$C_{10}$ aryl($C_1$-$C_6$ alkyl) optionally substituted with one or more $R^9$, 5 or 6 membered heteroaryl optionally substituted with one or more $R^9$, 5 or 6 membered heteroaryl($C_1$-$C_6$ alkyl) optionally substituted with one or more $R^9$, heterocyclyl optionally substituted with one or more $R^9$, or heterocyclyl($C_1$-$C_6$ alkyl) optionally substituted with one or more $R^9$. In some embodiments, each $R^9$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^9$ form oxo (=O). In some embodiments, Ring B is unsubstituted with any $R^B$. In some other embodiments, Ring B is substituted with one, two or three $R^B$ described herein. Non-limiting embodiments of the heterocyclyl or heterocyclyl($C_1$-$C_6$ alkyl) of the $R^B$ substituent include each optionally substituted with one or more $R^9$. Non-limiting embodiments of the $C_3$-$C_7$ cycloalkyl and $C_3$-$C_7$ cycloalkyl($C_1$-$C_6$ alkyl) of the $R^B$ substituent include

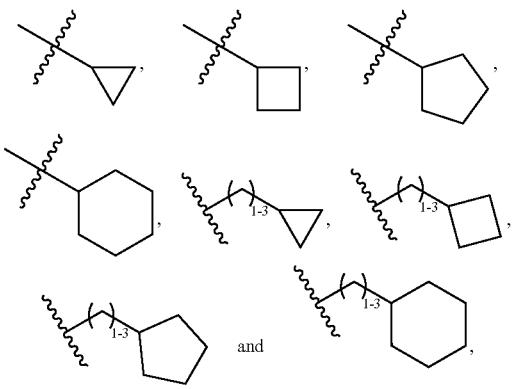

each optionally substituted with one or more $R^9$. Non-limiting embodiments of $C_6$-$C_{10}$ aryl and $C_6$-$C_{10}$ aryl($C_1$-$C_6$ alkyl) of the $R^B$ substituent include phenyl and benzyl, each optionally substituted with one or more $R^9$. Non-limiting embodiments of 5 or 6 heteroaryl and 5 or 6 heteroaryl ($C_1$-$C_6$ alkyl) of the $R^B$ substituent include pyridyl, pyrimidyl, thienyl, furyl, pyrrolyl, pyrazolyl, imidazolyl, thiazolyl, isothiazolyl, diathiazolyl, oxazolyl, isoxazolyl, —$(CH_2)_{1-3}$-pyridyl, —$(CH_2)_{1-3}$-pyrimidyl, —$(CH_2)_{1-3}$-thienyl, —$(CH_2)_{1-3}$-furyl, —$(CH_2)_{1-3}$-pyrrolyl, —$(CH_2)_{1-3}$-pyrazolyl, —$(CH_2)_{1-3}$-imidazolyl, —$(CH_2)_{1-3}$-thiazolyl, —$(CH_2)_{1-3}$-isothiazolyl, —$(CH_2)_{1-3}$-diathiazolyl, —$(CH_2)_{1-3}$-oxazolyl, and —$(CH_2)_{1-3}$-isoxazolyl, each optionally substituted with one or more $R^9$. In some embodiments, $R^9$ is halogen, $C_1$-$C_6$ alkyl, or $C_1$-$C_6$ haloalkyl (e.g., trifluoromethyl).

In some further embodiments, Ring B is phenyl, naphthyl, $C_4$-$C_6$ cycloalkyl, 4 to 6 membered heterocyclyl, or 5 to 6 membered heteroaryl (e.g., pyridyl), each optionally substituted with one, two, three or four $R^B$ described herein. In some embodiments, Ring B is phenyl or pyridyl, optionally substituted with one, two or three $R^B$. In some other embodiments, Ring B is phenyl or pyridyl not substituted with any $R^B$. In some such embodiments, each $R^B$ is independently halogen, $C_1$-$C_6$ alkyl, $C_1$-$C_6$ haloalkyl, $C_1$-$C_6$ alkoxy, $C_1$-$C_6$ haloalkoxy, —$NH_2$, $C_1$-$C_6$ alkylamino, amino($C_1$-$C_6$ alkyl), acyl, $C_3$-$C_7$ cycloalkyl optionally substituted with one or more $R^9$, $C_3$-$C_7$ cycloalkyl($C_1$-$C_6$ alkyl) optionally substituted with one or more $R^9$, heterocyclyl optionally substituted with one or more $R^9$ (e.g., optionally substituted with $C_1$-$C_6$ alkyl or halogen), or heterocyclyl($C_1$-$C_6$ alkyl) optionally substituted with one or more $R^9$ (e.g., optionally substituted with $C_1$-$C_6$ alkyl or halogen). In some embodiments, $R^B$ is chloro, fluoro, $C_1$-$C_6$ alkyl, $C_1$-$C_6$ haloalkyl, —$NH_2$, $C_1$-$C_6$ alkylamino, amino($C_1$-$C_6$ alkyl), unsubstituted $C_3$-$C_7$ cycloalkyl, $C_3$-$C_7$ cycloalkyl substituted with $C_1$-$C_6$ alkyl, unsubstituted $C_3$-$C_7$ cycloalkyl($C_1$-$C_6$ alkyl), $C_3$-$C_7$ cycloalkyl($C_1$-$C_6$ alkyl) substituted with $R^9$ (e.g., $C_1$-$C_6$ alkyl), unsubstituted 4 to 6 membered heterocyclyl, 4 to 6 membered heterocyclyl substituted with $R^9$ (e.g., $C_1$-$C_6$ alkyl), unsubstituted 4 to 6 membered heterocyclyl($C_1$-$C_6$ alkyl), or 4 to 6 membered heterocyclyl($C_1$-$C_6$ alkyl) substituted with $R^9$ (e.g., $C_1$-$C_6$ alkyl). In some further embodiments, $R^B$ is halogen (e.g., fluoro or chloro). In some further embodiments, $R^B$ is $C_1$-$C_6$ alkyl (e.g., methyl, ethyl, n-propyl, or isopropyl). In some further embodiments, $R^B$ is $C_1$-$C_6$ haloalkyl (such as —$CH_2F$, —$CHF_2$, —$CF_3$, —$CH_2CF_3$, and —$CF_2Cl$). In some further embodiments, $R^B$ is $C_1$-$C_6$ alkylamino (e.g., —NH($C_1$-$C_4$ alkyl) and —N($C_1$-$C_4$ alkyl)$_2$ such as methylamino, dimethylamino, ethylamino, diethylamino, n-propylamino, di-n-propylamino, isopropylamino, diisopropylamino, methylethylamino, or methyl-isopropylamino). In some such embodiments, $R^B$ is optionally substituted amino($C_1$-$C_6$ alkyl) (e.g., —$(CH_2)_{1-3}$—NH($C_1$-$C_4$ alkyl) or —$(CH_2)_{1-3}$—N($C_1$-$C_4$ alkyl)$_2$). In some further embodiments, $R^B$ is a heterocyclyl optionally substituted with one or more $R^9$ (e.g., a four, five or six-membered monocyclic heterocyclyl group containing one or two heteroatoms (e.g., N, O or S), optionally substituted with one or more $R^9$). In some further embodiments, the heterocyclyl is a 5 or 6 membered monocyclic heterocyclyl group, such as pyrrolidine, piperidine, piperazine, or morpholine, for example,

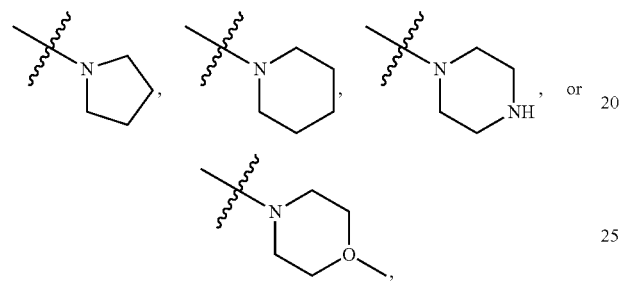

each optionally substituted with one or two $R^9$ (such as methyl, ethyl, and isopropyl). In some further embodiments, the heterocyclyl of $R^B$ is N—($C_1$-$C_6$ alkyl)heterocyclyl, such as

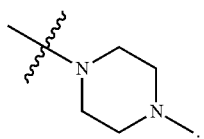 [SMILES: *N1CCN(C)CC1]

In some further embodiments, $R^B$ is heterocyclyl($C_1$-$C_6$ alkyl) optionally substituted with one or more $R^9$ (e.g., the heterocyclyl portion may be a four, five or six-membered monocyclic heterocyclyl group containing one or two heteroatoms (e.g., N, O, or S), optionally substituted with one or more $R^9$). Non-limiting examples of the heterocyclyl($C_1$-$C_6$ alkyl) of the $R^B$ substituent includes

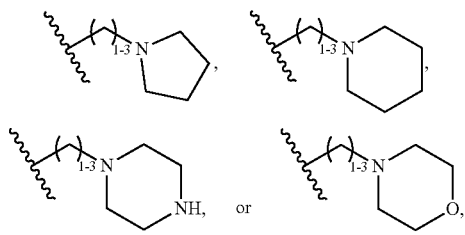

each optionally substituted with one or two $R^9$ (such as methyl, ethyl, and isopropyl). When the heterocyclyl or the heterocyclyl portion of the heterocyclyl($C_1$-$C_6$ alkyl) contains a secondary amine moiety, the nitrogen atom of such amine moiety may be substituted with $R^9$ (e.g.,

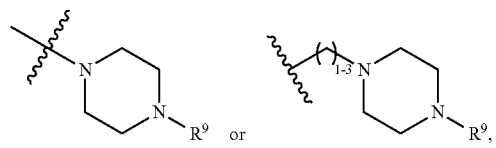

where $R^9$ is $C_1$-$C_6$ alkyl such as methyl, ethyl, or isopropyl). In some further embodiments, Ring B is a phenyl substituted with $C_3$-$C_7$ cycloalkyl or $C_3$-$C_7$ cycloalkyl($C_1$-$C_6$ alkyl). Non-limiting examples of the of the $C_3$-$C_7$ cycloalkyl or $C_3$-$C_7$ cycloalkyl($C_1$-$C_6$ alkyl) of the $R^B$ substituent include

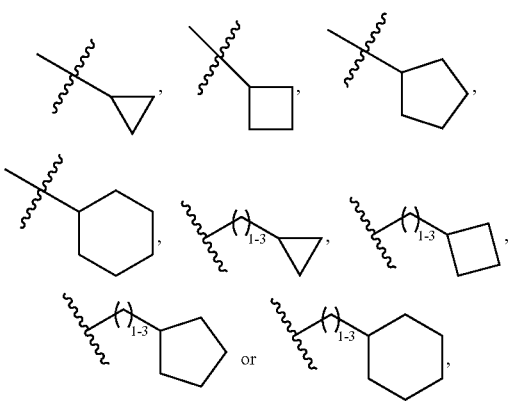

each optionally substituted with one or more $R^9$ (where $R^9$ is halogen, $C_1$-$C_6$ alkyl, or $C_1$-$C_6$ haloalkyl (e.g., trifluoromethyl)). In some further embodiments, each $R^B$ is independently fluoro, chloro, methyl, ethyl, n-propyl, isopropyl, tert-butyl, trifluoromethyl, trifluoromethoxy, —NH($C_1$-$C_4$ alkyl) (such as —NH(Me) and —NH(Et)), —N($C_1$-$C_4$ alkyl)$_2$ (such as

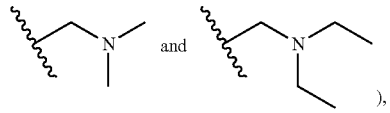

),

—$(CH_2)_{1-3}$—NH($C_1$-$C_4$ alkyl), —$(CH_2)_{1-3}$—N($C_1$-$C_4$ alkyl)$_2$,

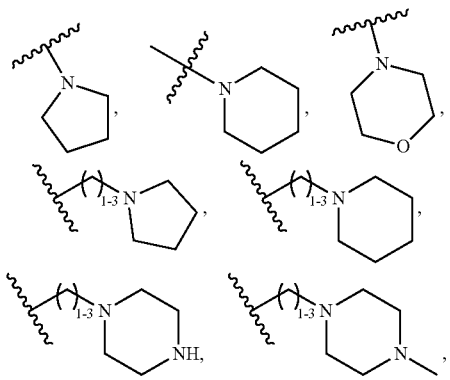

-continued

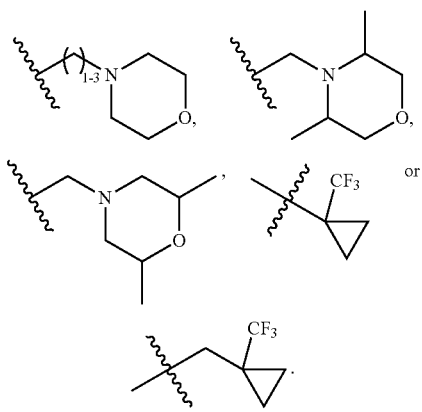

In some embodiments, Ring B is a phenyl or pyridyl substituted with one $R^B$, wherein $R^B$ is $C_1$-$C_6$ alkyl,

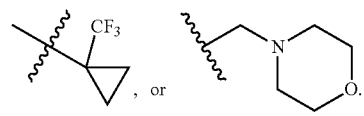 [SMILES: *C1(C(F)(F)F)CC1 ; *CN1CCOCC1]

In some embodiments, Ring B is a phenyl or pyridyl substituted with two $R^B$, wherein one $R^B$ is $C_1$-$C_6$ alkyl or halogen; and the other $R^B$ is halogen, —NH($C_1$-$C_4$ alkyl), —N($C_1$-$C_4$ alkyl)$_2$, —(CH$_2$)—NH($C_1$-$C_4$ alkyl), —(CH$_2$)—N($C_1$-$C_4$ alkyl)$_2$,

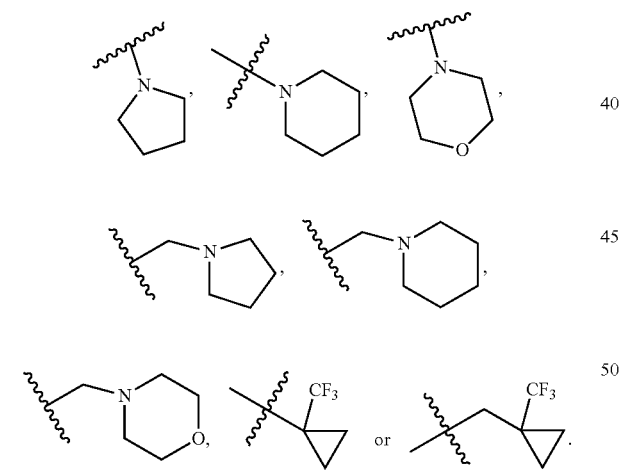

In some embodiments, when Ring B is a phenyl substituted with one $R^B$ described herein; $R^B$ is at the para position

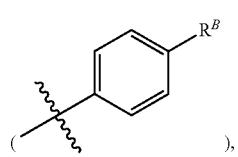

or at a meta position

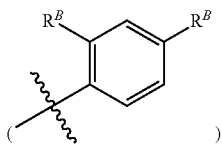

In some embodiments, when Ring B is a phenyl substituted with two $R^B$ described herein; one of the $R^B$ substituent is at the para position; and the other $R^B$ substituent is at the ortho

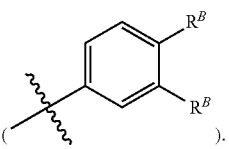

or meta position

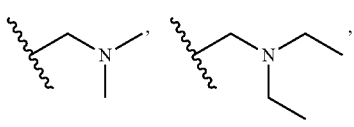

In some other embodiments, Ring B is naphthyl substituted with one, two or three $R^B$ described herein. In some embodiments, each $R^B$ is independently halogen, optionally substituted $C_1$-$C_6$ alkyl, $C_1$-$C_6$ haloalkyl, $C_1$-$C_6$ alkylamino, amino($C_1$-$C_6$ alkyl), $C_3$-$C_7$ cycloalkyl optionally substituted with one or more $R^9$, $C_3$-$C_7$ cycloalkyl($C_1$-$C_6$ alkyl) optionally substituted with one or more $R^9$, heterocyclyl optionally substituted with one or more $R^9$ (e.g., optionally substituted with $C_1$-$C_6$ alkyl or halogen), or heterocyclyl($C_1$-$C_6$ alkyl) optionally substituted with one or more $R^9$ (e.g., optionally substituted with $C_1$-$C_6$ alkyl or halogen). In some embodiments, $R^B$ is halogen, $C_1$-$C_6$ alkyl, $C_1$-$C_6$ haloalkyl, $C_1$-$C_6$ alkylamino, unsubstituted heterocyclyl, heterocyclyl substituted with $C_1$-$C_6$ alkyl, unsubstituted heterocyclyl($C_1$-$C_6$ alkyl), or heterocyclyl($C_1$-$C_6$ alkyl) substituted with $C_1$-$C_6$ alkyl. In some further embodiments, Ring B is substituted with one, two, or three substituents independently selected from the group consisting of fluoro, chloro, methyl, ethyl, n-propyl, isopropyl, trifluoromethyl, —NH(Me), —NH(Et), —N(Me)$_2$, —N(Et)$_2$,

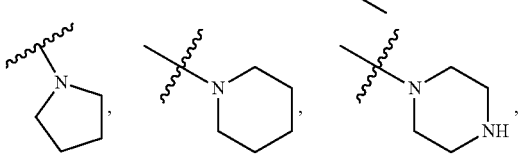

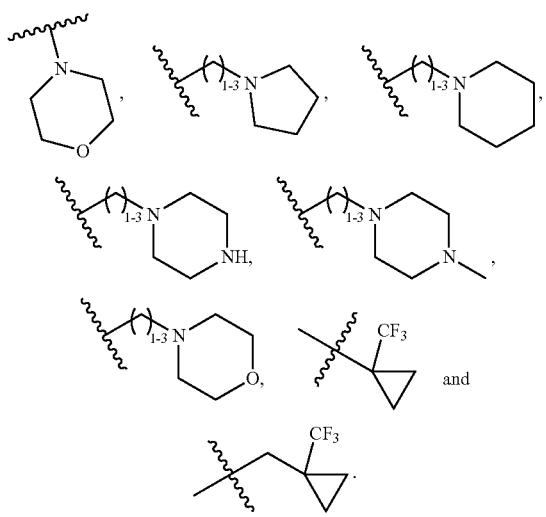

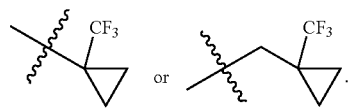 [SMILES: *C1(C(F)(F)F)CC1 ; *CC1(C(F)(F)F)CC1]

Some additional embodiments are compounds of Formula (Ia) through (Ii) as described herein, or a pharmaceutically acceptable salt of any of the foregoing. In some embodiments, Q is C=O. In other embodiments, Q is CH$_2$. In some embodiments, R$^1$ is H. In some embodiments, R$^2$ is H. In some embodiments, n is 1 or 2. In some embodiments, Ring A is not substituted with any R$^A$. In some embodiment, L is —(CH$_2$)$_{1-3}$—NH—C(=O)—(CH$_2$)$_{1-2}$—NH—*, —NH—C(=O)—(CH$_2$)$_{1-2}$—NH—(CH$_2$)$_{1-3}$—* or —(CH$_2$)$_{1-3}$—NH—C(=O)—(CH$_2$)$_{1-2}$—NH—(CH$_2$)$_{1-3}$—*, wherein * indicates the attachment point to Ring B. In one embodiment, L is —CH$_2$—NH—C(=O)—CH$_2$—NH—*. In some embodiments, Ring B is phenyl or pyridyl each substituted with one or two R$^B$. In some such embodiments, when Ring B is substituted with one R$^B$, R$^B$ is fluoro, chloro, methyl, ethyl, isopropyl, or t-butyl. In some such embodiments, when Ring B is substituted with one R$^B$, such R$^B$ is —N(Me)$_2$, —N(Et)$_2$, —(CH$_2$)$_{1-2}$—N(Me)$_2$, or —(CH$_2$)$_{1-2}$N(Et)$_2$. In some such embodiments, when Ring B is substituted with one R$^B$, such R$^B$ is

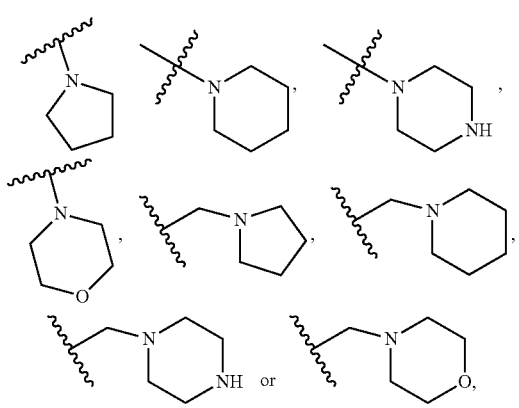

each optionally substituted with one or more R$^9$, for example, C$_1$-C$_6$ alkyl. In some such embodiments, when Ring B is substituted with one R$^B$, such R$^B$ is

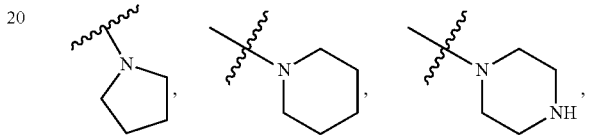

In some such embodiments, when Ring B is substituted with two R$^B$, such R$^B$ are independently fluoro, chloro, methyl, trifluoromethyl, ethyl, isopropyl or t-butyl. In some such embodiments, when Ring B is substituted with two substituents, one such substituent is —N(Me)$_2$, —N(Et)$_2$, —(CH$_2$)$_{1-2}$—N(Me)$_2$, or —(CH$_2$)$_{1-2}$N(Et)$_2$; and the other such substituent is fluoro, chloro, methyl, trifluoromethyl, ethyl, isopropyl or t-butyl. In some such embodiments, when Ring B is substituted with two R$^B$, one such R$^B$ is

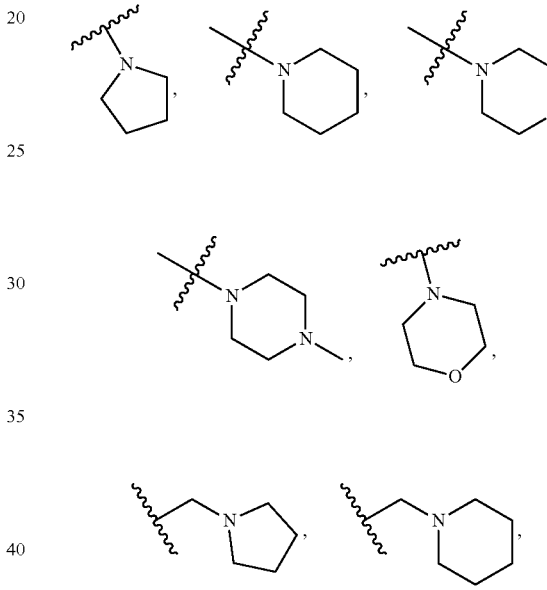

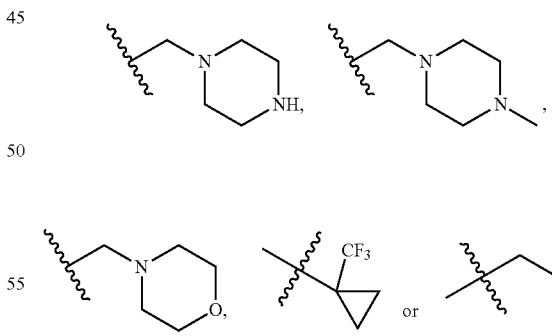

each optionally substituted with one or more R$^9$ (for example, C$_1$-C$_6$ alkyl); and the other such R$^B$ is fluoro, chloro, methyl, trifluoromethyl, ethyl, isopropyl, t-butyl, —N(Me)$_2$, —N(Et)$_2$, —(CH$_2$)$_{1-2}$—N(Me)$_2$, or —(CH$_2$)$_{1-2}$N(Et)$_2$.

In some embodiments, the compound of Formula (I) is selected from Compounds 1-35 of Table A, and pharmaceutically acceptable salts thereof.

TABLE A

Exemplary Compounds of Formula (I)

| COMPD No. | Structure |
|---|---|
| 1 | (structure) |
| 2 | (structure) |
| 3 | (structure) |
| 4 | (structure) |

TABLE A-continued
Exemplary Compounds of Formula (I)
| COMPD No. | Structure |
| --- | --- |
| 5 | 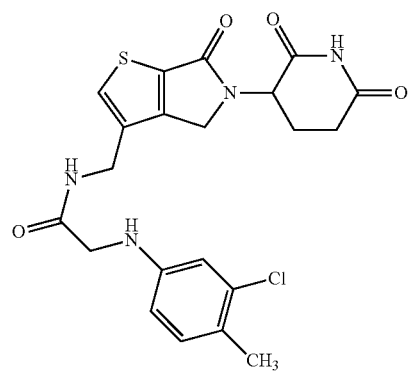 [SMILES: Cc1ccc(NCC(=O)NCc2csc3c2CN(C2CCC(=O)NC2=O)C3=O)cc1Cl] |
| 6 | 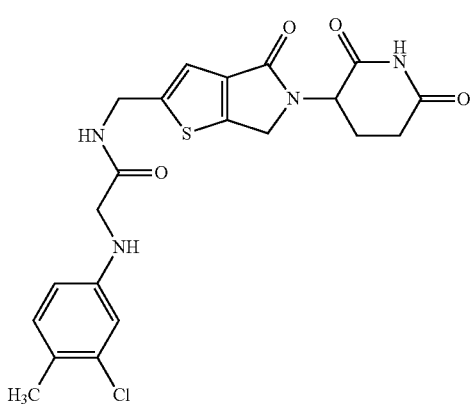 [SMILES: Cc1ccc(NCC(=O)NCc2cc3c(s2)CN(C2CCC(=O)NC2=O)C3=O)cc1Cl] |
| 7 | 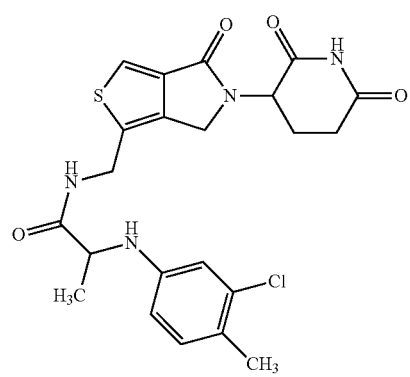 [SMILES: Cc1ccc(NC(C)C(=O)NCc2scc3c2CN(C2CCC(=O)NC2=O)C3=O)cc1Cl] |

TABLE A-continued
Exemplary Compounds of Formula (I)
| COMPD No. | Structure |
|---|---|
| 8 | 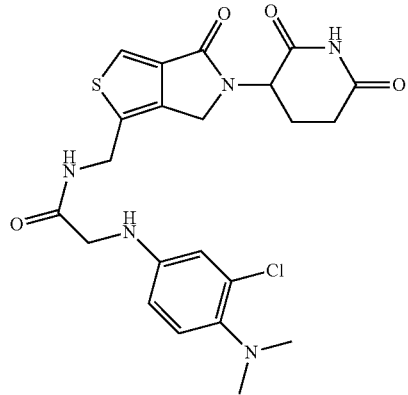 [SMILES: CN(C)c1ccc(NCC(=O)NCc2scc3c2CN(C2CCC(=O)NC2=O)C3=O)cc1Cl] |
| 9 | 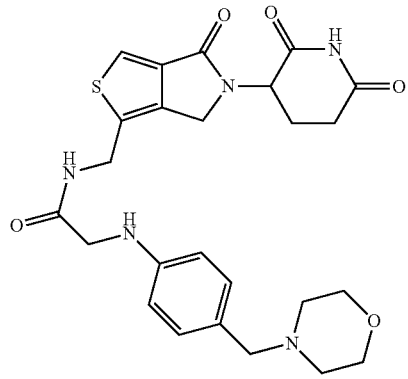 [SMILES: O=C(CNc1ccc(CN2CCOCC2)cc1)NCc1scc2c1CN(C1CCC(=O)NC1=O)C2=O] |
| 10 | 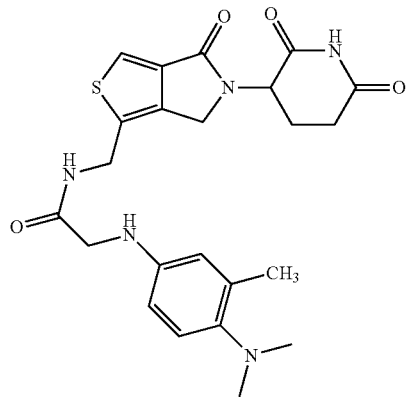 [SMILES: Cc1cc(NCC(=O)NCc2scc3c2CN(C2CCC(=O)NC2=O)C3=O)ccc1N(C)C] |

TABLE A-continued

Exemplary Compounds of Formula (I)

| COMPD No. | Structure |
|---|---|
| 11 | 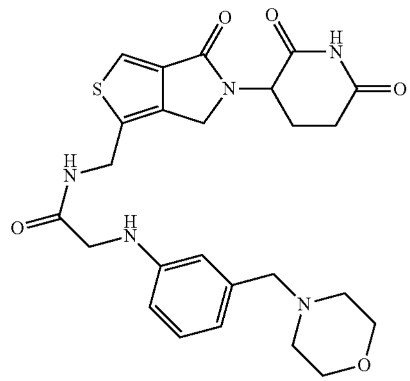 [SMILES: O=C(CNc1cccc(CN2CCOCC2)c1)NCc1scc2c1CN(C1CCC(=O)NC1=O)C2=O] |
| 12 | 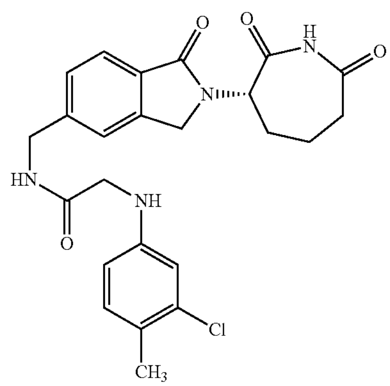 [SMILES: Cc1ccc(NCC(=O)NCc2ccc3c(c2)CN([C@H]2CCCC(=O)NC2=O)C3=O)cc1Cl] |
| 13 | 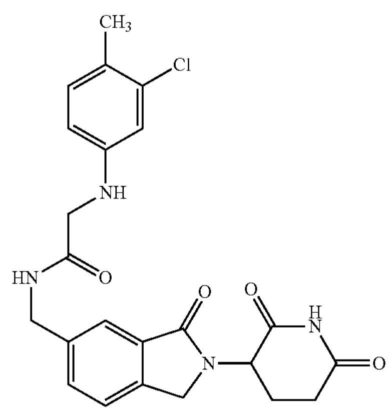 [SMILES: Cc1ccc(NCC(=O)NCc2ccc3c(c2)C(=O)N(C2CCC(=O)NC2=O)C3)cc1Cl] |
| 14 | 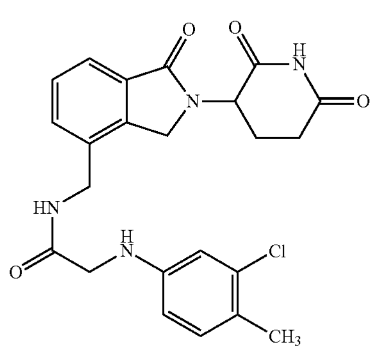 [SMILES: Cc1ccc(NCC(=O)NCc2cccc3c2CN(C2CCC(=O)NC2=O)C3=O)cc1Cl] |

TABLE A-continued

Exemplary Compounds of Formula (I)

| COMPD No. | Structure |
|---|---|
| 15 | 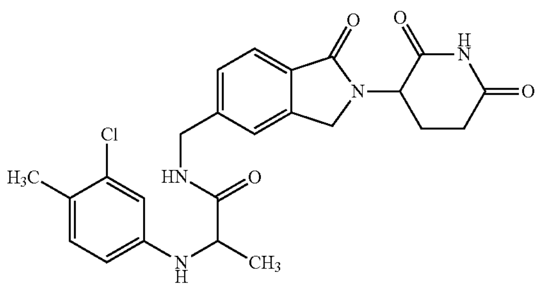 [SMILES: Cc1ccc(NC(C)C(=O)NCc2ccc3c(c2)CN(C2CCC(=O)NC2=O)C3=O)cc1Cl] |
| 16 | 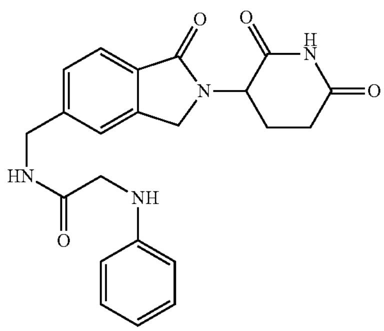 [SMILES: O=C(CNc1ccccc1)NCc1ccc2c(c1)CN(C1CCC(=O)NC1=O)C2=O] |
| 17 | 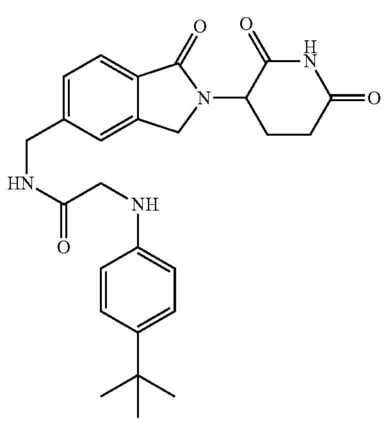 [SMILES: CC(C)(C)c1ccc(NCC(=O)NCc2ccc3c(c2)CN(C2CCC(=O)NC2=O)C3=O)cc1] |
| 18 | 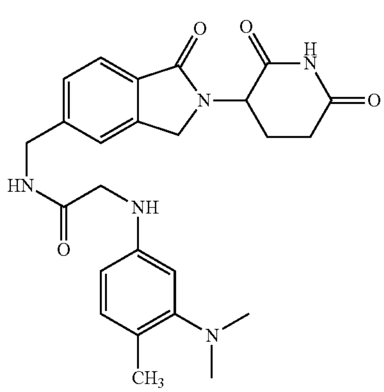 [SMILES: Cc1ccc(NCC(=O)NCc2ccc3c(c2)CN(C2CCC(=O)NC2=O)C3=O)cc1N(C)C] |

TABLE A-continued
Exemplary Compounds of Formula (I)
| COMPD No. | Structure |
|---|---|
| 19 | 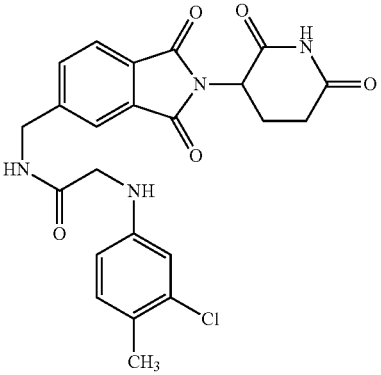 [SMILES: Cc1ccc(NCC(=O)NCc2ccc3c(c2)C(=O)N(C2CCC(=O)NC2=O)C3=O)cc1Cl] |
| 20 | 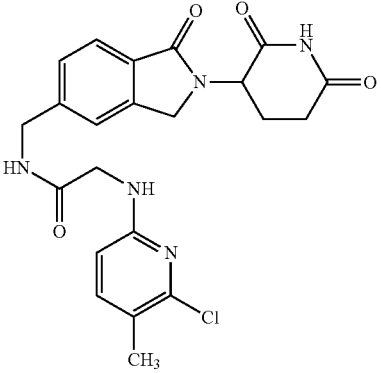 [SMILES: Cc1ccc(NCC(=O)NCc2ccc3c(c2)CN(C2CCC(=O)NC2=O)C3=O)nc1Cl] |
| 21 | 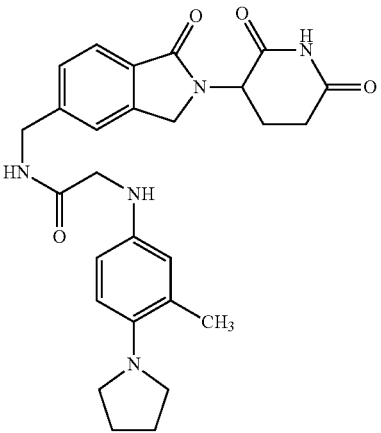 [SMILES: Cc1cc(NCC(=O)NCc2ccc3c(c2)CN(C2CCC(=O)NC2=O)C3=O)ccc1N1CCCC1] |

TABLE A-continued
Exemplary Compounds of Formula (I)
| COMPD No. | Structure |
|---|---|
| 22 | 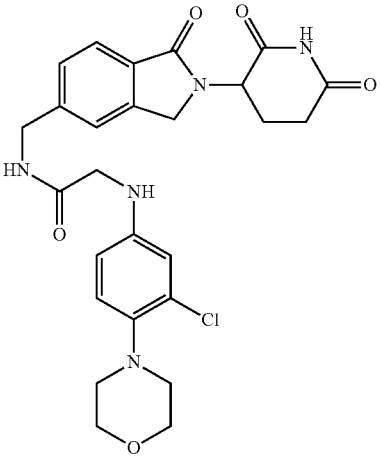 [SMILES: O=C(CNc1ccc(N2CCOCC2)c(Cl)c1)NCc1ccc2c(c1)CN(C1CCC(=O)NC1=O)C2=O] |
| 23 | 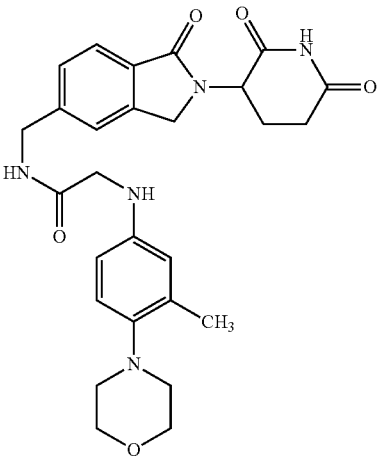 [SMILES: Cc1cc(NCC(=O)NCc2ccc3c(c2)CN(C2CCC(=O)NC2=O)C3=O)ccc1N1CCOCC1] |
| 24 | 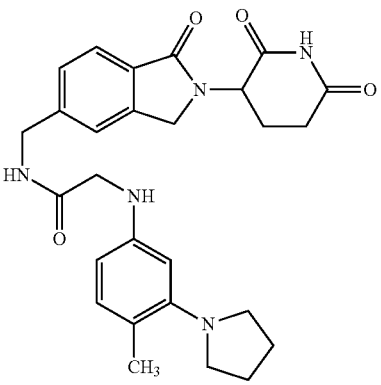 [SMILES: Cc1ccc(NCC(=O)NCc2ccc3c(c2)CN(C2CCC(=O)NC2=O)C3=O)cc1N1CCCC1] |

TABLE A-continued

Exemplary Compounds of Formula (I)

| COMPD No. | Structure |
|---|---|
| 25 | 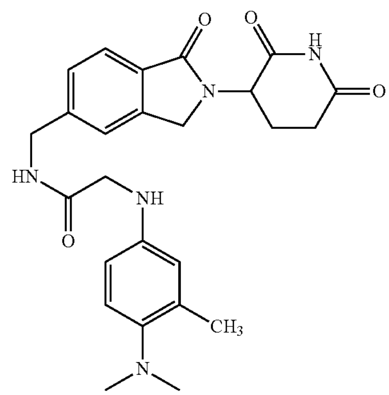 [SMILES: Cc1cc(NCC(=O)NCc2ccc3c(c2)CN(C2CCC(=O)NC2=O)C3=O)ccc1N(C)C] |
| 26 | 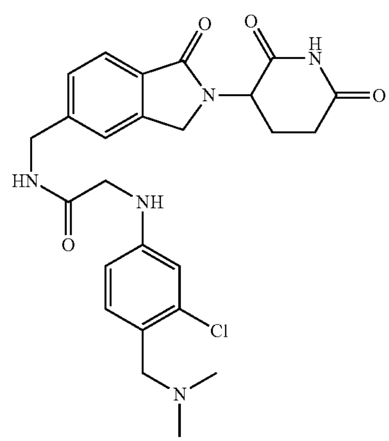 [SMILES: CN(C)Cc1ccc(NCC(=O)NCc2ccc3c(c2)CN(C2CCC(=O)NC2=O)C3=O)cc1Cl] |
| 27 | 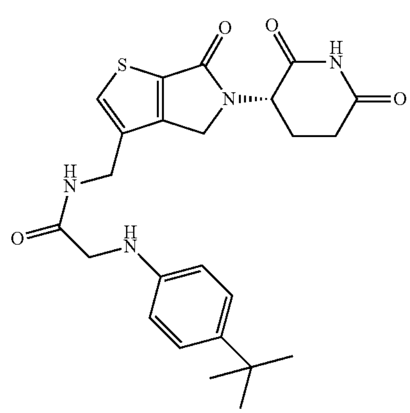 [SMILES: CC(C)(C)c1ccc(NCC(=O)NCc2csc3c2CN([C@H]2CCC(=O)NC2=O)C3=O)cc1] |

TABLE A-continued
Exemplary Compounds of Formula (I)
| COMPD No. | Structure |
|---|---|
| 28 | 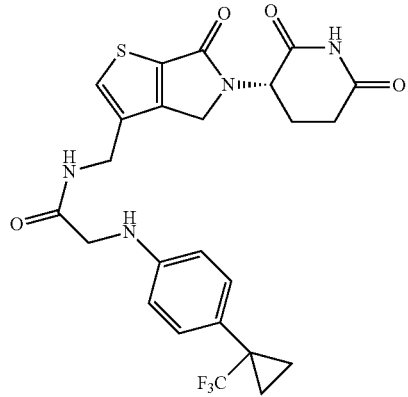 [SMILES: O=C(CNc1ccc(C2(C(F)(F)F)CC2)cc1)NCc1csc2c1CN([C@H]1CCC(=O)NC1=O)C2=O] |
| 29 | 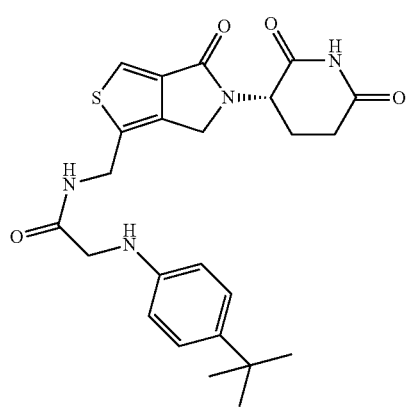 [SMILES: CC(C)(C)c1ccc(NCC(=O)NCc2scc3c2CN([C@H]2CCC(=O)NC2=O)C3=O)cc1] |
| 30 | 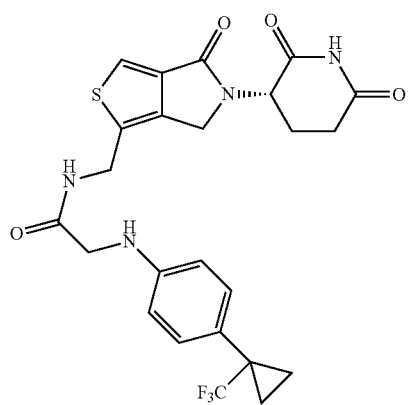 [SMILES: O=C(CNc1ccc(C2(C(F)(F)F)CC2)cc1)NCc1scc2c1CN([C@H]1CCC(=O)NC1=O)C2=O] |

TABLE A-continued
Exemplary Compounds of Formula (I)
| COMPD No. | Structure |
|---|---|
| 31 | 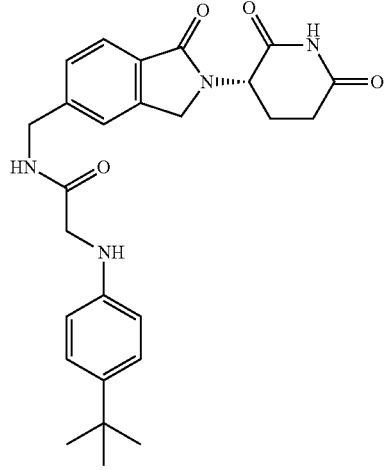 [SMILES: CC(C)(C)c1ccc(NCC(=O)NCc2ccc3c(c2)CN([C@H]2CCC(=O)NC2=O)C3=O)cc1] |
| 32 | 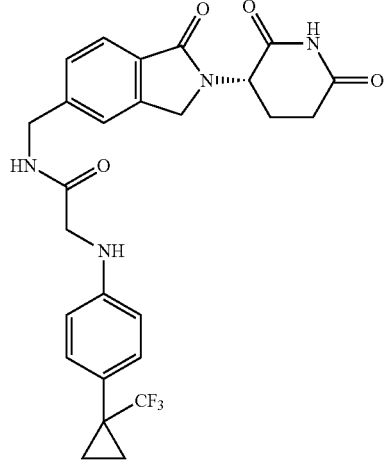 [SMILES: O=C(CNc1ccc(C2(C(F)(F)F)CC2)cc1)NCc1ccc2c(c1)CN([C@H]1CCC(=O)NC1=O)C2=O] |
| 33 | 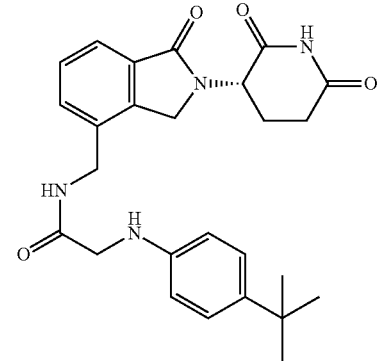 [SMILES: CC(C)(C)c1ccc(NCC(=O)NCc2cccc3c2CN([C@H]2CCC(=O)NC2=O)C3=O)cc1] |

TABLE A-continued

Exemplary Compounds of Formula (I)

| COMPD No. | Structure |
|---|---|
| 34 | 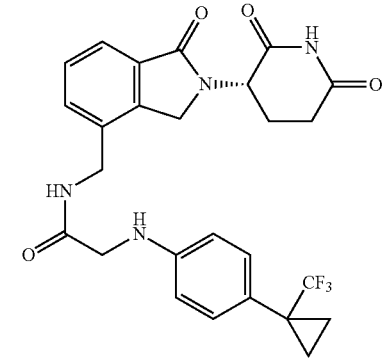 [SMILES: O=C(CNc1ccc(C2(C(F)(F)F)CC2)cc1)NCc1cccc2c1CN([C@H]1CCC(=O)NC1=O)C2=O] |
| 35 | 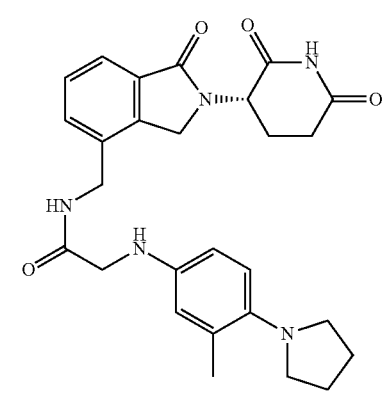 [SMILES: Cc1cc(NCC(=O)NCc2cccc3c2CN([C@H]2CCC(=O)NC2=O)C3=O)ccc1N1CCCC1] |

Some embodiments provide a pharmaceutical composition, comprising a compound of Formula (I), (Ia), (Ib), (Ic), (Id), (Ie), (If), (Ig), (Ih), or (Ii), or a pharmaceutically acceptable salt thereof, and at least one pharmaceutically acceptable carrier or excipient.

In any embodiments of the compounds described herein, when a substituent is selected from a carbocyclyl (e.g., $C_3$-$C_8$ carbocyclyl), the carbocyclyl includes $C_3$-$C_8$ cycloalkyl. When a substituent is select from 3 to 7 membered heterocyclyl, the heterocyclyl includes 3 to 7 membered monocyclic heterocycle rings with no double or triple bond within the ring structure.

In some embodiments, the compound of Formula (I) (including Formulae (Ia)-(Ii)) is formed as a pharmaceutically acceptable salt. In some embodiments, the pharmaceutically acceptable salt is a trifluoroacetic acid salt. In some embodiments, the compound of Formula (I) (including Formulae (Ia)-(Ii)), or a pharmaceutically acceptable salt thereof, is racemic. In some embodiments, the compound of Formula (I) (including Formulae (Ia)-(Ii)), or a pharmaceutically acceptable salt thereof, has an S-configuration or a R-configuration (for example, at the carbon atom with an asterisk:

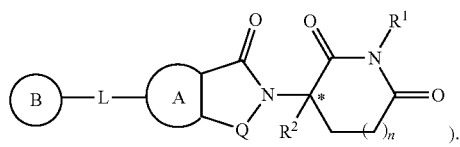

In some embodiments, the compound of Formula (I) (including Formulae (Ia)-(Ii), or a pharmaceutically acceptable salt thereof, is enriched in one enantiomer over another enantiomer, for example, enriched by about 10%, 20%, 30%, 40%, 50%, 60%, 70%, 80%, 90%, 95%, or 99%, or a range defined by any two preceding values. In some embodiments, the compound of Formula (I) (including Formulae (Ia)-(Ii)) or a pharmaceutically acceptable salt thereof, is enriched in one diastereomer over another diastereomer for example, enriched by about 10%, 20%, 30%, 40%, 50%, 60%, 70%, 80%, 90%, 95%, or 99%, or a range defined by any two preceding values. In some embodiments, the compound of Formula (I) (including Formulae (Ia)-(Ii)) is a pharmaceutically acceptable solvate.

Methods of Treatment/Uses

Some embodiments provide a method of modulating the activity of a protein in a biological sample, comprising contacting the biological sample with a compound of Formula (I) (including (Ia), (Ib), (Ic), (Id), (Ie), (If), (Ig), (Ih), or (Ii), or a pharmaceutically acceptable salt thereof; wherein the protein is IL-1β, IL-2, IL-6, TNFα, CK1α, GSPT1, aiolos, ikaros, or helios, or combinations thereof. Some embodiments provide the use of a compound of Formula (I) (including (Ia), (Ib), (Ic), (Id), (Ie), (If), (Ig), (Ih), or (Ii)), or a pharmaceutically acceptable salt thereof, for modulating the activity of a protein in a biological sample, comprising contacting the biological sample with a compound of Formula (I) (including (Ia), (Ib), (Ic), (Id), (Ie), (If), (Ig), (Ih), or (Ii)) or a pharmaceutically acceptable salt thereof; wherein the protein is IL-1β, IL-2, IL-6, TNFα, CK1α, GSPT1, aiolos, ikaros, or helios, or combinations thereof. In some embodiments, the protein is wild-type. In other embodiments, the protein is a mutant form of the protein. In some embodiments, the protein is overexpressed. In some aspect, the method or use inhibits the activity of the protein. In another aspect, the method of use induce the activity of the protein, for example, IL-2. In some embodiments, the biological sample contains one or more cancer cells. In some embodiments, the cells are small cell lung cancer cells, non-small cell lung cancer cells, breast cancer cells, prostate cancer cells, head and neck cancer cells, pancreatic cancer cells, colon cancer cells, rectal cancer cells, teratoma cells, gastric cancer cells, ovarian cancer cells, endometrial cancer cells, brain cancer cells, retinoblastoma cells, leukemia cells, skin cancer cells, melanoma cells, squamous cell carcinoma cells, liposarcoma cells, lymphoma cells, multiple myeloma cells, testicular cancer cells, liver cancer cells, esophageal cancer cells, kidney carcinoma cells, astrogliosis cells, relapsed/refractory multiple myeloma cells, or neuroblastoma cells.

Some embodiments provide a method of treating, ameliorating, or preventing a disease, disorder, or condition associated with a protein in a subject, the protein is IL-1β, IL-2, IL-6, TNFα, CK1α, GSPT1, aiolos, ikaros, or helios, or combinations of any of the foregoing; the method comprising administering a therapeutically effective amount of a compound of Formula (I) (including (Ia), (Ib), (Ic), (Id), (Ie), (If), (Ig), (Ih), or (Ii)), or a pharmaceutically acceptable salt thereof, or a pharmaceutical composition thereof to the subject; wherein the disease, disorder, or condition is a hematological malignancy or a solid tumor. Some embodiments provide the use of a compound of Formula (I) (i including (Ia), (Ib), (Ic), (Id), (Ie), (If), (Ig), (Ih), or (Ii)), or a pharmaceutically acceptable salt thereof, or a pharmaceutical composition thereof for treating, ameliorating, or preventing a disease, disorder, or condition associated with a protein; wherein the protein is IL-1β, IL-2, IL-6, TNFα, CK1α, GSPT1, aiolos, ikaros, or helios, combinations of any of the foregoing; and wherein the disease, disorder, or condition is a hematological malignancy or a solid tumor. In some embodiments, the protein is wild-type. In other embodiments, the protein is a mutant form of the protein. In some embodiments, the protein is overexpressed.

Some other embodiments provide a method of treating, ameliorating, or preventing a hematological malignancy or a solid tumor in a subject, comprising administering a therapeutically effective amount of a compound of Formula (I) (including (Ia), (Ib), (Ic), (Id), (Ie), (If), (Ig), (Ih), or (Ii)), or a pharmaceutically acceptable salt thereof, or a pharmaceutical composition thereof to the subject. Some embodiments provide the use of a compound of Formula (I) (including (Ia), (Ib), (Ic), (Id), (Ie), (If), (Ig), (Ih), or (Ii), or a pharmaceutically acceptable salt thereof, or a pharmaceutical composition thereof for treating, ameliorating, or preventing a hematological malignancy or a solid tumor. In some embodiments, the hematological malignancy or the solid tumor is associated with a protein, wherein the protein is IL-1β, IL-2, IL-6, TNFα, CK1α, GSPT1, aiolos, ikaros, or helios, combinations of any of the foregoing. In some embodiments, the protein is wild-type. In other embodiments, the protein is a mutant form of the protein. In some embodiments, the protein is overexpressed.

In some embodiments of the methods or uses described herein, the hematological malignancy or a solid tumor is small cell lung cancer, non-small cell lung cancer, breast cancer, prostate cancer, head and neck cancer, pancreatic cancer, colon cancer, rectal cancer, teratoma, gastric cancer, ovarian cancer, endometrial cancer, brain cancer, retinoblastoma, leukemia, skin cancer, melanoma, squamous cell carcinoma, liposarcoma, lymphoma, multiple myeloma, testicular cancer, liver cancer, esophageal cancer, kidney carcinoma, astrogliosis, relapsed/refractory multiple myeloma, or neuroblastoma. In some further embodiments, the hematological malignancy is leukemia, lymphoma, or multiple myeloma.

Some additional embodiments provide a method of treating, ameliorating, or preventing a disease, disorder, or condition associated with a protein in a subject, the protein is IL-1β, IL-2, IL-6, TNFα, CK1α, GSPT1, aiolos, ikaros, or helios, or combinations of any of the foregoing; the method comprising administering a therapeutically effective amount of a compound of Formula (I) (including (Ia), (Ib), (Ic), (Id), (Ie), (If), (Ig), (Ih), or (Ii)), or a pharmaceutically acceptable salt thereof, or a pharmaceutical composition thereof to the subject; wherein the disease, disorder, or condition is a neurodegenerative disease, fibrosis, lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, or chronic obstructive pulmonary disease. In some further embodiments, the neurodegenerative disease may include multiple sclerosis, Alzheimer's disease, Parkinson's disease and other chronic inflammatory diseases of the central nervous system. In some further embodiments, fibrosis may include renal fibrosis, pulmonary fibrosis, and hepatic fibrosis. Some embodiments provide the use of a compound of Formula (I) (including (Ia), (Ib), (Ic), (Id), (Ie), (If), (Ig), (Ih), or (Ii)), or a pharmaceutically acceptable salt thereof, or a pharmaceutical composition thereof for treating, ameliorating, or preventing a disease, disorder, or condition associated with a protein; wherein the protein is IL-1β, IL-2, IL-6, TNFα, CK1α, GSPT1, aiolos, ikaros, or helios, or combinations of any of the foregoing; and wherein the disease, disorder, or condition is a neurodegenerative disease, fibrosis, lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, or chronic obstructive pulmonary disease. In some embodiments, the disease, disorder, or condition is multiple sclerosis, Alzheimer's disease, Parkinson's disease, lupus, fibromyalgia, rheumatoid arthritis, osteoarthritis, ankylosing spondylitis, psoriasis, psoriatic arthritis, Crohn's disease, or ulcerative colitis. In some embodiments, the protein is wild-type. In other embodiments, the protein is a mutant form of the protein. In some embodiments, the protein is overexpressed.

Some embodiments provide a method of treating, ameliorating, or preventing an inflammatory disease, disorder or condition in a subject, comprising administering a therapeutically effective amount of a compound of Formula (I) (including (Ia), (Ib), (Ic), (Id), (Ie), (If), (Ig), (Ih), or (Ii)), or a pharmaceutically acceptable salt thereof, or a pharmaceutical composition thereof to the subject. Some embodiments provide the use of a compound of Formula (I) (including (Ia), (Ib), (Ic), (Id), (Ie), (If), (Ig), (Ih), or (Ii), or a pharmaceutically acceptable salt thereof, or a pharmaceutical composition thereof for treating, ameliorating, or preventing an inflammatory disease, disorder or condition. In some embodiments, the inflammatory disease, disorder or condition is a neurodegenerative disease (such as multiple sclerosis, Alzheimer's disease, Parkinson's disease), fibrosis (such as pulmonary fibrosis), lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, or chronic obstructive pulmonary disease. In some embodiments, the inflammatory disease, disorder or condition is associated with a protein, wherein the protein is IL-1β, IL-2, IL-6, TNFα, CK1α, GSPT1, aiolos, ikaros, or helios, combinations of any of the foregoing. In some embodiments, the protein is wild-type. In other embodiments, the protein is a mutant form of the protein. In some embodiments, the protein is overexpressed.

Additional Therapeutic Agents

Some embodiments provide pharmaceutical compositions comprising a compound of Formula (I) (including (Ia), (Ib), (Ic), (Id), (Ie), (If), (Ig), (Ih), or (Ii)) or a pharmaceutically acceptable salt of any of the foregoing and a second therapeutic agent. In some embodiments, the second therapeutic agent is an anti-inflammatory agent. In some embodiments, the second therapeutic agent is a non-steroidal anti-inflammatory agent. In some embodiments, the second therapeutic agent is an anti-cancer agent. In some embodiments, the second therapeutic agent is an immunostimulatory agent. In some embodiments, the second therapeutic agent is an immunosuppressive agent. In some embodiments, the second therapeutic agent is an antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone. In some embodiments, the second therapeutic agent is mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; or oxaliplatin. In some embodiments, the second therapeutic agent is vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; or teniposide. In some embodiments, the second therapeutic agent is actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; or procarbazine. In some embodiments, the second therapeutic agent is cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; or floxuridine. In some embodiments, the second therapeutic agent is azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; or triethylenemelamine. In some embodiments, the second therapeutic agent is nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; or eribulin. In some embodiments, the second therapeutic agent is azathioprine; mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; kelixmab; zanolimumab; efalizumab; erlizumab; obinutuzumab; rituximab; or ocrelizumab. In some embodiments, the second therapeutic agent is pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; rovelizumab; siplizumab; talizumab; telimomab; vapaliximab; vepalimomab; abatacept; belatacept; pegsunercept; aflibercept; alefacept; or rilonacept.

Dosing Regimes

In some embodiments, about 1 mg to about 5 grams, or any amount in between, of a compound of Formula (I) (including (Ia), (Ib), (Ic), (Id), (Ie), (If), (Ig), (Ih), or (Ii)), or a pharmaceutically acceptable salt of any of the foregoing is administered each day, each week, or each cycle of treatment.

In some embodiments, a compound of Formula (I) (including (Ia), (Ib), (Ic), (Id), (Ie), (If), (Ig), (Ih), or (Ii)), or a pharmaceutically acceptable salt of any of the foregoing is administered once per day, twice per day, three times per day, four times per day, or more than four times per day. In some embodiments, a compound of Formula (I) (including (Ia), (Ib), (Ic), (Id), (Ie), (If), (Ig), (Ih), or (Ii)), or a pharmaceutically acceptable salt of any of the foregoing is administered once per day, twice per day, three times per day, four times per day, or more than four times per cycle of treatment.

In some embodiments, each cycle of treatment lasts from 1 day to 14 days, or any value in between. In some embodiments, each cycle of treatment has from at least one day up to fourteen days, or any value in between, between administration. In some embodiments, each cycle of treatment includes one or more additional therapeutic agents, as described herein. In some embodiments, a compound of Formula (I) (including (Ia), (Ib), (Ic), (Id), (Ie), (If), (Ig), (Ih), or (Ii)), or a pharmaceutically acceptable salt of any of the foregoing is provided intravenously over about 10 minutes to over about 4 hours, or any value in between.

Pharmaceutical Compositions

Some embodiments described herein relate to a pharmaceutical composition, that can include an effective amount of one or more compounds described herein (for example, a compound of Formula (I) (including (Ia), (Ib), (Ic), (Id), (Ie), (If), (Ig), (Ih), or (Ii)), or a pharmaceutically acceptable salt thereof) and at least one pharmaceutically acceptable excipient or carrier.

The term "pharmaceutical composition" refers to a mixture of one or more compounds and/or salts disclosed herein with other chemical components, such as one or more excipients. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

As used herein, an "excipient" refers to essentially inert substances that are added to a pharmaceutical composition to provide, without limitation, bulk, consistency, stability, binding ability, lubrication, disintegrating ability etc., to the composition. For example, stabilizers such as anti-oxidants and metal-chelating agents are excipients. Excipients also include ingredients in a pharmaceutical composition that lack appreciable pharmacological activity but may be pharmaceutically necessary or desirable. For example, to increase the bulk of a potent drug whose mass is too small for manufacture and/or administration. It may also be a liquid for the dissolution of a drug to be administered by injection, ingestion or inhalation. For example, a buffered aqueous solution such as, without limitation, phosphate buffered saline that mimics the pH and isotonicity of human blood.

The pharmaceutical compositions described herein can be administered to a human patient per se, or in pharmaceutical compositions where they are mixed with other active ingredients, as in combination therapy, or excipients, or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

One or more of the compounds of preferred embodiments can be provided in the form of pharmaceutically acceptable salts, active metabolites, tautomers, or prodrugs thereof. Some embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound of Formula (I), or a pharmaceutically acceptable salt thereof, can be administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical excipient may also be prepared, placed in an appropriate container, and labeled for treatment of an indicated condition.

EXAMPLES

Additional embodiments are disclosed in further detail in the following schemes, which are not in any way intended to limit the scope of the claims.

Characterization of the compounds disclosed herein is performed with Bruker AV-500 and Bruker DRX-500 NMR spectrometers and a Perkin Elmer PE-SCIEX API-150 mass spectrometer.

General Synthesis
Scheme 1
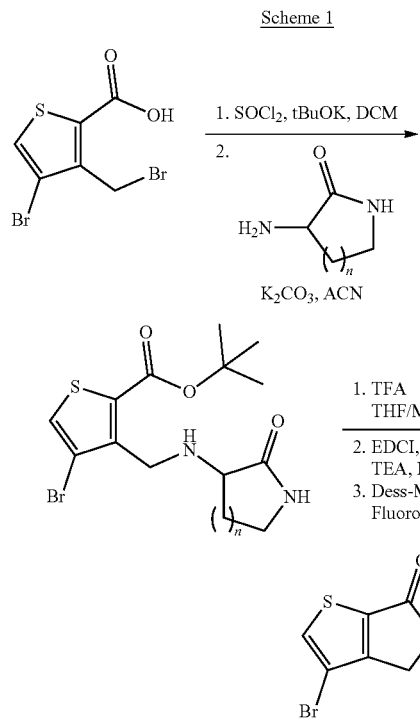
Scheme 2
Scheme 3
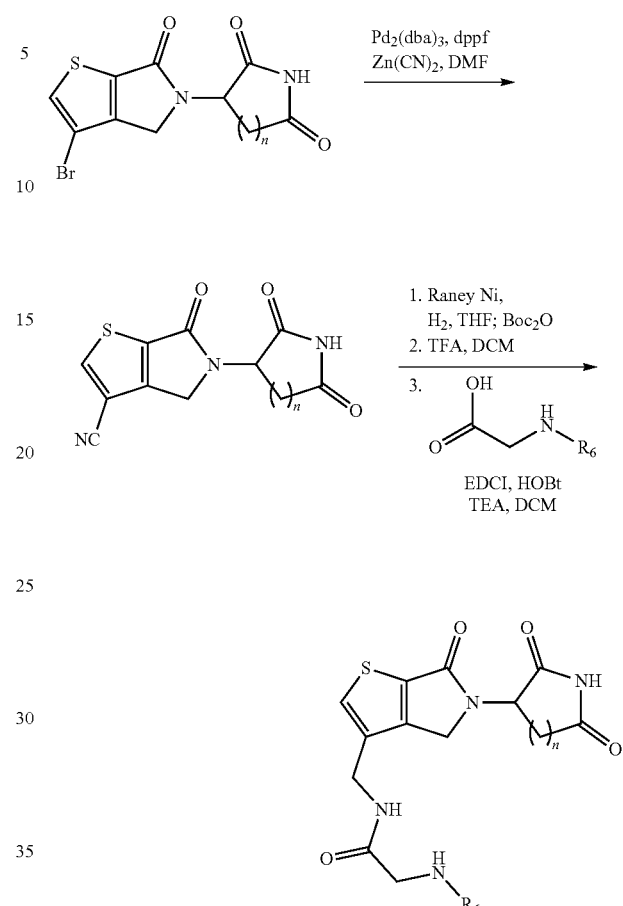
Scheme 4
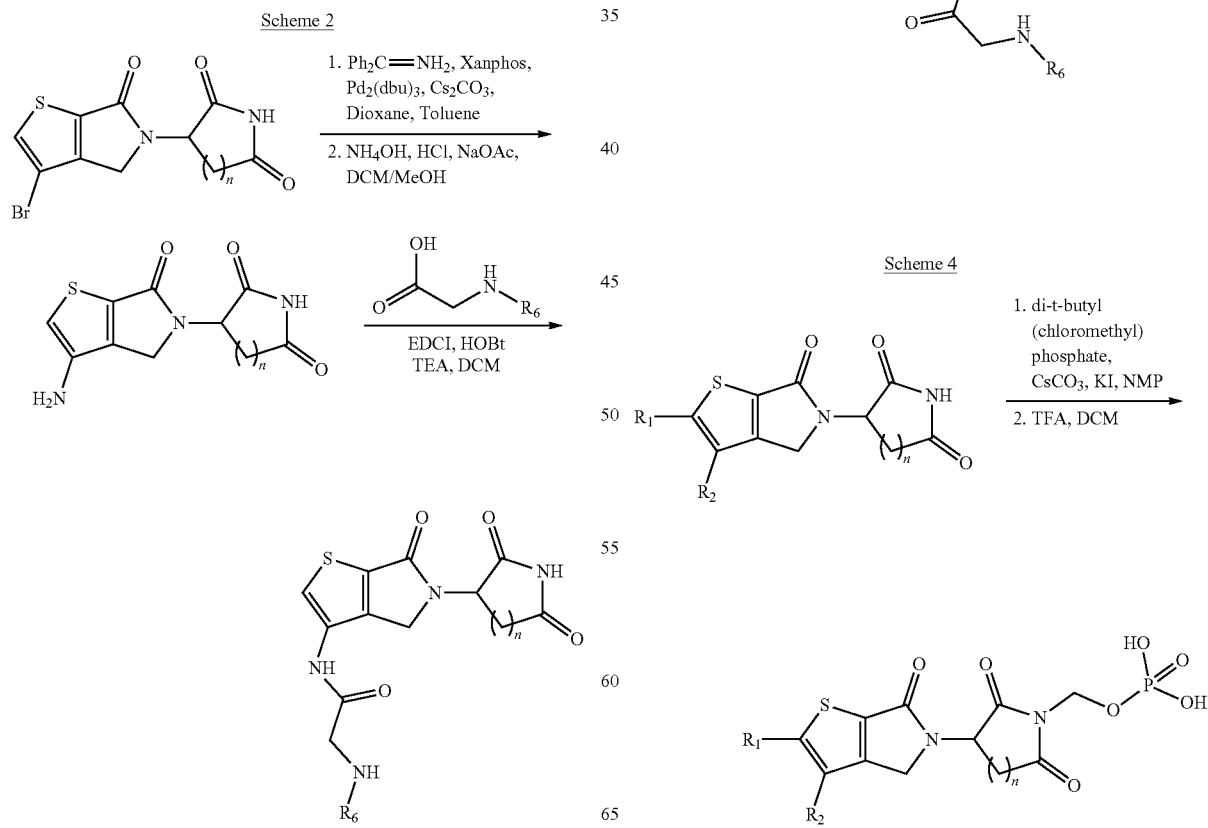

Scheme 5

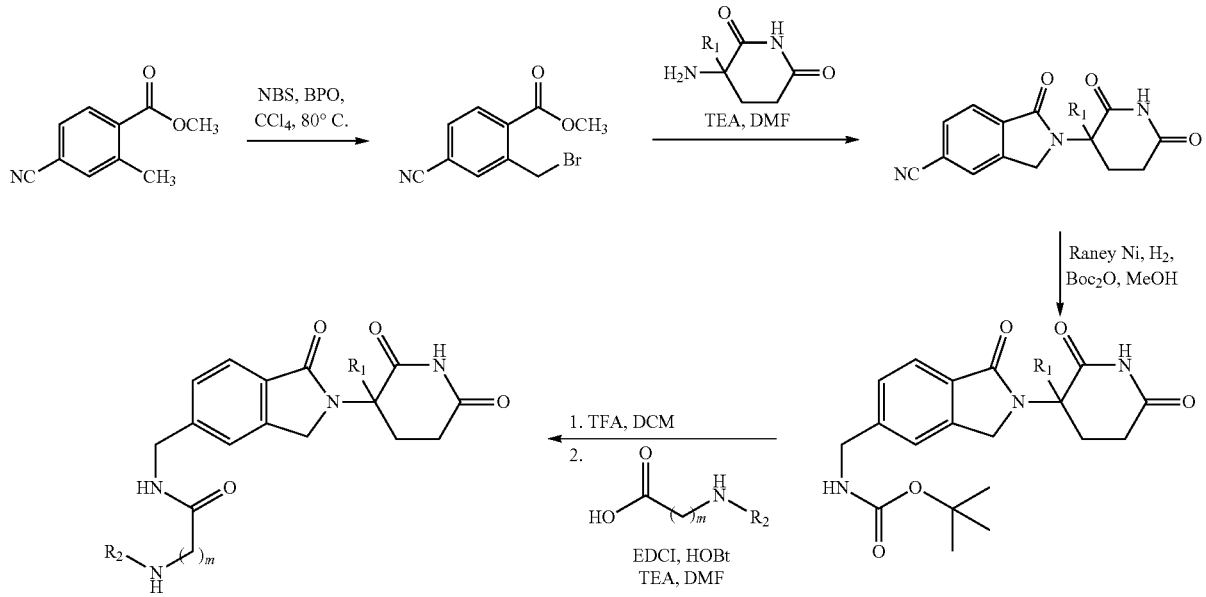

Example 1

Compound 1: 2-((3-Chloro-4-methylphenyl)amino)-N-((2-(2,6-dioxopiperidin-3-yl)-1-oxoisoindolin-5-yl)methyl)acetamide

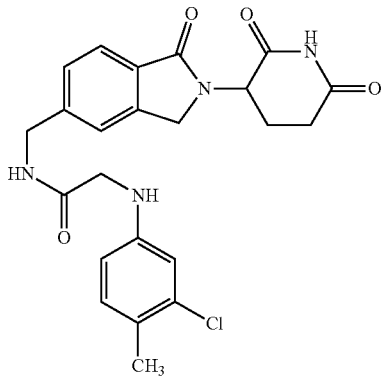 [SMILES: Cc1ccc(NCC(=O)NCc2ccc3c(c2)CN(C2CCC(=O)NC2=O)C3=O)cc1Cl]

To a solution of methyl 5-cyano-2-toluate (5.00 g, 28.6 mmol) in $CCl_4$ (185 mL) at RT was added NBS (5.08 g, 28.6 mmol) followed by benzoyl peroxide (830 mg, 3.43 mmol). The mixture was stirred for 4 h then poured into sat. $NaHCO_3$ (aq.), and the organic layer was separated and concentrated. Ethyl acetate (EA) was added, and the solution was dried over $MgSO_4$ then filtered and concentrated to give methyl 2-(bromomethyl)-4-cyanobenzoate (7.9 g, 100% yield) as a solid. LCMS (ESI) m/z 255 [M+H]$^+$.

To a solution of 3-amino-2,6-piperidinedione HCl (648 mg, 3.94 mmol) in DMF (20 mL) at RT was added TEA (1.21 mL, 8.67 mmol) and stirred for 10 min. The mixture was cooled to 0° C. then a solution of methyl 2-(bromomethyl)-4-cyanobenzoate (1.00 g, 3.94 mmol) in DMF was added dropwise. After 10 min, the reaction was warmed to RT and stirred for 2 days then concentrated. The residue was purified by silica gel chromatography eluting with hexanes/EA (1:1) to hexanes (100%) to give 2-(2,6-dioxo-3-piperidyl)-1-oxo-5-isoindolinecarbonitrile (230 mg, 22% yield) as a solid. LCMS (ESI) m/z 270 [M+H]$^+$.

To a solution of 2-(2,6-dioxo-3-piperidyl)-1-oxo-5-isoindolinecarbonitrile (250 mg, 0.93 mmol) in MeOH (12 mL) at RT was added Boc anhydride (406 mg, 1.86 mmol) followed by Raney Ni (406 mg, 1.86 mmol). The mixture was stirred under $H_2$ for 3 days then filtered and concentrated. The residue was purified by silica gel chromatography eluting with hexanes/EA (1:1) to hexanes (100%) to give 3-{5-[(tert-butoxycarbonylamino)methyl]-2-isoindolinoyl}-2,6-piperidinedione (100 mg, 29% yield) as a solid. LCMS (ESI) m/z 374 [M+H]$^+$.

To a solution of 3-{5-[(tert-butoxycarbonylamino)methyl]-2-isoindolinoyl}-2,6-piperidinedione (100 mg, 0.268 mmol) in DCM (2.5 mL) at RT was added TFA (1 mL). The mixture was stirred for 3.5 h then concentrated and triturated with EA to give 3-[5-(aminomethyl)-2-isoindolinoyl]-2,6-piperidinedione trifluoracetic acid (90 mg, 87% yield) as a solid. The 3-[5-(aminomethyl)-2-isoindolinoyl]-2,6-piperidinedione trifluoracetic acid (50 mg, 0.129 mmol) was dissolved in DMF (1.5 mL) and to this was added HOBT (21 mg, 0.15 mmol) followed by EDCI.HCl (30 mg, 0.15 mmol) and DIEA (112 μL, 0.645 mmol) and (3-chlorotoluidino) acetate acid (44.5 mg, 0.142 mmol) at RT. The mixture was stirred for 7 d then concentrated. The residue was triturated with water then EA to give Compound 1 (15 mg, 25% yield) as a solid. LCMS (ESI) m/z 455 [M+H]$^+$. $^1$H NMR (400 MHz, DMSO-d$_6$) δ 10.98 (s, 1H), 8.54 (dd, 1H), 7.62 (d, 1H), 7.38 (s, 1H), 7.35 (d, 1H), 7.048 (d, 1H), 6.57 (m, 1H), 6.46 (dd, 1H), 6.14 (t, 1H), 5.10 (dd, 1H), 4.30 (m, 4H), 3.71 (d, 1H), 2.92 (m, 1H), 2.59 (m, 1H), 2.40 (m, 1H), 2.00 (m, 1H).

Example 2

Compound 2: 2-((3-chloro-4-methylphenyl)amino)-N-((5-(2,6-dioxopiperidin-3-yl)-4-oxo-5,6-dihydro-4H-thieno[3,4-c]pyrrol-1-yl)methyl)acetamide

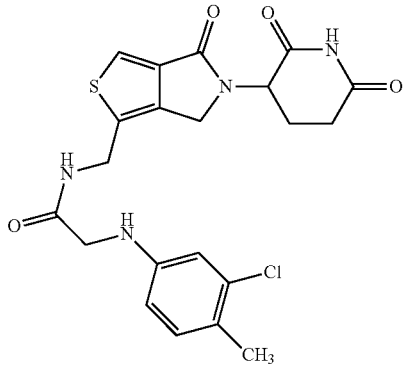 [SMILES: Cc1ccc(NCC(=O)NCc2scc3c2CN(C2CCC(=O)NC2=O)C3=O)cc1Cl]

To a suspension of 3-chloro-4-methylaniline (5.00 g, 35.5 mmol) in acetone (35 mL) was added tert-butyl 2-bromoacetate (6.87 g, 35.5 mmol), K2CO3 (7.30 g, 53.2 mmol) and KI (590 mg, 3.55 mmol). After 18 h, the mixture was concentrated, and the residue was purified using silica gel eluting with PE/EA (3:1) to give tert-butyl 2-((3-chloro-4-methylphenyl)amino)acetate (7.0 g, 78% yield) as an oil. MS (ESI) m/z 256.1 [M+1]+.

To a solution of tert-butyl 2-((3-chloro-4-methylphenyl)amino)acetate (1.00 g, 3.92 mmol) in DCM (8 mL) was added TFA (2 mL). After 3 h, the solution was concentrated to give 2-((3-chloro-4-methylphenyl)amino)acetic acid (380 mg, 48% yield, crude) which was used in the next step without purification. MS (ESI) m/z 200.1 [M+1]+.

To a solution of tert-butyl ((5-(2,6-dioxopiperidin-3-yl)-4-oxo-5,6-dihydro-4H-thieno[3,4-c]pyrrol-1-yl)methyl)carbamate (200 mg, 0.53 mmol) in DCM (3 mL) was added TFA (1 mL). After 5 h, the mixture was concentrated, dried, and dissolved in DCM (4 mL). TEA (107 mg, 1.06 mmol) was added followed by 2-((3-chloro-4-methylphenyl)amino)acetic acid (105 mg, 0.53 mmol) and T3P (402 mg, 1.06 mmol, ≥50 wt. % in EA). After 2 h, the mixture was concentrated, and the residue was purified using prep-TLC eluting with EtOAc to afford Compound 2 (92.1 mg, 30% yield) as a solid. MS (ESI) m/z 461.1 [M+1]+. 1H NMR (400 MHz, DMSO-d6) δ 10.99 (s, 1H), 8.62 (s, 1H), 7.87 (s, 1H), 7.02 (d, J=7.2 Hz, 1H), 6.56 (s, 1H), 6.42 (d, J=7.2 Hz, 1H), 6.15 (s, 1H), 5.01-4.99 (m, 1H), 4.41 (s, 2H), 4.27-4.13 (m, 2H), 3.66 (s, 2H), 2.89-2.86 (m, 1H), 2.60-2.51 (m, 1H), 2.28-2.25 (m, 1H), 2.15 (s, 3H), 1.96 (s, 1H).

Example 3

Compound 3: 2-((3-chloro-4-methylphenyl)amino)-N-((5-(2,6-dioxopiperidin-3-yl)-6-oxo-5,6-dihydro-4H-thieno[2,3-c]pyrrol-2-yl)methyl)acetamide

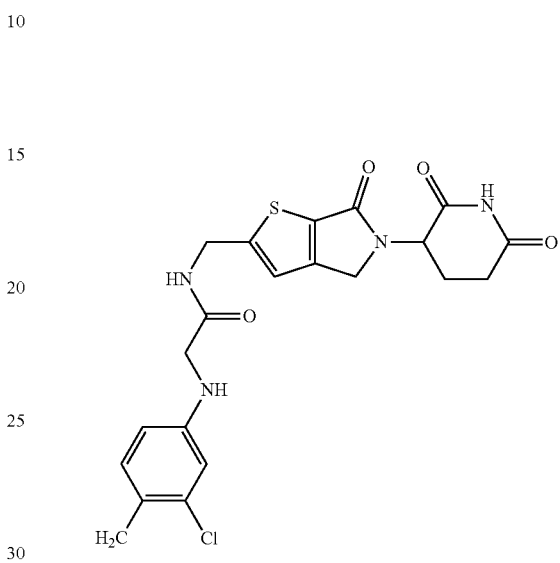

To a solution of tert-butyl ((5-(2,6-dioxopiperidin-3-yl)-6-oxo-5,6-dihydro-4H-thieno[2,3-c]pyrrol-2-yl)methyl)carbamate (80 mg, 0.21 mmol) in DCM (4 mL) at 0° C. was added TFA (2 mL). After 1 h at 0° C., the mixture was concentrated to afford 3-(2-(aminomethyl)-6-oxo-4H-thieno[2,3-c]pyrrol-5(6H)-yl)piperidine-2,6-dione TFA salt (0.21 mmol, crude) which was used in the next step without purification.

To 2-((3-chloro-4-methylphenyl)amino)acetic acid (50 mg, 0.25 mmol) in DMF (4 mL) was added DIEA (54 mg, 0.42 mmol) followed by HOBt (44 mg, 0.32 mmol) and EDAC.HCl (62 mg, 0.32 mmol). After 3 h, 3-(2-(aminomethyl)-6-oxo-4H-thieno[2,3-c]pyrrol-5(6H)-yl)piperidine-2,6-dione TFA salt (0.21 mmol, crude) was added. After 3 h, the mixture was concentrated, and the residue was purified using prep-HPLC (5 μM C18 column, 0.1% TFA in H2O, 0.1% TFA in ACN, 5%-95%) to afford Compound 3 (31.6 mg, 33% yield) as a solid. MS (ESI) m/z 461.1 [M+1]+. 1H NMR (400 MHz, DMSO-d6) δ 10.96 (s, 1H), 8.67 (t, J=6.0 Hz, 1H), 7.05-7.01 (m, 2H) 6.55-6.54 (m, 1H), 6.45-6.43 (m, 1H), 6.17-6.14 (m, 1H), 5.00-4.96 (m, 1H), 5.51 (d, J=5.6 Hz, 2H), 4.34-4.17 (m, 2H), 3.67 (d, J=5.6 Hz, 2H), 2.93-2.84 (m, 1H), 2.60-2.56 (m, 1H), 2.40-2.29 (m, 1H), 2.16 (s, 3H). 2.01-1.96 (m, 1H).

Example 4

Compound 4: 2-((3-(dimethylamino)-4-methylphenyl)amino)-N-((5-(2,6-dioxopiperidin-3-yl)-4-oxo-5,6-dihydro-4H-thieno[3,4-c]pyrrol-1-yl)methyl)acetamide

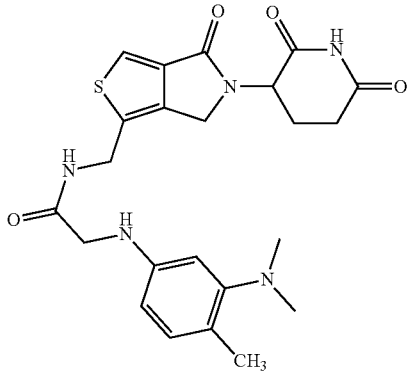 [SMILES: Cc1ccc(NCC(=O)NCc2scc3c2CN(C2CCC(=O)NC2=O)C3=O)cc1N(C)C]

To a suspension of N¹,N¹,6-trimethylbenzene-1,3-diamine (500 mg, 3.33 mmol) in ACN (15 mL) was added tert-butyl 2-bromoacetate (768 mg, 3.99 mmol) and cesium carbonate (1.30 g, 3.99 mmol). After 18 h, the mixture was concentrated, and the residue was purified using silica gel eluting with PE/EA (3:1) to give tert-butyl 2-((3-(dimethylamino)-4-methylphenyl)amino)acetate (650 mg, 74% yield) as an oil. MS (ESI) m/z 265.1[M+1]$^+$.

To a solution of tert-butyl 2-((3-(dimethylamino)-4-methylphenyl)amino)-acetate (650 mg, 2.46 mmol) in DCM (8 mL) was added TFA (2 mL). After 3 h, the mixture was concentrated to afford crude 2-((3-(dimethylamino)-4-methylphenyl)amino)acetic acid (400 mg, 78% yield) which was used in the next step without purification. MS (ESI) m/z 209.1 [M+1]$^+$.

To a solution of tert-butyl ((5-(2,6-dioxopiperidin-3-yl)-4-oxo-5,6-dihydro-4H-thieno[3,4-c]pyrrol-1-yl)methyl)carbamate (73 mg, 0.26 mmol) in DCM (2 mL) was added TFA (1 mL). After 5 h, the mixture was concentrated and dissolved in DCM (2 mL). TEA (78 mg, 0.78 mmol), 2-((3-(dimethylamino)-4-methylphenyl)amino)acetic acid (65 mg, 0.31 mmol), and T3P (197 mg, 0.62 mmol, ≥50 wt. % in EA) were sequentially added. After 2 h, the mixture was concentrated, and the residue was purified using prep-TLC as previously described to afford Compound 4 (20.8 mg, 17% yield) as a solid. MS (ESI) m/z 470.1 [M+1]$^+$. $^1$H NMR (400 MHz, DMSO-$d_6$) δ 11.01 (s, 1H), 8.58 (t, J=6.0 Hz, 1H), 7.86 (s, 1H), 6.82 (d, J=8.0 Hz, 1H), 6.25 (s, 1H), 6.08-6.06 (m, 1H), 5.81 (t, J=6.0 Hz, 1H), 5.01-4.97 (m, 1H), 4.40 (d, J=6.0 Hz, 2H), 4.25-4.12 (m, 2H), 3.61-3.60 (m, 2H), 2.91-2.84 (m, 1H), 2.59 (m, 1H), 2.52-2.50 (m, 6H), 2.26-2.22 (m, 1H), 2.08 (s, 3H), 1.95-1.91 (m, 1H).

Example 5

Compound 5: 2-((3-chloro-4-methylphenyl)amino)-N-((5-(2,6-dioxopiperidin-3-yl)-6-oxo-5,6-dihydro-4H-thieno[2,3-c]pyrrol-3-yl)methyl)acetamide

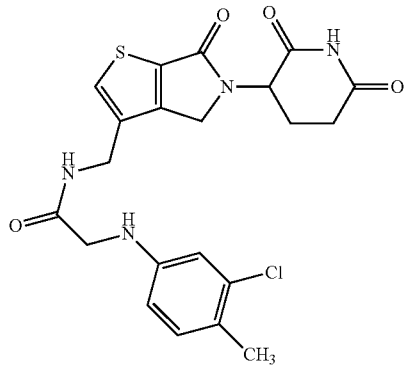 [SMILES: Cc1ccc(NCC(=O)NCc2csc3c2CN(C2CCC(=O)NC2=O)C3=O)cc1Cl]

To a solution of 3-(3-(aminomethyl)-6-oxo-4H-thieno[2,3-c]pyrrol-5(6H)-yl)piperidine-2,6-dione (80 mg, 0.20 mmol) and TEA (51 mg, 0.51 mmol) in DCM (6 mL) was added 2-((3-chloro-4-methylphenyl)amino)acetic acid (48 mg, 0.24 mmol) and T3P (161 mg, 0.51 mmol, ≥50 wt. % in EA). After 2 h, the mixture was concentrated, and the residue was purified using prep-TLC as previously described to afford Compound 5 (26 mg, 28% yield) as a solid. MS (ESI) m/z 461.1 [M+1]$^+$. $^1$H NMR (400 MHz, DMSO-$d_6$) δ 10.97 (s, 1H), 8.45 (t, J=5.6 Hz, 1H), 7.70 (s, 1H), 7.02 (d, J=8.4 Hz, 1H), 6.57 (s, 1H), 6.43 (d, J=8.0 Hz, 1H), 6.09 (t, J=6.0 Hz, 1H), 4.99-4.95 (m, 1H), 4.31-4.16 (m, 4H), 3.67 (d, J=5.6 Hz, 2H), 2.93-2.84 (m, 1H), 2.60-2.50 (m, 1H), 2.26-2.19 (m, 1H), 2.15 (s, 3H), 1.99-1.95 (s, 1H).

Example 6

Compound 6: 2-((3-chloro-4-methylphenyl)amino)-N-((5-(2,6-dioxopiperidin-3-yl)-4-oxo-5,6-dihydro-4H-thieno[2,3-c]pyrrol-2-yl)methyl)acetamide

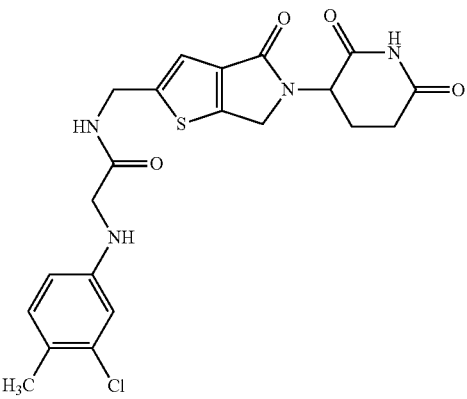 [SMILES: Cc1ccc(NCC(=O)NCc2cc3c(s2)CN(C2CCC(=O)NC2=O)C3=O)cc1Cl]

To a solution of tert-butyl 5-bromo-2-methylthiophene-3-carboxylate (4.50 g, 16.4 mmol) in tetrachloromethane (25 mL) was added NBS (3.20 g, 18.0 mmol) and dibenzoyl peroxide (0.39 g, 0.16 mmol). The mixture was heated at 80°

C. for 5 h then filtered, and the filtrate was concentrated. The residue was purified using silica gel eluting with PE/EA (1:1) to give tert-butyl 5-bromo-2-(bromomethyl)thiophene-3-carboxylate (5.38 g, 93% yield) as an oil.

To a solution of tert-butyl 5-bromo-2-(bromomethyl)thiophene-3-carboxylate (5.38 g, 15.2 mmol) in DMF (25 mL) at 0° C. was added TEA (3.37 g, 33.4 mmol) and 3-aminopiperidine-2,6-dione (2.99 g, 18.2 mmol). The mixture was heated at 80° C. overnight then concentrated, and the residue was purified using silica gel eluting with PE/EA (1:1) to give tert-butyl 5-bromo-2-(((2,6-dioxopiperidin-3-yl)amino)methyl)thiophene-3-carboxylate (2.29 g, 38% yield) as a solid. MS (ESI) m/z=403 [M+H]$^+$.

To a solution of tert-butyl 5-bromo-2-(((2,6-dioxopiperidin-3-yl)amino)methyl)thiophene-3-carboxylate (2.29 g, 5.69 mmol) in DCM (16 mL) at 0° C. was added TFA (5 mL). The mixture was stirred at RT for 5 h then concentrated to give 5-bromo-2-(((2,6-dioxopiperidin-3-yl)amino)methyl)thiophene-3-carboxylic acid (1.97 g, quant) as a solid. MS (ESI) m/z 347 [M+H]$^+$.

To a solution of 5-bromo-2-(((2,6-dioxopiperidin-3-yl)amino)methyl)-thiophene-3-carboxylic acid (1.97 g, 5.69 mmol) in DMF (20 mL) at 0° C. was added 2-(7-azabenzotriazol-1-yl)-N,N,N',N'-tetramethyluronium hexafluorophosphate (2.95 g, 8.53 mmol) and DIEA (1.47 g, 11.38 mmol). After 2 h at RT, the mixture was diluted with water and extracted with DCM. The combined organic layers were dried using Na$_2$SO$_4$, filtered and concentrated. The residue was triturated with EA then dried to give 3-(2-bromo-4-oxo-4H-thieno[2,3-c]pyrrol-5(6H)-yl)piperidine-2,6-dione (1.14 g, 61% yield) as a solid. MS (ESI) m/z=329 [M+H]$^+$.

To a solution of 3-(2-bromo-4-oxo-4H-thieno[2,3-c]pyrrol-5(6H)-yl)piperidine-2,6-dione (490 mg, 1.49 mmol) in DMF (20 mL) was added tris-(dibenzylideneacetone)dipalladium(0) (142 mg, 0.15 mmol), 1,1'-ferrocenediyl-bis-(diphenylphosphine) (179 mg, 0.33 mmol) and zinc cyanide (192 mg, 1.64 mmol). The mixture was heated at 150° C. under microwave for 1 h then concentrated, and the residue was purified using silica gel eluting with PE/EA (12) to give 5-(2,6-dioxopiperidin-3-yl)-4-oxo-5,6-dihydro-4H-thieno[2,3-c]pyrrole-2-carbonitrile (90 mg, 20% yield) as a solid. MS (ESI) m/z=276 [M+H]$^+$.

To a solution of 5-(2,6-dioxopiperidin-3-yl)-4-oxo-5,6-dihydro-4H-thieno[2,3-c]pyrrole-2-carbonitrile (90 mg, 0.33 mmol) in THF (3 mL) was added di-tert-butyl dicarbonate (107 mg, 0.49 mmol) and Raney-Ni (10 mg) then the mixture was purged twice with H$_2$. After 24 h, the mixture was filtered and concentrated. The residue was purified using silica gel eluting with PE/EA (1:2) to give tert-butyl ((5-(2,6-dioxopiperidin-3-yl)-4-oxo-5,6-dihydro-4H-thieno[2,3-c]pyrrol-2-yl)methyl)carbamate (60 mg, 48% yield) as a solid. MS (ESI) m/z=380 [M+H]$^+$.

To a solution of tert-butyl ((5-(2,6-dioxopiperidin-3-yl)-4-oxo-5,6-dihydro-4H-thieno[2,3-c]pyrrol-2-yl)methyl)carbamate (40 mg, 0.11 mmol) in DCM (4 mL) at 0° C. was added TFA (1 mL). After 2 h at RT, the mixture was concentrated then dissolved in DCM (4 mL). TEA (32 mg, 0.32 mmol) was added followed by 2-((3-chloro-4-methylphenyl)amino)acetic acid (31 mg, 0.16 mmol) and T3P (132 mg, 0.42 mmol, ≥50 wt. % in EA). After 2 h, the mixture was concentrated, and the residue was purified using prep-TLC as previously described to afford Compound 6 (17.6 mg, 36% yield) as a solid. MS (ESI) m/z 461 [M+H]$^+$. $^1$H NMR (400 MHz, DMSO-d6) δ 10.96 (s, 1H), 8.63 (t, J=6.4 Hz, 1H), 7.03 (s, 1H), 7.01 (d, J=8.4 Hz, 1H), 6.54 (s, 1H), 6.43 (dd, J=8.4, 2.4 Hz, 1H), 6.13 (t, J=6.0 Hz, 1H), 5.00-4.96 (m, 1H), 4.48-4.31 (m, 4H), 3.65 (d, J=6.0 Hz, 2H), 2.93-2.84 (m, 1H), 2.60-2.50 (m, 1H), 2.35-2.32 (m, 1H), 2.15 (s, 3H), 1.99-1.95 (s, 1H).

Example 7

Compound 7: 2-((3-chloro-4-methylphenyl)amino)-N-((5-(2,6-dioxopiperidin-3-yl)-4-oxo-5,6-dihydro-4H-thieno[3,4-c]pyrrol-1-yl)methyl)propanamide

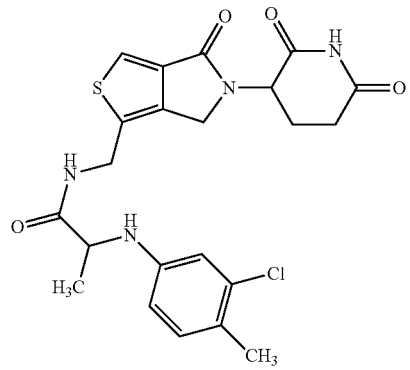 [SMILES: Cc1ccc(NC(C)C(=O)NCc2scc3c2CN(C2CCC(=O)NC2=O)C3=O)cc1Cl]

To a solution of 3-chloro-4-methylaniline (400 mg, 2.83 mmol) in acetone (35 mL) was added tert-butyl 2-bromopropanoate (890 mg, 4.26 mmol), KI (940 mg, 5.66 mmol), and K$_2$CO$_3$ (781 mg, 5.66 mmol). The mixture was heated at 60° C. under N$_2$ then filtrated and concentrated. The residue was purified using silica gel eluting with PE/EA (2:1) to give tert-butyl 2-((3-chloro-4-methylphenyl)amino)propanoate (151 mg, 19% yield).

To a solution of tert-butyl 2-((3-chloro-4-methylphenyl)amino)propanoate (151 mg, 0.56 mmol) in DCM (8 ml) was added TFA (2 mL). After 2 h, the mixture was concentrated, and the residue was diluted with water and extracted with DCM. The aqueous phase was concentrated to give 2-((3-chloro-4-methylphenyl)amino)propanoic acid (112 mg, crude) as an oil which was used in the next step without purification.

To a solution of tert-butyl ((5-(2,6-dioxopiperidin-3-yl)-4-oxo-5,6-dihydro-4H-thieno[3,4-c]pyrrol-1-yl)methyl)carbamate (90 mg, 0.24 mmol) in DCM (4 mL) at 0° C. was added TFA (1 mL). After 2.5 h at RT, the mixture was concentrated then dissolved in DCM (6 mL). TEA (0.07 ml, 0.48 mmol) was added followed by 2-((3-chloro-4-methylphenyl)amino)propanoic acid (110 mg, 0.24 mmol) and T3P (0.36 ml, 0.57 mmol, ≥50 wt. % in EA). After 2 h, the mixture was concentrated, and the residue was purified using prep-HPLC as previously described to afford Compound 7 (8.0 mg, 10% yield) as a solid. MS (ESI) m/z=475 [M+H]$^+$. $^1$H NMR (400 MHz, DMSO-d$_6$) δ 11.00 (s, 1H), 8.66 (s, 1H), 7.86 (s, 1H), 7.00-6.97 (m, 1H), 6.56 (s, 1H), 6.42 (t, J=7.6 Hz, 1H), 5.99 (t, J=8.0 Hz, 1H), 5.01-4.97 (m, 1H), 4.40-4.37 (m, 2H), 4.15-4.12 (m, 2H), 3.78-3.76 (m, 1H), 2.93-2.84 (m, 1H), 2.75-2.66 (m, 1H), 2.25-2.18 (m, 1H), 2.14 (s, 3H), 2.00-1.93 (m, 1H), 1.29 (d, J=6.4 Hz, 2H).

Example 8

Compound 8: 2-((3-chloro-4-(dimethylamino)phenyl)amino)-N-((5-(2,6-dioxopiperidin-3-yl)-4-oxo-5,6-dihydro-4H-thieno[3,4-c]pyrrol-1-yl)methyl)acetamide

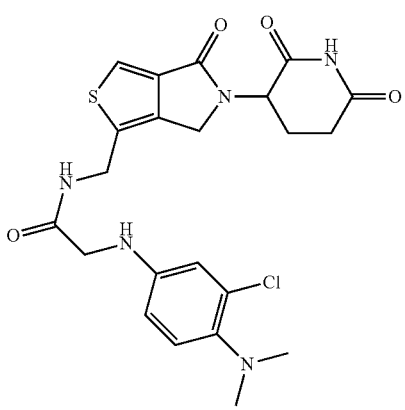 [SMILES: CN(C)c1ccc(NCC(=O)NCc2scc3c2CN(C2CCC(=O)NC2=O)C3=O)cc1Cl]

To a solution of 2-chloro-N$^1$,N$^1$-dimethylbenzene-1,4-diamine (1.1 g, 6.5 mmol) in acetone (20 mL) was added tert-butyl 2-bromoacetate (1.5 g, 7.8 mmol), KI (1.1 g, 6.5 mmol), and Cs$_2$CO$_3$ (1.8 g, 12.94 mmol). The mixture was heated at 60° C. under N$_2$ then filtered and concentrated. The residue was purified using silica gel eluting with PE/EA (2:1) to give tert-butyl 2-((3-chloro-4-(dimethylamino)phenyl)amino)acetate (1.5 g, 83% yield) as an oil. MS (ESI) m/z 285 [M+H]$^+$.

To a solution of tert-butyl 2-((3-chloro-4-(dimethylamino)phenyl)-amino)acetate (300 mg, 1.1 mmol) in DCM (5 ml) was added TFA (2 mL). After 2 h, the mixture was concentrated, and the residue was diluted with water and extracted with DCM. The aqueous phase was concentrated to give 2-((3-chloro-4-(dimethylamino)phenyl)-amino)acetic acid as an oil (150 mg, crude) which was used in the next step without purification.

To a solution of tert-butyl ((5-(2,6-dioxopiperidin-3-yl)-4-oxo-5,6-dihydro-4H-thieno[3,4-c]pyrrol-1-yl)methyl)carbamate (100 mg, 0.27 mmol) in DCM (5 mL) at 0° C. was added TFA (2 mL). After 2 h at RT, the mixture was concentrated then dissolved in DCM (5 mL). TEA (0.2 mL) was added followed by 2-((3-chloro-4-(dimethylamino)phenyl)amino)acetic acid (0.27 mmol) and T3P (0.1 ml, 0.16 mmol, ≥50 wt. % in EA). After 2 h, the mixture was concentrated, and the residue was purified using prep-HPLC as previously described to afford Compound 8 (25 mg, 28% yield) as a solid. MS (ESI) m/z 490 [M+H]$^+$. $^1$H NMR (400 MHz, DMSO-d$_6$) δ 10.96 (s, 1H), 8.58 (t, J=6.0 Hz, 1H), 7.86 (s, 1H), 6.96 (d, J=8.4 Hz, 1H), 6.57 (d, J=2.4 Hz, 1H), 6.46 (dd, J=2.8, 8.8 Hz, 1H), 6.01 (t, J=6.0 Hz, 1H), 4.99 (dd, J=4.8, 13.2 Hz, 1H), 4.40 (d, J=6.0 Hz, 2H), 4.20 (dd, J=15.6, 37.6 Hz, 2H), 3.63 (d, J=6.4 Hz, 2H), 2.88-2.85 (m, 1H), 2.60-2.59 (m, 1H), 2.56 (s, 6H), 2.31-2.77 (m, 1H), 1.97-1.91 (m, 1H).

Example 9

Compound 9: N-((5-(2,6-dioxopiperidin-3-yl)-4-oxo-5,6-dihydro-4H-thieno[3,4-c]pyrrol-1-yl)methyl)-2-((4-(morpholinomethyl)phenyl)amino)acetamide

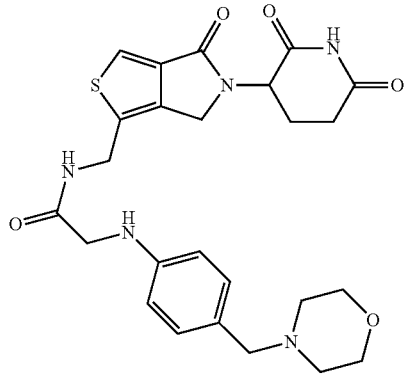 [SMILES: O=C(CNc1ccc(CN2CCOCC2)cc1)NCc1scc2c1CN(C1CCC(=O)NC1=O)C2=O]

To a solution of 3-(1-(aminomethyl)-4-oxo-4H-thieno[3,4-c]pyrrol-5(6H)-yl)piperidine-2,6-dione TFA salt (60 mg, 0.15 mmol) in DCM (4.0 mL) was added TEA (39 mg, 0.38 mmol), 2-((4-(morpholinomethyl)phenyl)amino)acetic acid (57 mg, 0.23 mmol) and T3P (97 mg, 0.31 mmol, ≥50 wt. % in EA). After 1 h, the mixture was concentrated, and the residue was purified using prep-TLC as previously described to afford Compound 9 (15.3 mg, 20% yield) as a solid. MS (ESI) m/z 512.1 [M+1]$^+$. $^1$H NMR (400 MHz, DMSO-d$_6$) δ 11.00 (s, 1H), 8.58 (s, 1H), 7.85 (s, 1H), 7.02 (br, 2H), 6.52 (s, 2H), 5.97 (br, 1H), 5.02-4.98 (m, 1H), 4.41 (d, J=6.0 Hz, 2H), 4.28-4.13 (m, 2H), 3.67 (s, 2H), 3.56 (s, 4H), 2.94-2.85 (m, 1H), 2.67-2.55 (m, 2H), 2.34-2.23 (m, 4H), 1.99-1.93 (s, 1H).

Example 10

Compound 10: 2-((4-(dimethylamino)-3-methylphenyl)amino)-N-((5-(2,6-dioxopiperidin-3-yl)-4-oxo-5,6-dihydro-4H-thieno[3,4-c]pyrrol-1-yl)methyl)acetamide

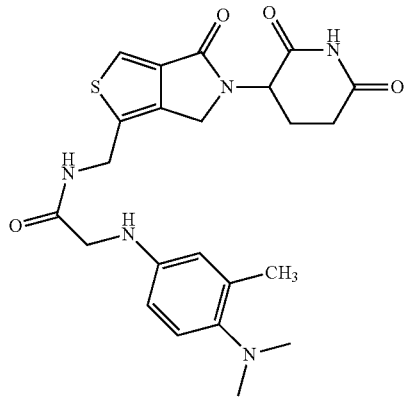 [SMILES: Cc1cc(NCC(=O)NCc2scc3c2CN(C2CCC(=O)NC2=O)C3=O)ccc1N(C)C]

To a solution of 3-(1-(aminomethyl)-4-oxo-4H-thieno[3,4-c]pyrrol-5(6H)-yl)piperidine-2,6-dione TFA salt (70 mg, 0.18 mmol) in DCM (4 mL) was added TEA (54 mg, 0.53 mmol), 2-((4-(dimethylamino)-3-methylphenyl)amino)acetic acid (56 mg, 0.27 mmol) and T3P (169 mg, 0.53 mmol, ≥50 wt. % in EA). After 2 h, the mixture was concentrated, and the residue was purified using prep-TLC as previously described to afford Compound 10 (17.1 mg, 20% yield) as a solid. MS (ESI) m/z 470.1 [M+1]$^+$. $^1$H NMR (400 MHz, DMSO-d$_6$) δ 10.97 (s, 1H), 8.52 (t, J=6.0 Hz, 1H), 7.85 (s, 1H), 6.84 (d, J=8.4 Hz, 1H), 6.35-6.30 (m, 2H), 5.65 (t, J=6.0 Hz, 1H), 5.01-4.96 (m, 1H), 4.40 (d, J=6.4 Hz, 4H), 4.27-4.14 (m, 2H), 3.59 (d, J=6.0 Hz, 2H), 2.91-2.84 (m, 1H), 2.63-2.55 (m, 1H), 2.50 (s, 9H), 2.33-2.23 (m, 1H), 1.93 (s, 3H), 1.97-1.91 (s, 1H).

Example 11

Compound 11: N-((5-(2,6-dioxopiperidin-3-yl)-4-oxo-5,6-dihydro-4H-thieno[3,4-c]pyrrol-1-yl)methyl)-2-((3-(morpholinomethyl)phenyl)amino)acetamide

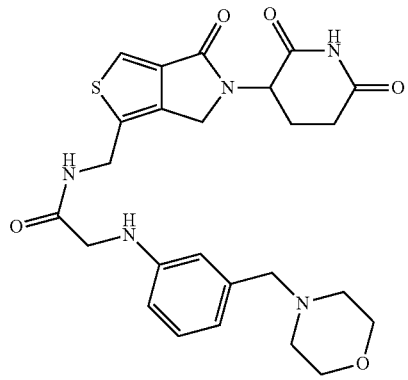 [SMILES: O=C(CNc1cccc(CN2CCOCC2)c1)NCc1scc2c1CN(C1CCC(=O)NC1=O)C2=O]

To a solution of 3-(morpholinomethyl)aniline (384 mg, 2.0 mmol) in acetone (30 mL) was added tert-butyl 2-bromoacetate (627 mg, 3.0 mmol), KI (664 mg, 4.0 mmol), and K$_2$CO$_3$ (552 mg, 4.0 mmol). The mixture was heated at 60° C. under N$_2$ then filtered and concentrated. The residue was purified using silica gel eluting with PE/EA (2:1) to give tert-butyl 2-((3-(morpholinomethyl)phenyl)amino)acetate (260 mg, 40% yield).

To a solution of tert-butyl 2-((3-(morpholinomethyl)phenyl)amino)acetate (150 mg, 0.49 mmol) in DCM (4 ml) was added TFA (1 mL). After 2 h, the mixture was concentrated, and the residue was diluted with water and extracted with DCM. The aqueous phase was concentrated to give 2-((3-(morpholinomethyl)phenyl)amino)acetic acid (121 mg, crude) as an oil which was used in the next step without purification.

To a solution of tert-butyl ((5-(2,6-dioxopiperidin-3-yl)-4-oxo-5,6-dihydro-4H-thieno[3,4-c]pyrrol-1-yl)methyl)carbamate (100 mg, 0.27 mmol) in DCM (3 mL) at 0° C. was added TFA (1 mL). After 2 h at RT, the mixture was concentrated then dissolved in DCM (6 mL). TEA (55 mg, 0.54 mmol) was added followed by 2-((3-(morpholinomethyl)phenyl)amino)acetic acid (67.6 mg, 0.27 mmol, crude) and T3P (0.36 ml, 0.57 mmol, ≥50 wt. % in EA). After 2 h, the mixture was concentrated, and the residue was purified using prep-HPLC as previously described to afford Compound 11 (32 mg, 24% yield) as a solid. MS (ESI) m/z=512 [M+H]$^+$. $^1$H NMR (400 MHz, DMSO-d$_6$) δ 10.99 (s, 1H), 8.59 (t, J=6.1 Hz, 1H), 7.85 (s, 1H), 7.02 (t, J=7.6 Hz, 1H), 6.53-6.50 (m, 2H), 6.41-6.39 (m, 1H), 6.01 (t, J=5.6 Hz, 1H), 4.98 (dd, J=4.0, 13.6 Hz, 1H), 4.40 (d, J=6.0 Hz, 2H), 4.24-4.10 (m, 2H), 3.65-3.64 (m, 2H), 3.55 (t, J=4.0 Hz, 4H), 3.30 (s, 2H), 2.91-2.84 (m, 1H), 2.59-2.55 (m, 1H), 2.46 (s, 4H), 2.30-2.21 (m, 1H), 2.01-1.90 (m, 1H).

Example 12

Compound 12: 2-((3-chloro-4-methylphenyl)amino)-N-((5-(2,6-dioxopiperidin-3-yl)-4-oxo-5,6-dihydro-4H-thieno[3,4-c]pyrrol-1-yl)methyl)acetamide

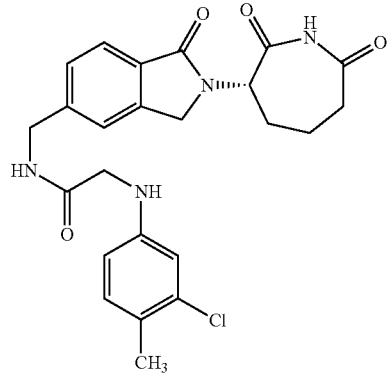 [SMILES: Cc1ccc(NCC(=O)NCc2ccc3c(c2)CN([C@H]2CCCC(=O)NC2=O)C3=O)cc1Cl]

To a solution of 3-(1-(aminomethyl)-4-oxo-4H-thieno[3,4-c]pyrrol-5(6H)-yl)piperidine-2,6-dione TFA salt (177 mg, 0.44 mmol) and 2-((3-chloro-4-methylphenyl)amino)acetic acid (87 mg, 0.44 mmol) in DCM (10 mL) was added TEA (177 mg, 1.76 mmol) and T3P (1.0 mL, 1.57 mmol, ≥50 wt. % in EA). After 2 h, the mixture was diluted with WATER and extracted with EA. The combined organic layers were dried over Na2SO4, filtered, and concentrated. The residue was purified using silica gel eluting with PE/EA (1:3) to afford Compound 12 (40.0 mg, 19% yield) as a solid. MS (ESI) m/z=468.8 [M+H]$^+$. $^1$H NMR (DMSO-d$_6$, 400 MHz) δ: 10.73 (s, 1H), 8.58-8.55 (m, 1H), 7.63 (d, J=8 Hz, 1H), 7.38 (s, 1H), 7.35 (d, J=8 Hz, 1H), 7.05 (d, J=9.2 Hz, 1H), 6.58 (d, J=2 Hz, 1H), 6.48-6.46 (m, 1H), 6.20-6.17 (m, 1H), 5.25-5.21 (m, 1H), 4.45-4.40 (m, 4H), 3.71 (d, J=3.2 Hz, 2H), 3.13-3.05 (m, 1H), 2.59-2.55 (m, 1H), 2.30-2.22 (m, 1H), 2.15 (s, 3H), 2.13-2.00 (m, 2H), 1.86-1.78 (m, 1H).

Example 13

Compound 13: 2-((3-chloro-4-methylphenyl)amino)-N-((2-(2,6-dioxopiperidin-3-yl)-3-oxoisoindolin-5-yl)methyl)acetamide

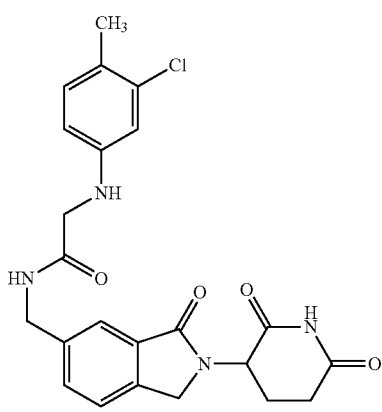

To a solution of 3-(6-(aminomethyl)-1-oxoisoindolin-2-yl)piperidine-2,6-dione (41 mg, 0.15 mmol) in DCM (10 mL) was added TEA (46 mg, 0.45 mmol), 2-((3-chloro-4-methylphenyl)amino)acetic acid (36 mg, 0.18 mmol) and T3P (0.1 mL, 0.157 mmol, ≥50 wt. % in EA). After 1.5 h, the mixture was concentrated, and the residue was purified using prep-HPLC as previously described to afford Compound 13 (15 mg, 22% yield) as a solid. MS (ESI) m/z=455.0 [M+H]$^+$. $^1$H NMR (400 MHz, DMSO-d$_6$) δ 10.71 (brs, 1H), 8.54 (t, J=6.0 Hz, 1H), 7.50 (q, J=8.0, 2H), 7.03 (d, J=8.0, 1H), 6.57 (d, J=2.0, 1H), 6.44 (dd, J=2.0, 6.0, 1H), 6.13 (t, J=6.0, 1H), 5.11 (dd, J=4.8, 8.4, 1H), 4.28 (dd, J=15.2, 42.8, 2H), 4.44-4.27 (m, 4H), 3.69 (d, J=5.6, 1H), 2.94-2.87 (m, 1H), 2.62-2.58 (m, 1H), 2.44-2.35 (m, 1H), 2.16 (s, 1H), 2.01-1.98 (m, 1H).

Example 14

Compound 14: 2-((3-chloro-4-methylphenyl)amino)-N-((2-(2,6-dioxopiperidin-3-yl)-1-oxoisoindolin-4-yl)methyl)acetamide

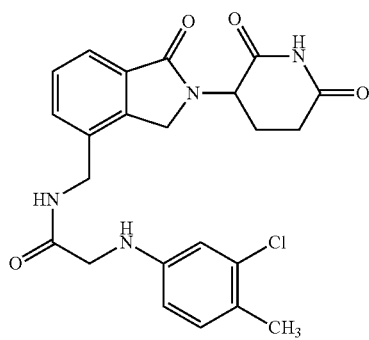 [SMILES: Cc1ccc(NCC(=O)NCc2cccc3c2CN(C2CCC(=O)NC2=O)C3=O)cc1Cl]

To a solution of 3-(4-(aminomethyl)-1-oxoisoindolin-2-yl)piperidine-2,6-dione (36.6 mg, 0.134 mmol) in DCM (5 mL) was added TEA (40.2 mg, 0.402 mmol), 2-((3-chloro-4-methylphenyl)amino)acetic acid (29.3 mg, 0.147 mmol), and T3P (85.2 mg, 0.268 mmol, ≥50 wt. % in EA). After 2 h, the mixture was concentrated, and the residue was purified using prep-TLC as previously described to afford Compound 14 (46.7 mg, 77% yield) as a solid. MS (ESI) m/z 455.1 [M+1]$^+$. $^1$H NMR (400 MHz, DMSO-d$_6$) δ 11.01 (s, 1H), 8.53 (t, J=6.0 Hz, 1H), 7.63-7.61 (m, 1H), 7.66-7.44 (m, 2H), 7.02 (d, J=8.4 Hz, 1H), 6.57 (s, 1H), 6.44 (d, J=6.0 Hz, 1H), 6.15 (t, J=6.0 Hz, 1H), 5.15-5.10 (m, 1H), 4.49-4.36 (m, 4H), 3.69 (d, J=6.0 Hz, 2H), 2.97-2.88 (m, 1H), 2.73-2.63 (m, 1H), 2.39-2.28 (m, 1H), 2.16 (s, 3H), 1.99-1.95 (s, 1H).

Example 15

Compound 15: 2-((3-chloro-4-methylphenyl)amino)-N-((2-(2,6-dioxopiperidin-3-yl)-1-oxoisoindolin-5-yl)methyl)propanamide

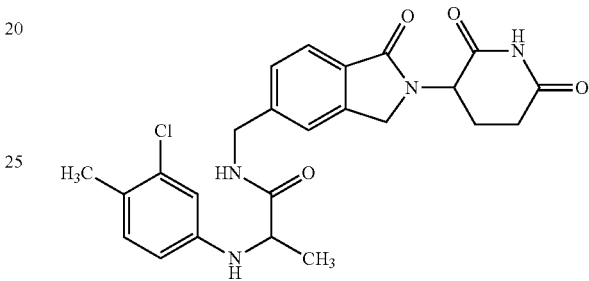

To a solution of 3-(5-(aminomethyl)-1-oxoisoindolin-2-yl)piperidine-2,6-dione TFA salt (90 mg, 0.24 mmol) in DCM (10 mL) was added TEA (49 mg), (3-chloro-4-methylphenyl)alanine (34.0 mg, 0.24 mmol), and T3P (0.36 ml, 0.51 mmol, ≥50 wt. % in EA). After 4 h, the mixture was concentrated, and the residue was purified using prep-HPLC as previously described to afford Compound 15 (38.8 mg, 34% yield) as a solid. MS (ESI) m/z=512 [M+H]$^+$. $^1$H NMR (400 MHz, DMSO-d$_6$) δ 10.97 (s, 1H), 8.59 (t, J=6.0 Hz, 1H), 7.85 (d, J=8.0 Hz, 1H), 7.32-7.30 (m, 2H), 7.03 (d, J=8.4 Hz, 1H), 6.62-6.60 (m, 1H), 6.48 (dd, J=2.0, 8.4 Hz, 1H), 5.96 (d, J=7.2 Hz, 1H), 5.13-5.08 (m, 1H), 4.39-4.34 (m, 2H), 4.31-4.18 (m, 2H), 3.88-3.81 (m, 1H) 2.94-2.87 (m, 1H), 2.68-2.58 (m, 1H), 2.43-2.32 (m, 1H), 2.16 (s, 3H), 2.03-1.97 (m, 1H), 1.33 (d, J=6.8 Hz, 3H).

Example 16

Compound 16: N-((2-(2,6-dioxopiperidin-3-yl)-1-oxoisoindolin-5-yl)methyl)-2-(phenylamino)acetamide

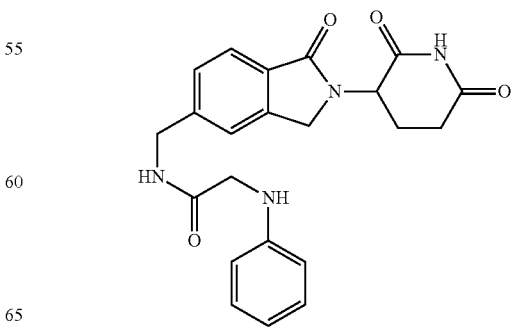

To a solution of aniline (2.0 g, 21.5 mmol) in acetone (20 mL) was added tert-butyl 2-bromoacetate (5.0 g, 25.8 mmol) and K$_2$CO$_3$ (4.44 g, 32.2 mmol). The mixture was heated at 60° C. for 1 h then filtered, and the filtrate was concentrated. The residue was purified using silica gel eluting with PE/EA (2:1) to give tert-butyl 2-(phenylamino)acetate (700 mg, 17% yield) as a liquid. MS (ESI) m/z=208.2 [M+H]$^+$.

To a solution of tert-butyl 2-(phenylamino)acetate (105 mg, 0.51 mmol) in DCM (5 ml) was added TFA (5 mL). After 3 h, the mixture was concentrated, and the residue was diluted with water and extracted with DCM. The aqueous phase was concentrated to give 2-(phenyl)amino)acetic acid (68 mg, 90% yield) as an oil. MS (ESI) m/z=152.1 [M+H]$^+$.

To a solution of 3-(5-(aminomethyl)-1-oxoisoindolin-2-yl)piperidine-2,6-dione TFA salt (111 mg, 0.3 mmol) in DCM (5 mL) at 0° C. was added 2-(phenyl)amino)acetic acid (68 mg, 0.45 mmol, crude), TEA (151 mg, 1.5 mmol) and T3P (0.286 g, 0.90 mmol, ≥50 wt. % in EA). After 1 h, water was added, and the mixture was extracted with DCM. The combined organic layers were dried over Na$_2$SO$_4$, filtered, concentrated. The residue was purified using silica gel eluting with PE/EA (1:3) to afford Compound 16 (14 mg, 11% yield) as a solid. MS (ESI) m/z=407.1 [M+H]$^+$. $^1$H NMR (DMSO-d$_6$, 400 MHz) δ: 10.99 (s, 1H), 8.53 (t, J=6.0 Hz, 1H), 7.64-7.62 (m, 1H), 7.38-7.34 (m, 2H), 7.12-7.08 (m, 2H), 6.62-6.55 (m, 3H), 6.03-6.00 (m, 1H), 5.10 (dd, J=4.8, 13.6 Hz, 1H), 4.41-4.36 (m, 3H), 4.28-4.23 (m, 1H), 3.70 (d, J=6.0 Hz, 1H), 2.95-2.87 (m, 1H), 2.67-2.57 (m, 1H), 2.41-2.33 (m, 1H), 2.01-1.97 (m, 1H).

Example 17

Compound 17: 2-((4-(tert-butyl)phenyl)amino)-N-((2-(2,6-dioxopiperidin-3-yl)-1-oxoisoindolin-5-yl)methyl)acetamide

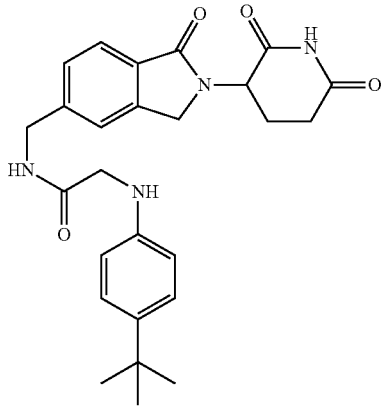 [SMILES: CC(C)(C)c1ccc(NCC(=O)NCc2ccc3c(c2)CN(C2CCC(=O)NC2=O)C3=O)cc1]

To a solution of 4-(tert-butyl)aniline (3.2 g, 21.5 mmol) in acetone (20 mL) was added tert-butyl 2-bromoacetate (5.0 g, 25.8 mmol) and K$_2$CO$_3$ (4.44 g, 32.2 mmol). After 1 h at 60° C., the mixture was filtered, and the filtrate was concentrated. The residue was purified using silica gel eluting with PE/EA (2:1) to give tert-butyl 2-((4-(tert-butyl)phenyl)amino)acetate (1.21 g, 21% yield) as a liquid.

To a solution of tert-butyl 2-((4-(tert-butyl)phenyl)amino)acetate (0.20 g, 0.7 mmol) in DCM (3 ml) was added TFA (3 mL). After 1.5 h, the mixture was concentrated, and the residue was diluted with water. The mixture was extracted with DCM and the aqueous phase was concentrated to give 2-((4-(tert-butyl)phenyl)amino)acetic acid (145 mg, 100% yield) as an oil. MS (ESI) m/z=208.1 [M+H]$^+$.

To a solution of 3-(5-(aminomethyl)-1-oxoisoindolin-2-yl)piperidine-2,6-dione TFA salt (233 mg, 0.67 mmol) in DCM (5 mL) at 0° C. was added 2-((4-(tert-butylphenyl)amino)acetic acid (145 mg, 0.7 mmol), TEA (318 mg, 3.15 mmol) and T3P (0.60 g, 1.89 mmol, ≥50 wt. % in EA). After 1 h at RT, water was added, and the mixture was extracted with DCM. The combined organic layers were dried over Na$_2$SO$_4$, filtered, and concentrated. The residue was purified using silica gel eluting with PE/EA (1:3) to afford Compound 17 (170 mg, 59% yield) as a solid. MS (ESI) m/z=463.2 [M+H]$^+$. $^1$H NMR (DMSO-d$_6$, 400 MHz) δ: 10.97 (s, 1H), 8.48 (t, J=5.6 Hz, 1H), 7.63 (d, J=8.0 Hz, 1H), 7.41 (s, 1H), 7.35 (d, J=8.0 Hz, 1H), 7.14-7.11 (m, 2H), 6.50-6.49 (m, 2H), 5.84 (t, J=5.2 Hz, 1H), 5.10 (dd, J=4.8, 13.6 Hz, 1H), 4.42-4.38 (m, 3H), 4.28-4.23 (m, 1H), 3.67 (d, J=6.4 Hz, 1H), 2.95-2.87 (m, 1H), 2.67-2.57 (m, 1H), 2.34-2.32 (m, 1H), 2.02-1.97 (m, 1H).

Example 18

Compound 18: 2-((3-(dimethylamino)-4-methylphenyl)amino)-N-((2-(2,6-dioxopiperidin-3-yl)-1-oxoisoindolin-5-yl)methyl)acetamide

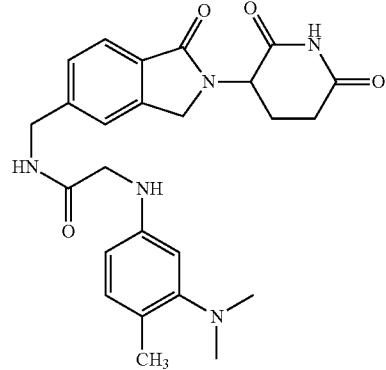

To a solution of N$^1$,N$^1$,6-trimethylbenzene-1,3-diamine (424 mg, 2.82 mmol) in acetone (10 mL) was added tert-butyl 2-bromoacetate (604 mg, 3.10 mmol), K$_2$CO$_3$ (778.3 mg 5.64 mol) and KI (468.1 mg, 2.82 mmol). After 3 h at 60° C., water was added, and the mixture was extracted with DCM. The combined organic layers were dried over Na$_2$SO$_4$, filtered, and concentrated. The residue was purified using silica gel eluting with PE/EA (2:1) to give tert-butyl 2-((3-(dimethylamino)-4-methylphenyl)amino)acetate (604 mg, 81% yield) as an oil. MS (ESI) m/z 265.2[M+H]$^+$.

To a solution of tert-butyl 2-((3-(dimethylamino)-4-methylphenyl)amino)-acetate (213 mg, 0.806 mmol) in DCM (6 mL) was added TFA (3 mL). The mixture was stirred overnight and concentrated to give 2-((3-(dimethylamino)-4-methylphenyl)amino)acetic acid (167.9 mg, crude) which was used in the next step without purification.

To a solution of tert-butyl ((2-(2,6-dioxopiperidin-3-yl)-1-oxoisoindolin-5-yl) methyl)carbamate (307.3 mg, 0.806 mmol) in DCM (8 mL) was added TFA (2 mL). After 3 h, the solution was concentrated to give 3-(5-(aminomethyl)-1-oxoisoindolin-2-yl)piperidine-2,6-dione TFA salt (220.3 mg, crude) which was used in the next step without purification.

To a solution of 3-(5-(aminomethyl)-1-oxoisoindolin-2-yl)piperidine-2,6-dione TFA salt (220.3 mg, 0.806 mmol) and 2-((3-(dimethylamino)-4-methylphenyl)amino)acetic acid (167.9 mg, 0.806 mmol) in DCM was added TEA (203.5 mg, 2.015 mmol) followed by T3P (640.8 mg, ≥50 wt. % in EA, 2.015 mmol). After stirring overnight, water was added, and the mixture was extracted with DCM. The combined organic layers were dried over $Na_2SO_4$, filtered, concentrated. The residue was purified using prep-HPLC as previously described to afford 2-((3-(dimethylamino)-4-methylphenyl)amino)-N-((2-(2,6-dioxopiperidin-3-yl)-1-oxoisoindolin-5-yl)methyl)acetamide (27.8 mg, 8% yield) as a solid. MS (ESI) m/z 464.0 $[M+H]^+$. $^1$H NMR (400 MHz, DMSO-$d_6$) δ 10.98 (s, 1H), 8.46 (t, J=6.0 Hz, 1H), 7.62 (d, J=7.6 Hz, 1H), 7.38 (s, 1H), 7.35 (d, J=7.6 Hz, 1H), 6.85 (d, J=8.0 Hz, 1H), 6.27 (d, J=2.0 Hz, 1H), 6.13 (dd, =2.0 Hz, $J_2$=8.0 Hz, 1H), 5.77 (t, J=5.6 Hz, 1H), 5.10 (dd, $J_1$=5.2 Hz, $J_2$=13.2 Hz, 1H), 4.22-4.41 (m, 4H), 3.66 (d, J=5.6 Hz, 2H), 2.87-2.94 (m, 1H), 2.589-2.624 (m, 1H), 2.52 (s, 6H), 2.36-2.50 (m, 1H), 2.10 (s, 3H), 1.985-2.011 (m, 1H).

Example 19

Compound 19: 2-((3-chloro-4-methylphenyl)amino)-N-((2-(2,6-dioxopiperidin-3-yl)-1,3-dioxoisoindolin-5-yl)methyl)acetamide

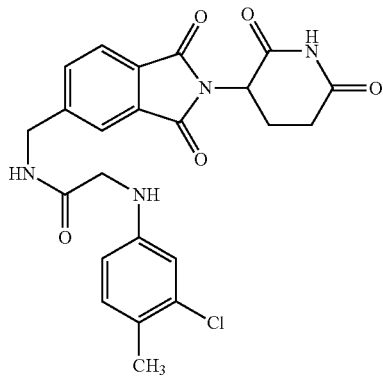 [SMILES: Cc1ccc(NCC(=O)NCc2ccc3c(c2)C(=O)N(C2CCC(=O)NC2=O)C3=O)cc1Cl]

A solution of 3-bromoisobenzofuran-1,3-dione (2.0 g, 8.8 mmol), 3-aminopiperidine-2,6-dione (1.4 g, 8.8 mmol) and AcONa (1.4 g, 17.6 mmol) in AcOH (25 mL) was heated at 120° C. for 5 h. The mixture was concentrated, and the residue was washed with water followed by MeOH and DCM to give 5-bromo-2-(2,6-dioxopiperidin-3-yl)isoindoline-1,3-dione (2.7 g, 90% yield) as a solid. MS (ESI) m/z 359.0 $[M+Na]^+$.

A solution of 5-bromo-2-(2,6-dioxopiperidin-3-yl)isoindoline-1,3-dione (1.0 g, 3.0 mmol) and CuCN (0.8 g, 9.0 mmol) in NMP (8 mL) was heated at 180° C. under microwave for 2 h. The mixture was filtered, diluted with water, and extracted with EA. The combined organic layers were washed with brine, dried over $Na_2SO_4$, filtered, and concentrated. The residue was washed with MeOH and DCM to give 2-(2,6-dioxopiperidin-3-yl)-1,3-dioxoisoindoline-5-carbonitrile (600 mg, 71% yield) as a solid. MS (ESI) m/z 306.0 $[M+Na]^+$.

A solution of 2-(2,6-dioxopiperidin-3-yl)-1,3-dioxoisoindoline-5-carbonitrile (0.21 g, 0.75 mmol), $Boc_2O$ (0.24 mg, 1.12 mmol) and Raney-Ni (0.06 mg) in MeOH (20 mL) was stirred under $H_2$ for approximately 2 d. The mixture was filtered, and the residue was purified using silica gel eluting with PE/EA (1:1) to give tert-butyl ((2-(2,6-dioxopiperidin-3-yl)-1,3-dioxoisoindolin-5-yl)methyl)carbamate (80 mg, 28% yield) as a solid. MS (ESI) m/z 405.2 $[M+NH_4^+]$.

To a solution of tert-butyl ((2-(2,6-dioxopiperidin-3-yl)-1,3-dioxoisoindolin-5-yl)methyl)carbamate (80 mg, 0.20 mmol) in DCM (3 mL) was added TFA (1 mL). After 1 h, the mixture was concentrated, and the residue was washed with methyl tert-butyl ether to give 5-(aminomethyl)-2-(2,6-dioxopiperidin-3-yl)isoindoline-1,3-dione TFA salt (75 mg, crude) as a solid. MS (ESI) m/z 288.0 $[M+H]^+$.

To a solution of 5-(aminomethyl)-2-(2,6-dioxopiperidin-3-yl)isoindoline-1,3-dione TFA salt (75 mg, 0.20 mmol, crude) in DMF (5 mL) was added 2-((3-chloro-4-methylphenyl)amino)acetic acid (40 mg, 0.20 mmol), HOBT (40 mg, 0.30 mmol), EDCI (57 mg, 0.30 mmol) and DIEA (77 mg, 0.60 mmol). After stirring overnight, the mixture was concentrated, and the residue was purified using prep-HPLC as previously described to afford Compound 19 (26 mg, 27% yield) as a solid. MS (ESI) m/z 468.9 $[M+H]^+$. $^1$H NMR (DMSO-$d_6$, 400 MHz) δ: 11.10 (s, 1H), 8.64-8.61 (m, 1H), 7.83 (d, J=8.0 Hz, 1H), 7.77 (s, 1H), 7.71-7.69 (m, 1H), 7.03 (d, J=8.0 Hz, 1H), 6.54 (d, J=4.0 Hz, 1H), 6.45-6.42 (m, 1H), 6.17-6.14 (m, 1H), 5.16-5.11 (m, 1H), 4.45 (d, J=8.0 Hz, 2H), 3.70 (d, J=8.0 Hz, 2H), 2.90-2.86 (m, 1H), 2.63-2.52 (m, 2H), 2.15 (s, 3H), 2.09-2.02 (m, 1H).

Example 20

Compound 20: 2-((6-chloro-5-methylpyridin-2-yl)amino)-N-((2-(2,6-dioxopiperidin-3-yl)-1-oxoisoindolin-5-yl)methyl)acetamide

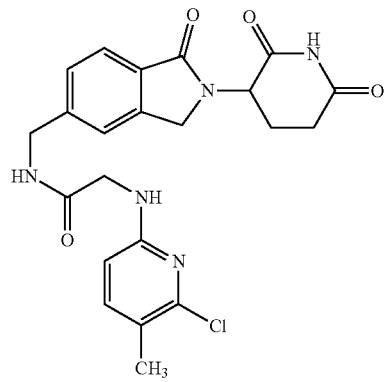

To a solution of 6-chloro-5-methylpyridin-2-amine (282 mg, 2.0 mmol) in DMF (10 mL) was added tert-butyl 2-bromoacetate (0.7 mL, 4 mmol) and KI (166 mg, 1 mmol), and $Cs_2CO_3$ (552 mg, 4 mmol). After heating at 110° C. overnight, the mixture was diluted with water and extracted with EA. The combined organic layers were dried over $Na_2SO_4$, filtrated, and concentrated. The residue was purified using silica gel eluting with PE/EA (2:1) to give 2-((6-chloro-5-methylpyridin-2-yl)amino)acetic acid (232 mg, 58% yield) as a solid. MS (ESI) m/z 201 $[M+1]^+$.

To a solution of tert-butyl ((2-(2,6-dioxopiperidin-3-yl)-1-oxoisoindolin-5-yl)methyl)carbamate (100 mg, 0.27 mmol) in DCM (3 mL) was added TFA (1 mL). After 1 h, the mixture was concentrated, dissolved in DCM (3 mL), and cooled to 0° C. then 2-((6-chloro-5-methylpyridin-2-yl)

amino)acetic acid (60 mg, 0.29 mmol), TEA (0.1 mL) and T3P (0.1 mL, 0.015 mmol, ≥50 wt. % in EA) were added. After 1 h at 0° C., the mixture was concentrated. The residue was purified using prep-HPLC as previously described to afford Compound 20 (10.6 mg, 9% yield) as a solid. MS (ESI) m/z 456.1 [M+H]+. 1H NMR (400 MHz, DMSO-d6) δ 10.97 (s, 1H), 8.48 (t, J=6.0 Hz, 1H), 7.64 (d, J=8.0 Hz, 1H), 7.44-7.37 (m, 3H), 7.04 (t, J=5.6 Hz, 1H), 6.49 (d, J=8.0 Hz, 1H), 5.10 (dd, J=4.8, 13.2 Hz, 1H), 4.42-4.26 (m, 4H), 3.86 (d, J=6.0 Hz, 2H), 2.95-2.86 (m, 1H), 2.67-2.58 (m, 1H), 2.45-2.33 (m, 1H), 2.14 (s, 3H), 2.03-1.99 (m, 1H).

Example 21

Compound 21: N-((2-(2,6-dioxopiperidin-3-yl)-1-oxoisoindolin-5-yl)methyl)-2-((3-methyl-4-(pyrrolidin-1-yl)phenyl)amino)acetamide

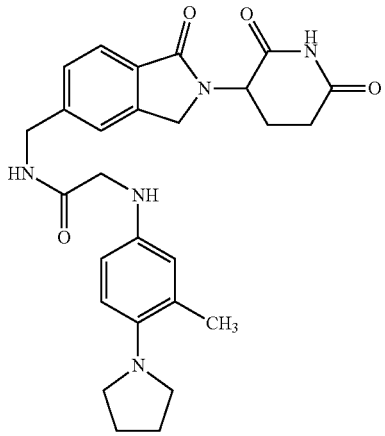 [SMILES: Cc1cc(NCC(=O)NCc2ccc3c(c2)CN(C2CCC(=O)NC2=O)C3=O)ccc1N1CCCC1]

To a solution of 1-(2-methyl-4-nitrophenyl)pyrrolidine (1.3 g, 6.3 mmol) in MeOH (20 mL) was added Pd/C (260 mg). After 16 h under H2, the mixture was filtered and concentrated. The residue was purified using silica gel eluting with PE/EA (1:1) to give 3-methyl-4-(pyrrolidin-1-yl)aniline (950 mg, 86% yield) as an oil. MS (ESI) m/z 177.2 [M+H]+.

To a solution of 3-methyl-4-(pyrrolidin-1-yl)aniline (950 mg, 5.39 mmol) in THF (20 mL) was added tert-butyl 2-bromoacetate (1.05 g, 5.39 mmol) and K2CO3 (1.49 g, 10.78 mmol). After 16 h at 75° C., the mixture was diluted with water and extracted with EA. The combined organic layers were concentrated, and the residue was purified using silica gel eluting with PE/EA (2:1) to give tert-butyl 2-((3-methyl-4-(pyrrolidin-1-yl)phenyl)amino)acetate (630 mg, 40% yield) as a an oil. MS (ESI) m/z 291.2 [M+H]+.

To a solution of tert-butyl 2-((3-methyl-4-(pyrrolidin-1-yl)phenyl)amino)-acetate (200 mg, 0.689 mmol) in DCM (10 mL) was added TFA (2 mL). After 4 h, the solution was concentrated to give 2-((3-methyl-4-(pyrrolidin-1-yl)phenyl)amino)acetic acid (150 mg, 93% yield) as a solid. MS (ESI) m/z 235.2[M+H]+.

To a solution of 2-((3-methyl-4-(pyrrolidin-1-yl)phenyl)amino)acetic acid (200 mg, 0.52 mmol) in DCM (10 mL) was added 3-(5-(aminomethyl)-1-oxoisoindolin-2-yl)piperidine-2,6-dione (62.6 mg, 0.267 mmol), TEA (81.1 mg, 0.801 mmol) and T3P (102 mg, 0.321 mmol, ≥50 wt. % in EA). After 1 h, water was added, and the mixture was extracted with DCM. The combined organic layers were concentrated, and the residue was purified using prep-HPLC as previously described to afford Compound 21 (29 mg, 22% yield) as a solid. MS (ESI) m/z 490.2 [M+H]+. 1H NMR (400 MHz, DMSO-d6) δ 10.99 (s, 1H), 8.64 (t, J=6.4 Hz, 1H), 7.62 (d, J=8 Hz, 1H), 7.35-7.33 (m, 2H), 6.81 (d, J=8.4 Hz, 1H), 6.40-6.38 (m, 1H), 6.34-6.30 (m, 1H), 5.63 (t, J=6 Hz, 1H), 5.12 (dd, J=5.2, 13.2 Hz, 1H), 4.41-4.37 (m, 2H), 4.33 (s, 1H), 4.23-4.18 (m, 1H), 3.64 (d, J=6.4 Hz, 2H), 2.96-2.88 (m, 5H), 2.63-2.51 (m, 1H), 2.38-2.30 (m, 1H), 2.13 (s, 3H), 2.02-1.98 (m, 1H), 1.89-1.81 (m, 4H).

Example 22

Compound 22: 2-((3-chloro-4-morpholinophenyl)amino)-N-((2-(2,6-dioxopiperidin-3-yl)-1-oxoisoindolin-5-yl)methyl)acetamide

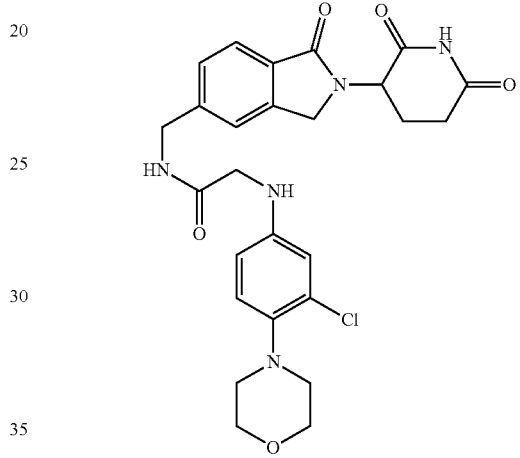

A mixture of 2-chloro-1-fluoro-4-nitrobenzene (5.0 g, 28.6 mmol), morpholine (3.7 g, 42.9 mmol), and K2CO3 (5.93 g, 42.9 mmol) in DMF (30 mL) was heated at 70° C. overnight. The mixture was filtered and concentrated. The residue was purified using silica gel eluting with PE/EA (2:1) to give 4-(2-chloro-4-nitrophenyl)morpholine (6.5 mg, 62% yield) as a solid. MS (ESI) m/z 243 [M+H]+.

To a solution of 4-(2-chloro-4-nitrophenyl)morpholine (1.0 g, 4.1 mmol) in AcOH (10 mL) was added iron powder (926 mg, 16.5 mmol). After 30 min, the mixture was filtered and concentrated. The residue was purified using silica gel eluting with PE/EA (1:1) to give 3-chloro-4-morpholinoaniline (760 mg, 86% yield) as an oil. MS (ESI) m/z=213 [M+H]+.

To a solution of 3-chloro-4-morpholinoaniline (760 mg, 3.58 mmol) in DMF (8 mL) was added K2CO3 (988 mg, 4.3 mmol) and tert-butyl 2-bromoacetate (839 mg, 4.3 mmol). After 1 h at 60° C., water was added, and the mixture was extracted with EA. The combined organic layers were washed with brine, dried over Na2SO4, filtered, and concentrated. The residue was purified using prep-TLC as previously described to give tert-butyl 2-((3-chloro-4-morpholinophenyl)amino)acetate (921 mg, 79% yield) as an oil. MS (ESI) m/z=327 [M+H]+.

To a solution of tert-butyl 2-((3-chloro-4-morpholinophenyl)amino)acetate (500 mg, 1.53 mmol) in DCM (5 mL) was added TFA (2 mL). After 2 h, the solution was concentrated to give 2-((3-chloro-4-morpholinophenyl)amino)acetic acid (350 mg, crude) which was used in the next step without purification.

To a solution of tert-butyl ((2-(2,6-dioxopiperidin-3-yl)-1-oxoisoindolin-5-yl) methyl)carbamate (100 mg, 0.27 mmol) in DCM (5 mL) was added TFA (2 mL). After 2 h, the mixture was concentrated and dissolved in DCM. TEA (136 mg, 1.36 mmol) and 2-((3-chloro-4-morpholinophenyl) amino)acetic acid (154 mg, 0.41 mmol) were added. The mixture was cooled to 0° C. then T3P (258 mg, 0.81 mmol, ≥50 wt. % in EA) was added dropwise. After 30 m at 0° C., the mixture was washed with water and concentrated. The residue was purified using prep-HPLC as previously described to afford Compound 22 (37 mg, 25% yield) as a solid. MS (ESI) m/z 526 [M+H]$^+$. $^1$H NMR (400 MHz, DMSO-d$_6$) δ 11.00 (s, 1H), 8.56 (t, J=6.0 Hz, 1H), 7.64 (d, J=7.6 Hz, 1H), 7.39 (s, 1H), 7.35 (d, J=8.0 Hz, 1H), 6.99 (d, J=9.2 Hz, 1H), 6.62 (d, J=2.4 Hz, 1H), 6.51 (dd, J=2.8, 8.8 Hz, 1H), 6.13 (t, J=6.0 Hz, 1H), 5.11 (dd, J=4.8, 13.2 Hz, 1H), 4.41-4.23 (m, 4H), 3.70-3.69 (m, 6H), 2.97-2.88 (m, 1H), 2.82-2.79 (m, 4H), 2.63-2.58 (m, 1H), 2.43-2.32 (m, 1H), 2.02-1.91 (m, 1H).

Example 23

Compound 23: N-((2-(2,6-dioxopiperidin-3-yl)-1-oxoisoindolin-5-yl)methyl)-2-((3-methyl-4-morpholinophenyl)amino)acetamide

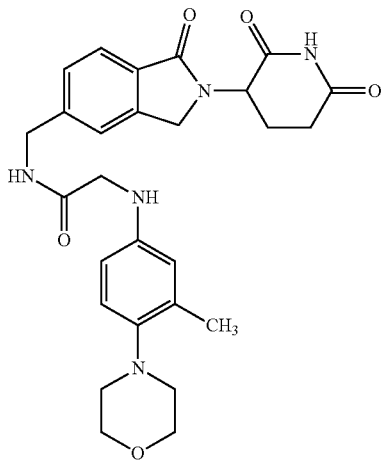 [SMILES: Cc1cc(NCC(=O)NCc2ccc3c(c2)CN(C2CCC(=O)NC2=O)C3=O)ccc1N1CCOCC1]

A mixture of 3-methyl-4-morpholinoaniline (500 mg, 2.6 mmol), tert-butyl 2-bromoacetate (431 mg, 3.1 mmol), and K$_2$CO$_3$ (718 mg, 5.2 mmol) in acetone (10 mL) was heated at reflux overnight. After filtration and concentration, the residue was purified using silica gel eluting with PE/EA (2:1) to give tert-butyl 2-((3-methyl-4-morpholinophenyl) amino)acetate (461 mg, 58% yield) as an oil. MS (ESI) m/z 307 [M+H]$^+$.

To a solution of tert-butyl 2-((3-methyl-4-morpholinophenyl)amino)-acetate (461 mg, 1.50 mmol) in DCM (5 mL) was added TFA (2 mL). After 2 h, the solution was concentrated to give 2-((3-methyl-4-morpholinophenyl)amino)acetic acid (301 mg, crude) which was used in the next step without purification.

To a solution of tert-butyl ((2-(2,6-dioxopiperidin-3-yl)-1-oxoisoindolin-5-yl) methyl)carbamate (100 mg, 0.27 mmol) in DCM (5 mL) was added TFA (2 mL). After 2 h, the mixture was concentrated. The residue was dissolved in DCM (5 mL), and 2-((3-methyl-4-morpholinophenyl) amino)acetic acid (154 mg, 0.41 mmol) and TEA (136 mg, 1.36 mmol) were added. The mixture was cooled to 0° C., then T3P (258 mg, 0.81 mmol, ≥50 wt. % in EA) was added dropwise. After 30 m at 0° C., the mixture was washed with water and concentrated. The residue was purified using prep-HPLC as previously described to afford Compound 23 (32 mg, 23% yield) as a solid. MS (ESI) m/z 506 [M+H]$^+$. $^1$H NMR (400 MHz, DMSO-d$_6$) δ 11.00 (s, 1H), 8.48 (t, J=6.0 Hz, 1H), 7.62 (d, J=7.6 Hz, 1H), 7.38 (s, 1H), 7.35 (d, J=8.0 Hz, 1H), 6.87 (d, J=8.0 Hz, 1H), 6.40 (s, 1H), 6.36 (dd, J=2.4, 8.0 Hz, 1H), 5.76 (t, J=6.0 Hz, 1H), 5.11 (dd, J=5.6, 13.6 Hz, 1H), 4.41-4.22 (m, 4H), 3.69-3.64 (m, 6H) 2.93-2.87 (m, 1H), 2.70-2.68 (m, 4H), 2.62-2.58 (m, 1H), 2.42-2.31 (m, 1H), 2.15 (s, 3H), 2.02-1.97 (m, 1H).

Example 24

Compound 24: N-((2-(2,6-dioxopiperidin-3-yl)-1-oxoisoindolin-5-yl)methyl)-2-((4-methyl-3-(pyrrolidin-1-yl)phenyl)amino)acetamide

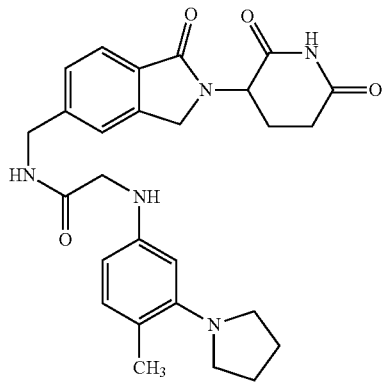 [SMILES: Cc1ccc(NCC(=O)NCc2ccc3c(c2)CN(C2CCC(=O)NC2=O)C3=O)cc1N1CCCC1]

To a solution of 2-fluoro-1-methyl-4-nitrobenzene (5.0 g, 32.3 mmol) in pyrrolidine (40 mL) was added K$_2$CO$_3$ (4.45 g, 32.3 mmol). The mixture was stirred in a sealed tube at 130° C. overnight. After concentration, the residue was diluted with water and extracted with EA. The combined organic layers were concentrated, and the residue was purified using silica gel eluting with PE/EA (2:1) to give 1-(2-methyl-5-nitrophenyl)-pyrrolidine (5.33 g, crude) which was used in the next step without purification.

To a solution of 1-(2-methyl-5-nitrophenyl)pyrrolidine (3.0 g, 14.6 mmol) in MeOH (30 ml) was added Pd/C (300 mg). The mixture was degassed and purged with H$_2$. After stirring overnight, the mixture was filtered and concentrated to give 4-methyl-3-(pyrrolidin-1-yl)aniline (580 mg, 22% yield).

To a solution of 4-methyl-3-(pyrrolidin-1-yl)aniline (176 mg, 1.0 mmol) and tert-butyl 2-bromoacetate (195 mg, 1.0 mmol) in acetone (10 mL) was added KI (332 mg, 2.0 mmol) and K$_2$CO$_3$ (276 mg, 2.0 mmol). The mixture was stirred at 60° C. under N$_2$ overnight, then filtered and concentrated. The residue was purified using silica gel eluting with PE/EA (2:1) to give tert-butyl 2-((4-methyl-3-(pyrrolidin-1-yl)phenyl)amino)acetate (206 mg, 71% yield).

To a solution of tert-butyl 2-((4-methyl-3-(pyrrolidin-1-yl)phenyl)amino)acetate (206 mg, 0.71 mmol) in DCM (4 ml) was added TFA (1 ml). The mixture was stirred overnight and concentrated to give crude 2-((4-methyl-3-(pyrrolidin-1-yl)phenyl)amino)acetic acid (101 mg, crude).

To a solution of tert-butyl ((2-(2,6-dioxopiperidin-3-yl)-1-oxoisoindolin-5-yl) methyl)carbamate (100 mg, 0.27 mmol) in DCM (4 mL) was added TFA (1 ml). After 1 h, the mixture was concentrated. The residue was dissolved in DCM (10 mL), and TEA (138 mg, 1.35 mmol) was added followed by a solution of 2-((4-methyl-3-(pyrrolidin-1-yl) phenyl)amino)acetic acid (63 mg, 0.27 mmol) in DCM (5 ml) dropwise. The mixture was cooled to 0° C. then T3P (430 mg, 1.35 mmol, ≥50 wt. % in EA) was added dropwise. After 4 h at RT, the mixture was washed with water and concentrated. The residue was purified using prep-HPLC as previously described to afford Compound 24 (20 mg, 15% yield) as a solid. MS (ESI) m/z=490 [M+H]$^+$. $^1$H NMR (400 MHz, DMSO-d$_6$) δ 11.06 (s, 1H), 8.52-8.51 (m, 1H), 7.68 (d, J=8 HZ, 1H), 7.43-7.41 (m, 1H), 8.85 (d, J=8 Hz, 1H), 6.17-6.16 (m, 1H), 6.08 (dd, J=8.0 Hz, 2.4 HZ, 1H), 5.78 (s, J=6 Hz, 1H), 5.168 (dd, J=13.6 Hz, 5.2 Hz, 1H), 4.46-4.32 (m, 2H), 4.40-4.27 (m, 2H), 3.71 (d, J=5.6 Hz, 2H), 3.42-3.40 (m, 1H), 3.05-2.98 (m, 4H), 2.97-2.93 (m, 1H), 2.74-2.65 (m, 1H), 2.49-2.38 (m, 1H), 2.17 (s, 3H), 2.09-2.05 (m, 1H), 1.86 (s, 4H).

Example 25

Compound 25: 2-((4-(dimethylamino)-3-methylphenyl)amino)-N-((2-(2,6-dioxopiperidin-3-yl)-1-oxoisoindolin-5-yl)methyl)acetamide

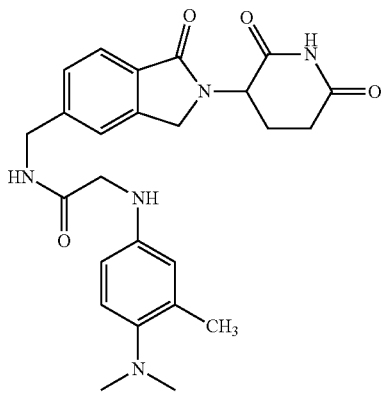 [SMILES: Cc1cc(NCC(=O)NCc2ccc3c(c2)CN(C2CCC(=O)NC2=O)C3=O)ccc1N(C)C]

To a solution of N$^1$,N$^1$,2-trimethylbenzene-1,4-diamine (500 mg, 3.33 mmol) in acetone (8 mL) was added K$_2$CO$_3$ (919 mg, 6.66 mmol) and tert-butyl 2-bromoacetate (780 mg, 4 mmol). After 1 h at 60° C., the mixture was diluted with water and extracted with EA. The combined organic layers were washed with brine, dried over Na$_2$SO$_4$, filtered, and concentrated. The residue was purified using prep-TLC as previously described to give tert-butyl 2-((3-chloro-4-morpholinophenyl)amino)acetate (748 mg, 85% yield) as a solid. MS (ESI) m/z=265 [M+H]$^+$.

To a solution of tert-butyl 2-((3-chloro-4-morpholinophenyl)amino)acetate (748 mg, 2.83 mmol) in DCM (5 mL) was added TFA (2 mL). After 2 h, the solution was concentrated to give 2-((4-(dimethylamino)-3-methylphenyl)amino)acetic acid (348 mg, crude) which was used in the next step without purification. MS (ESI) m/z=209 [M+H]$^+$.

To a solution of tert-butyl ((2-(2,6-dioxopiperidin-3-yl)-1-oxoisoindolin-5-yl)methyl)carbamate (100 mg, 0.27 mmol) in DCM (5 mL) was added TFA (2 mL). After 2 h at RT, the mixture was concentrated and dissolved in DCM (5 mL). 2-((4-(Dimethylamino)-3-methylphenyl)amino)acetic acid (84 mg, 0.41 mmol) and TEA (136 mg, 1.35 mmol) were added. The mixture was cooled to 0° C. then T3P (258 mg, 0.81 mmol, ≥50 wt. % in EA) was added dropwise. After 30 m at 0° C. then 2 h at RT, the mixture was concentrated, and the residue was purified using prep-HPLC as previously described to afford Compound 25 (30.1 mg, 48.5%) as a solid. MS (ESI) m/z 464 [M+H]$^+$. $^1$H NMR (400 MHz, DMSO-d$_6$) δ 10.98 (s, 1H), 8.46 (t, J=6.0 Hz, 1H), 7.62 (d, J=8.0 Hz, 1H), 7.39 (s, 1H), 7.35 (d, J=8.0 Hz, 1H), 6.87 (d, J=8.4 Hz, 1H), 6.38-6.34 (m, 2H), 5.68 (t, J=6.0 Hz, 1H), 5.10 (dd, J=5.2, 13.2 Hz, 1H), 4.41-4.23 (m, 4H), 3.64 (d, J=6.0 Hz, 2H), 2.96-2.87 (m, 1H), 2.67-2.57 (m, 1H), 2.39-2.33 (m, 1H), 2.15 (s, 3H), 2.02-1.97 (m, 1H).

Example 26

Compound 26: 2-((4-chloro-3-((dimethylamino) methyl)phenyl)amino)-N-((2-(2,6-dioxopiperidin-3-yl)-1-oxoisoindolin-5-yl)methyl)acetamide

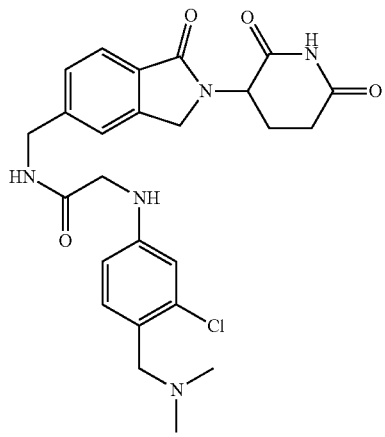 [SMILES: CN(C)Cc1ccc(NCC(=O)NCc2ccc3c(c2)CN(C2CCC(=O)NC2=O)C3=O)cc1Cl]

To a solution of 2-chloro-4-nitrobenzoic acid (5.0 g, 24.8 mmol) in DMF (100 mL) was added dimethylamine (1.34 g, 29.8 mmol), HATU (1.32 g, 29.8 mmol) and DIEA (9.62 g, 74.4 mmol). After 16 h, the mixture was diluted with water and extracted with EA. The combined organic layers were concentrated, and the residue was purified using silica gel eluting with PE/EA (2:1) to give 2-chloro-N,N-dimethyl-4-nitrobenzamide (5.1 g, 90% yield) as a solid. MS (ESI) m/z 229.1 [M+H]$^+$.

To a solution of 2-chloro-N,N-dimethyl-4-nitrobenzamide (5.1 g, 22.3 mmol) in EtOH (100 mL) was added water (2 mL), Fe (4.98 g, 89.2 mmol) and HCl (2 mL). After 5 h at 60° C., the mixture was filtered and concentrated. The residue was diluted with water and extracted with EA then DCM. The combined organic layers were concentrated to give 4-amino-2-chloro-N,N-dimethylbenzamide (3.7 g, crude) as a solid which was used for the next step without purification. MS (ESI) m/z 199.1 [M+H]$^+$.

To a solution of 4-amino-2-chloro-N,N-dimethylbenzamide (3.7 g, 18.6 mmol) in THF (50 mL) at 0° C. was added LiAlH$_4$ (1.41 g, 37.3 mmol). After 4 h at 38° C., the mixture was cooled to 0° C., and water was added slowly, followed by EA and 2N aqueous NaOH (2 mL). After 5 m at RT, the mixture was filtered and concentrated. The residue was purified using silica gel eluting with PE/EA (1:1) to give 3-chloro-4-((dimethylamino)methyl)aniline (2.0 g, 58% yield) as an oil. MS (ESI) m/z 185.1 [M+H]$^+$.

To a solution of 3-chloro-4-((dimethylamino)methyl)aniline (600 mg, 3.25 mmol) in DCM (30 mL) at 15° C. was added ethyl 2-oxoacetate (1.33 g, 6.50 mmol) and NaBH(OAc)$_3$ (2.07 g, 9.75 mmol). After 16 h at 15° C., NaBH$_3$CN (612.5 mg, 9.75 mmol) was added. After 30 m, the mixture was diluted with water and extracted with DCM. The combined organic layers were concentrated, and the residue was purified using silica gel eluting with PE/EA (2:1) to give ethyl 2-((3-chloro-4-((dimethylamino)methyl)phenyl)-amino)acetate (600 mg, 68% yield) as an oil. MS (ESI) m/z 271.1 [M+H]$^+$.

To a solution of ethyl 2-((3-chloro-4-((dimethylamino)methyl)phenyl)-amino)acetate (600 mg, 2.22 mmol) in MeOH (10 mL) and water (2 mL) was added LiOH.H$_2$O (278.98 mg, 6.65 mmol). After 2 h, the mixture was concentrated. The residue was diluted with water and acidified with HCl (1N) to a pH of 6 to 7. The mixture was concentrated to give 2-((3-chloro-4-((dimethylamino)methyl)phenyl)amino)acetic acid (537 mg, crude) as a solid which was used in the next step without purification. MS (ESI) m/z 385.2[M+H]$^+$.

To a solution of tert-butyl ((2-(2,6-dioxopiperidin-3-yl)-1-oxoisoindolin-5-yl)methyl)carbamate (200 mg, 0.536 mmol) in DCM (10 mL) at 15° C. was added TFA (2 mL). After 1 h at 15° C., the mixture was concentrated to give 3-(5-(aminomethyl)-1-oxoisoindolin-2-yl)piperidine-2,6-dione (146 mg, crude) as a solid which was used in the next step without purification. MS (ESI) m/z 274.1[M+H]$^+$.

To a solution of 2-((3-chloro-4-((dimethylamino)methyl)phenyl)-amino)acetic acid (73.0 mg, 0.267 mmol) in DCM (20 mL) at 15° C. was added 3-(5-(aminomethyl)-1-oxoisoindolin-2-yl)piperidine-2,6-dione (64.8 mg, 0.267 mmol), TEA (81.1 mg, 0.801 mmol) and T3P (101 mg, 0.321 mmol, ≥50 wt. % in EA). After 30 m at 15° C., the mixture was diluted with water and extracted with DCM. The combined organic layers were concentrated, and the residue was purified using prep-HPLC as previously described to afford Compound 26 (14.1 mg, 11% yield) as a solid. MS (ESI) m/z 498.1 [M+H]$^+$. $^1$H NMR (400 MHz, DMSO-d$_6$) δ 10.98 (s, 1H), 9.40 (s, 1H), 8.64 (t, J=6 Hz, 1H), 7.66 (d, J=8 Hz, 1H), 7.45 (s, 1H), 7.38 (d, J=8 Hz, 1H), 7.32 (d, J=8.4 Hz, 1H), 6.74-6.67 (m, 2H), 6.62 (d, J=8.4 Hz, 1H), 5.11 (dd, J=13.2, 5.2 Hz, 1H), 4.43-4.39 (m, 2H), 4.30-4.23 (m, 4H), 3.79 (s, 2H), 2.92-2.87 (m, 1H), 2.73 (s, 6H), 2.63-2.58 (m, 1H), 2.42-2.36 (m, 1H), 2.02-1.98 (m, 1H).

Example 27

Biological Assays

Western Blot Analysis

MV-4-11 cells were grown in RPMI 1640 media supplemented with 10% fetal bovine serum, streptomycin and penicillin.

Cells were cultured at approximately 106 cells per mL and incubated in DMSO or the indicated compound for 6-8 hours. Whole cell extracts were prepared using RIPA buffer according to manufacturer's protocol (Pierce). Briefly, 3×106 cells were washed once in PBS, the cell pellets were resuspended in RIPA buffer and allowed to incubate for 15 minutes on ice. Cells debris was removed by centrifugation and the cleared whole cell lysates were transferred to new tubes for further analysis.

For Western blot analysis, whole cell protein extracts were separated on 4-12% SDS-polyacrylamide gels, transferred to nitrocellulose and probed with the indicated primary antibodies. Membranes were subsequently washed and probed with the appropriate IRDye secondary antibodies (LI-COR). The signal was detected using the Odyssey Imaging System (LI-COR).

The following antibodies were used in these studies: Anti-eRF3/GSPT1: Abcam, ab126090 (Cambridge, Mass.); Anti-Ikaros: Abcam, ab191394 (Cambridge, Mass.); Anti-CK1α: Abcam, ab108296 (Cambridge, Mass.); β-actin (8H10D10) mouse monoclonal antibody: Cell Signaling Technology, #3700 (Danvers, Mass.); IRDye 680RD Goat anti-rabbit antibody: LI-COR, 926-68071 (Lincoln, Nev.); IRDye 800CW Goat anti-mouse antibody: LI-COR, 926-32210 (Lincoln, Nev.).

IKAROS activity is shown in Table 1. CK-1α activity is shown in Table 2. GSPT1 activity is shown in Table 3. In each of Tables 1-3, the % degradation values are reported as "A", "B", "C", or "D." "A" represents a % degradation value of less than 25% (value <25%); "B" represents a % degradation value of equal to or more than 25% and less than 50% (25%≤value <50%); "C" represents a % degradation value of equal to or more than 50% and less than 75% (50%≤value <75%); and "D" represents a % degradation value of equal to or more than 75% (value ≥75%).

TABLE 1

Activity of compounds in IKAROS degradation assay. Compounds tested at 1 μM.

| Compound No. | IKAROS % Degradation at 1 μM |
|---|---|
| 1 | D |
| 2 | D |
| 4 | B |
| 5 | D |
| 10 | A |
| 11 | B |
| 14 | D |
| 17 | C |
| 19 | B |
| 20 | B |
| 21 | C |
| 23 | C |
| 24 | D |

TABLE 2

Activity of compounds in CK1α degradation assay. Compounds tested at 1 μM.

| Compound No. | CK1α % Degradation at 1 μM |
|---|---|
| 1 | B |
| 5 | D |
| 10 | B |
| 14 | C |
| 17 | C |
| 18 | B |
| 20 | B |
| 21 | A |
| 24 | B |
| 25 | B |
| 26 | C |

TABLE 3

Activity of compounds in GSPT1 degradation assay. Compounds tested at 1 μM.

| Compound No. | GSPT1 % Degradation at 1 μM |
|---|---|
| 1 | D |
| 2 | C |
| 4 | B |
| 10 | D |
| 11 | B |
| 12 | C |
| 14 | C |
| 16 | B |
| 17 | D |
| 18 | D |
| 19 | D |
| 20 | B |
| 21 | C |
| 23 | B |
| 24 | D |
| 25 | C |
| 26 | C |

In addition, the comparative study between Compound 1 and reference Compound A (structure shown below) results showed that Compound 1 reduced levels of GSPT1 by 92% at 0.1 μM and by 93% at 1 μM. In contrast, Compound A reduced levels of GSPT1 by 82% at 0.1 μM and 98% at 1 μM.

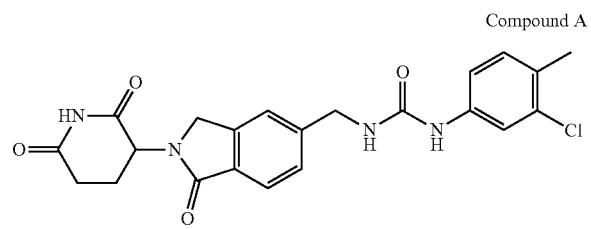 [SMILES: Cc1ccc(NC(=O)NCc2ccc3c(c2)CN(C2CCC(=O)NC2=O)C3=O)cc1Cl]

Compound A

Cell-Based Assay

Either frozen primary blood mononuclear cells (PBMCs) or frozen CD14+ mobilized peripheral blood monocytes were purchased from AllCells (PB003F, Normal Peripheral Blood MNC (Alameda, Caslif.)). Cells were quick thawed, washed 1-time with RPMI-1640 (10% FBS/1% Pen-Strep) and plated in 96 well plates at 200,000 cells per well. Cells were pretreated with DMSO only or with the indicated compound for 1 h and then induced with 100 ng/mL lipopolysaccharide (LPS) for 18-24 h. The supernatant was analyzed for IL-1β, IL-6, and TNFα, using Meso Scale assay according to manufacturer's protocol. The negative control wells were treated with DMSO.

For the IL-2 analysis, 96 well plates were precoated with 1 μg/mL anti-human CD3 antibody (OKT3, eBioscience Inc., San Diego, Calif.). After washing with PBS, the indicated compound was added (50 μL/well) followed by PBMCs diluted at 3-4 million cells/mL (150 μL/well). Plates were incubated for 24 h and the supernatants collected for Mesoscale IL-2 analysis. IL-2 activity is measured as fold difference from the DMSO control.

IL-1β activity is shown in Table 4. IL-6 activity is shown in Table 5. TNFα activity is shown in Table 6. IL-2 activity is shown in Table 7.

In each of Tables 4-6, the % inhibition values are reported as "A", "B", "C", or "D." "A" represents a % inhibition value of less than 30% (value <30%); "B" represents a % inhibition value of equal to or more than 30% and less than 50% (30%≤value <50%); "C" represents a % inhibition value of equal to or more than 50% and less than 75% (50%≤value <75%); and "D" represents a % inhibition value of equal or more than 75% (value ≥75%).

In Table 7, the fold-change values are reported as "A", "B", "C", or "D". "A" represents a fold-change value of equal to or less than 1 (value ≤1); "B" represents a fold-change value of more than 1 and equal to or less than 2 (1<value ≤2); "C" represents a fold-change value of more than 2 and equal to or less than 3 (2<value ≤3); and "D" represents a fold-change value of more than 3 (value >3).

TABLE 4

Activity of compounds in IL-1β inhibition assay. Compounds tested at 1 μM.

| Compound No. | IL-1β % Inhibition at 1 μM |
|---|---|
| 2 | D |
| 4 | C |
| 5 | D |
| 6 | A |
| 7 | D |
| 8 | D |
| 9 | C |
| 11 | B |
| 12 | A |
| 14 | D |
| 18 | B |
| 20 | A |
| 21 | A |
| 22 | C |
| 23 | B |
| 25 | A |

TABLE 5

Activity of compounds in IL-6 inhibition assay. Compounds tested at 1 μM.

| Compound No. | IL-6 % Inhibition at 1 μM |
|---|---|
| 513 | C |
| 541 | C |
| 688 | B |
| 576 | D |
| 996 | B |

TABLE 6

Activity of compounds in TNF-α inhibition assay. Compounds tested at 1 μM.

| Compound No. | TNF-α % Inhibition at 1 μM |
|---|---|
| 2 | C |
| 4 | C |
| 5 | D |
| 6 | A |
| 7 | D |
| 8 | D |
| 9 | C |
| 11 | B |
| 12 | A |
| 14 | C |

TABLE 6-continued

Activity of compounds in TNF-α inhibition assay. Compounds tested at 1 μM.

| Compound No. | TNF-α % Inhibition at 1 μM |
|---|---|
| 18 | B |
| 19 | B |
| 20 | B |
| 21 | B |
| 22 | C |
| 23 | B |
| 25 | B |

TABLE 7

Activity of compounds in IL-2 fold-change assay. Compounds tested at 1 μM.

| Compound No | IL-2 Fold-Change at 1 μM |
|---|---|
| 2 | B |
| 4 | C |
| 5 | D |
| 7 | C |
| 8 | B |
| 9 | B |
| 11 | B |
| 12 | B |
| 14 | C |
| 15 | B |
| 18 | A |
| 19 | A |
| 21 | B |
| 22 | C |
| 23 | B |
| 25 | B |

Cell Viability Assay

MOLM-13 cells were cultured in RPMI 1640 media supplemented with 10% fetal bovine serum, streptomycin and penicillin, and were plated in white walled 96-well plates at 2500 cells/well. Cells were incubated in DMSO (control) or the indicated compound for 3 days at 37° C. and 5% $CO_2$. Following the incubation period, 100 μL of CellTiterGlow2 (CTG2) reagent (CellTiter-Glo®2 Luminescent Cell Viability Assay, Promega (Madison, Wis.)) was added to each well. Following a 10 minutes incubation with shaking, luminescence was measured using the EnVision Multimode plate reader.

Antiproliferative activity of compounds in MOLM-13 cell viability assay is shown in Table 8. The MOLM-13 cell viability values, measured as percentages of the DMSO control, are reported in Table 8 as "A", "B", "C", or "D." "A" represents a % viability value of less than 40% (value <40%). "B" represents a % viability value of equal to or more than 40% and less than 60% (40%<value <60%). "C" represents a % viability value of equal to or more than 60% and less than 90% (60%≤value <90%). "D" represents a % viability value of equal or more than 90% (value ≥90%). The results indicated that the compounds inhibited cancer cell viability, such as leukemia cell viability.

TABLE 8

Activity of compounds in MOLM-13 cell viability assays. Compounds tested at 1 μM.

| Compound No. | MOLM-13 Cell Viability % DMSO at 1 μM |
|---|---|
| 1 | D |
| 2 | D |
| 4 | D |
| 5 | A |
| 10 | D |
| 11 | A |
| 14 | B |
| 16 | C |
| 17 | C |
| 18 | D |
| 19 | C |
| 20 | D |
| 21 | A |
| 23 | B |
| 24 | D |

Comparative Study:

Molm-13 and MV-4-11 cells (both leukemia cell lines) were cultured in RPMI 1640 media supplemented with 10% fetal bovine serum, streptomycin and penicillin, and were plated in white walled 96-well plates at 20,000 cells/well. THLE-2 cells (T-antigen immortalized human liver epithelial cells) were cultured using BEGM Bullet kit (Lonza CC-3170) supplemented with 10% fetal bovine serum, streptomycin and penicillin, and were plated in white walled 96-well plates 5000 cells/well. NHLF (normal human lung fibroblast) cells were cultured in DMEM media supplemented with 10% fetal bovine serum, streptomycin and penicillin, and were plated in white walled 96-well plates at 5000 cells/well. Cells were incubated in DMSO (control) or the indicated compounds for 3 days at 37° C. and 5% $CO_2$. Following the incubation period, 100 μL of CellTiterGlow2 (CTG2) reagent (CellTiter-Glo®2 Luminescent Cell Viability Assay, Promega (Madison, Wis.)) was added to each well. Following a 10 minutes incubation with shaking, luminescence was measured using the Victor Wallac Luminometer or the Envision 2105 multimode plate reader.

Frozen primary blood mononuclear cells (PBMCs) were purchased from AllCells. Cells were quick thawed, washed with RPMI-1640/10% FBS/1% Penicillin/1% Streptomycin and plated in 96 well plates at 200,000 cells/well. Cells were pretreated with DMSO or the indicated compound for 1 hr and then induced with 100 ng/mL lipopolysaccharide (LPS) for 18-24 hr. Following the incubation period, 100 μL of CTG reagent was added to each well. Plates were incubated on the shaker at RT for 2 min. Following a 10 min incubation without shaking, luminescence was measured using the Envision 2105 multimode plate reader.

Compound 1 reduced cell viability in Molm-13 cells at an $IC_{50}$ concentration of 74.8 nM; in MV-4-11 cells at an $IC_{50}$ concentration of 19.6 nM; in THLE-2 cells at an $IC_{50}$ concentration >10,000 nM; in NHLF cells at an $IC_{50}$ concentration >10,000 nM; and in PBMCs at an $IC_{50}$ concentration >10,000 nM. In contrast, Compound A (structure shown above) reduced cell viability in Molm-13 cells at an $IC_{50}$ concentration of 0.65 nM; in MV-4-11 cells at an $IC_{50}$ concentration of 1.87 nM; in THLE-2 cells at an $IC_{50}$ concentration of 6.11 nM; in NHLF cells at an $IC_{50}$ concentration of 31.68 nM; and in PBMCs at an $IC_{50}$ concentration of 6.00 nM. Accordingly, in contrast to the generally cytotoxic Compound A, Compound 1 surprisingly selectively reduces cellular viability in cancer cells, while having no detectable effect on the viability of normal cells.

In addition, Compounds 16, 17 and 18 have also demonstrated reduced cell viability in MV-4-11 cells at an $IC_{50}$ concentration of over 2-fold, about 1-fold, or about 0.5-fold of the $IC_{50}$ concentration of Compound 1 respectively; in THLE-2 cells at an $IC_{50}$ concentration of over 3-fold, about 1.5-fold or about 1-fold of the $IC_{50}$ concentration of Compound 1 respectively. Thus, similar to Compound 1, these compounds also showed selectivity reduction of cancer cell viability while comparable or improved safety profiles in normal cells.

What is claimed is:

1. A compound of Formula (I):

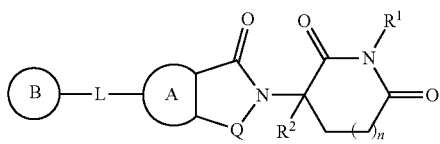

or a pharmaceutically acceptable salt thereof, wherein:
n is 0, 1, or 2;
$R^1$ is H, deuterium, $C_1$-$C_6$ alkyl,

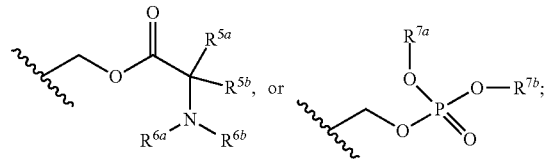

$R^2$ is H, deuterium, fluoro, or $C_1$-$C_6$ alkyl;
Q is C=O or $CR^{4a}R^{4b}$;
ring A is

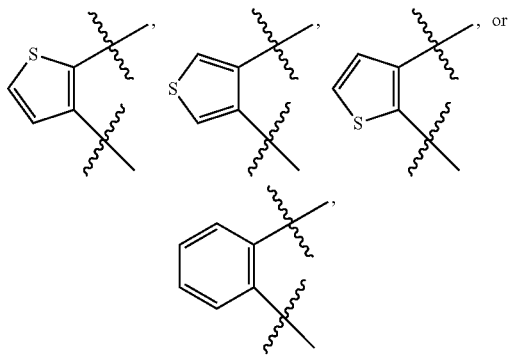

wherein ring A is optionally substituted with one or more $R^A$;
ring B is $C_6$-$C_{10}$ aryl, 5 to 10 membered heteroaryl, $C_3$ to $C_8$ carbocyclyl, or 3 to 10 membered heterocyclyl, each optionally substituted with one or more $R^B$;

L is

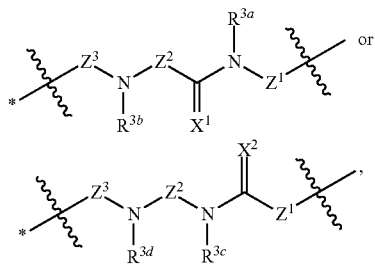

wherein the asterisk * indicates the point of connection to ring B;
$X^1$ and $X^2$ are each independently O, S, or NH;
each $Z^1$ is independently a bond or $(CR^{8a}R^{8b})_{m1}$—;
each $Z^2$ is independently $(CR^{8c}R^{8d})_{m2}$—;
each $Z^3$ is independently a bond or —$(CR^{8e}R^{8f})_{m3}$—;
$R^{3a}$, $R^{3b}$, $R^{3c}$, $R^{3d}$, $R^{4a}$, and $R^{4b}$ are each independently H, deuterium, or $C_1$-$C_6$ alkyl;
$R^{5a}$, $R^{5b}$, $R^{6a}$, $R^{6b}$, $R^{7a}$, and $R^{7b}$ are each independently H, optionally substituted $C_1$-$C_6$ alkyl, or optionally substituted $C_3$-$C_6$ cycloalkyl; or $R^{6a}$ and $R^{6b}$ together with the nitrogen atom to which they are attached form an optionally substituted 5 or 6 membered heterocyclyl;
each $R^{8a}$, $R^{8b}$, $R^{8c}$, $R^{8d}$, $R^{8e}$ and $R^{8f}$ is independently H, deuterium, halogen, hydroxy, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;
each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, amino($C_1$-$C_6$ alkyl), —(C=O)$NR^{10a}R^{10b}$, ($C_1$-$C_6$ alkoxy)$C_1$-$C_6$ alkyl, or optionally substituted $C_3$-$C_7$ cycloalkyl;
each $R^B$ is independently halogen, hydroxyl, cyano, nitro, acyl, optionally substituted $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, amino($C_1$-$C_6$ alkyl), —(C=O)$NR^{10a}R^{10b}$, ($C_1$-$C_6$ alkoxy)$C_1$-$C_6$ alkyl, optionally substituted $C_3$-$C_7$ cycloalkyl, optionally substituted $C_3$-$C_7$ cycloalkyl($C_1$-$C_6$ alkyl), optionally substituted $C_6$-$C_{10}$ aryl, optionally substituted $C_6$-$C_{10}$ aryl($C_1$-$C_6$ alkyl), optionally substituted 5 to 10 membered heteroaryl, optionally substituted 5 to 10 membered heteroaryl($C_1$-$C_6$ alkyl), optionally substituted heterocyclyl, or optionally substituted heterocyclyl($C_1$-$C_6$ alkyl);
each $R^{10a}$ and $R^{10b}$ is independently H or $C_1$-$C_6$ alkyl, or $R^{10a}$ and $R^{10b}$ together with the nitrogen atom to which they are attached form 5 or 6 membered heterocyclyl optionally substituted with one or more $R^9$;
each $R^9$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, optionally substituted amino, halogen, or cyano; or two geminal $R^9$ form oxo (=O); and
m1, m2, and m3 are each independently 1, 2, 3, 4, or 5.

2. The compound of claim 1, wherein the compound is a compound of also represented by Formula (Ia), (Ib), (Ic), (Id), (Ie) (If), (Ig), (Ih), or (Ii):

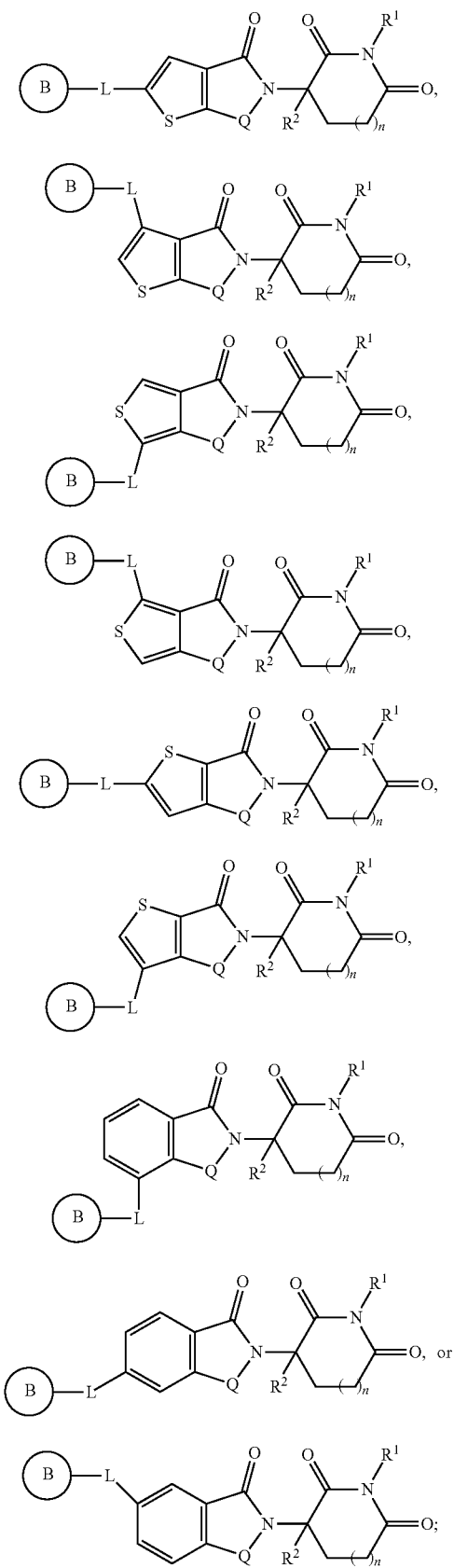

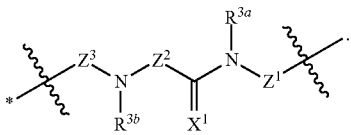

or a pharmaceutically acceptable salt thereof; wherein the phenyl moiety in Formula (Ig), (Ih) or (Ii) is optionally substituted with one or more $R^A$.

3. The compound of claim 1, wherein $R^1$ is H.
4. The compound of claim 3, wherein n is 1.
5. The compound of claim 4, wherein Q is $CH_2$.
6. The compound of claim 4, wherein Q is C(=O).
7. The compound of claim 1, wherein $R^2$ is H, deuterium, fluoro, or methyl.
8. The compound of claim 1, wherein L is 9. The compound of claim 8, wherein $X^1$ is O, and $R^{3a}$ and $R^{3b}$ are each H.
10. The compound of claim 8, wherein $Z^1$ and $Z^3$ are each a bond.
11. The compound of claim 8, wherein $Z^1$ is $(CR^{8a}R^{8b})_{m1}$— and $Z^3$ is —$(CR^{8e}R^{8f})_{m3}$—, or $Z^1$ is —$(CR^{8a}R^{8b})_{m1}$— and $Z^3$ is a bond, or $Z^1$ is a bond and $Z^3$ is —$(CR^{8e}R^{8f})_{m3}$—.
12. The compound of claim 11, wherein each $R^{8a}$ and $R^{8b}$ is H; and each $R^{8c}$, $R^{8d}$, $R^{8e}$ and $R^{8f}$ is independently H, deuterium, halogen or $C_1$ to $C_6$ alkyl.
13. The compound of claim 12, wherein each of $R^{8c}$, $R^{8d}$, $R^{8e}$ and $R^{8f}$ is H.
14. The compound of claim 12, wherein each of $R^{8e}$ and $R^{8f}$ is H, and at least one of $R^{8c}$ and $R^{8d}$ is halogen or $C_1$-$C_6$ alkyl.
15. The compound of claim 11, wherein m1, m2 and m3 are each independently 1 or 2.
16. The compound of claim 1, wherein ring B is phenyl, naphthyl, $C_4$-$C_6$ cycloalkyl, 4 to 6 membered heterocyclyl, or 5 to 6 membered heteroaryl, each optionally substituted with one, two, three or four $R^B$; and wherein each $R^B$ is independently halogen, hydroxyl, cyano, nitro, acyl, optionally substituted $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, amino($C_1$-$C_6$ alkyl), —(C=O)$NR^{10a}R^{10b}$, ($C_1$-$C_6$ alkoxy)$C_1$-$C_6$ alkyl, $C_3$-$C_7$ cycloalkyl optionally substituted with one or more $R^9$, $C_3$-$C_7$ cycloalkyl($C_1$-$C_6$ alkyl) optionally substituted with one or more $R^9$, $C_6$-$C_{10}$ aryl optionally substituted with one or more $R^9$, $C_6$-$C_{10}$ aryl($C_1$-$C_6$ alkyl) optionally substituted with one or more $R^9$, 5 or 6 membered heteroaryl optionally substituted with one or more $R^9$, 5 or 6 membered heteroaryl ($C_1$-$C_6$ alkyl) optionally substituted with one or more $R^9$, heterocyclyl optionally substituted with one or more $R^9$, or heterocyclyl($C_1$-$C_6$ alkyl) optionally substituted with one or more $R^9$.
17. The compound of claim 16, wherein ring-B is phenyl or pyridyl, each substituted with one, two, or three $R^B$.
18. The compound of claim 17, wherein each $R^B$ is independently chloro, fluoro, —$NH_2$, ($C_1$-$C_6$ alkyl)amino, amino($C_1$-$C_6$ alkyl), $C_1$-$C_6$ alkyl, $C_1$-$C_6$ alkoxy, $C_1$-$C_6$ haloalkyl, $C_1$-$C_6$ haloalkoxy, acyl, $C_3$-$C_7$ cycloalkyl, $C_3$-$C_7$ cycloalkyl($C_1$-$C_6$ alkyl), 4 to 6 membered heterocyclyl, N—($C_1$-$C_6$ alkyl)heterocyclyl, or heterocyclyl($C_1$-$C_6$ alkyl), wherein each of $C_3$-$C_7$ cycloalkyl, $C_3$-$C_7$ cycloalkyl($C_1$-$C_6$ alkyl), 4 to 6 membered heterocyclyl, and heterocyclyl($C_1$-$C_6$ alkyl) is optionally substituted with one or more $R^9$.
19. The compound of claim 18, wherein each $R^B$ is independently fluoro, chloro, methyl, ethyl, n-propyl, isopropyl, tert-butyl, trifluoromethyl, trifluoromethoxy, —NH(C$_1$-C$_4$ alkyl), —N(C$_1$-C$_4$ alkyl)$_2$, —(CH$_2$)$_{1-3}$—NH(C$_1$-C$_4$ alkyl), —(CH$_2$)$_{1-3}$—N(C$_1$-C$_4$ alkyl)$_2$

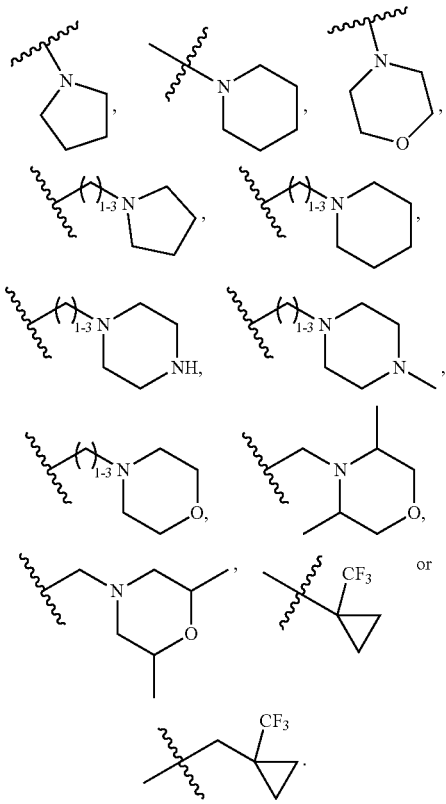

20. The compound of claim 17, wherein ring B is substituted with two R$^B$, and wherein one R$^B$ is C$_1$-C$_6$ alkyl or halogen, and the other R$^B$ is halogen, —NH(C$_1$-C$_4$ alkyl), —N(C$_1$-C$_4$ alkyl)$_2$, —(CH$_2$)—NH(C$_1$-C$_4$ alkyl), —(CH$_2$)—N(C$_1$-C$_4$ alkyl)$_2$,

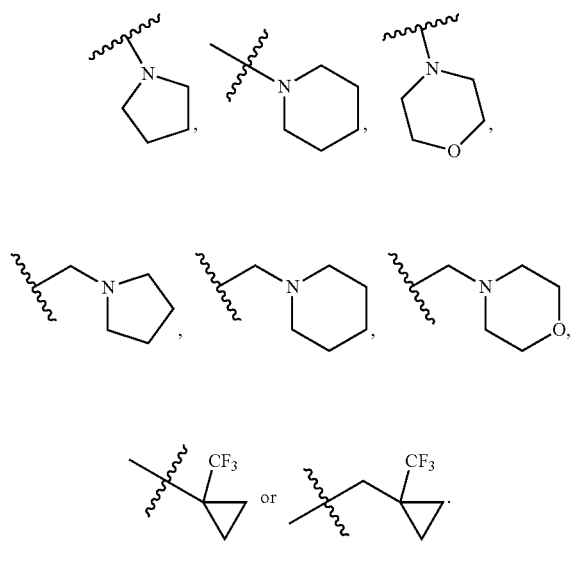

21. A compound selected from the group consisting of:

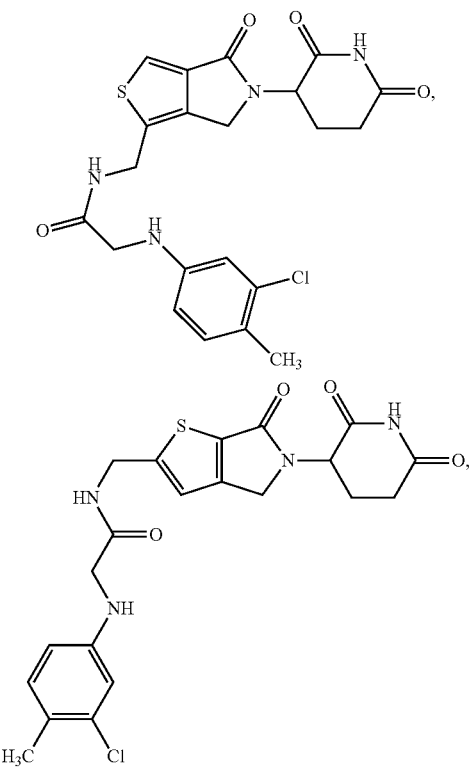

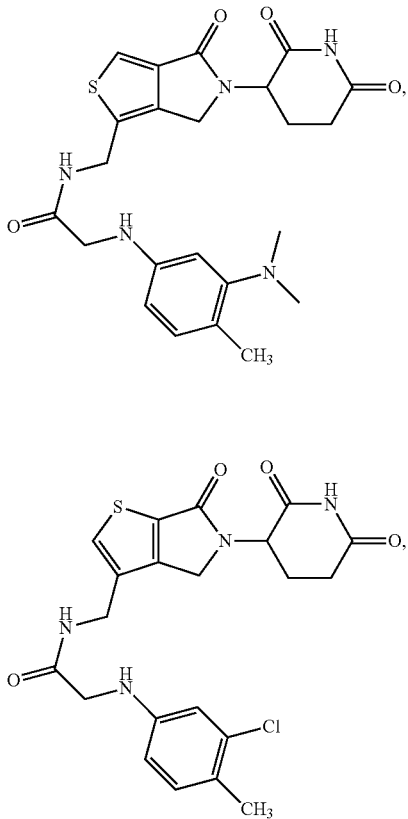

99
-continued
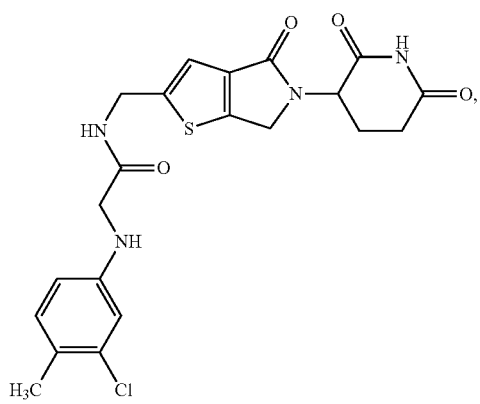
100
-continued
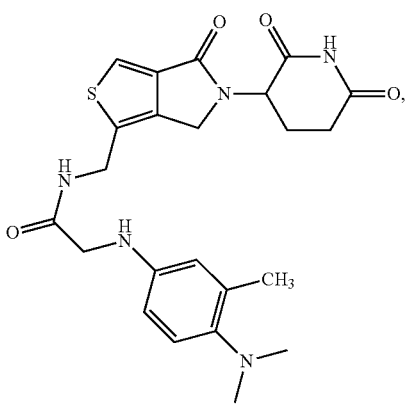
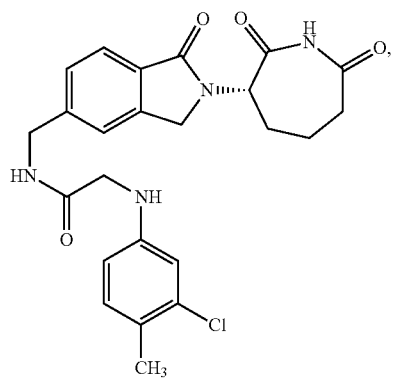
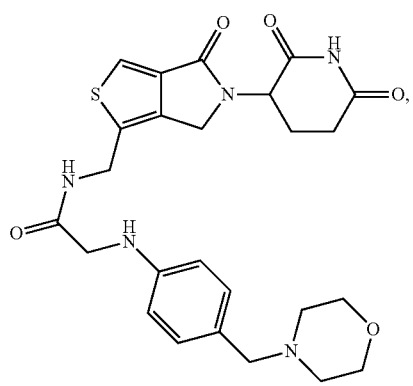

101 -continued

102 -continued

103
-continued
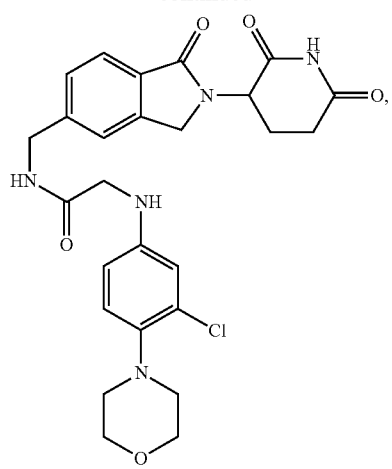
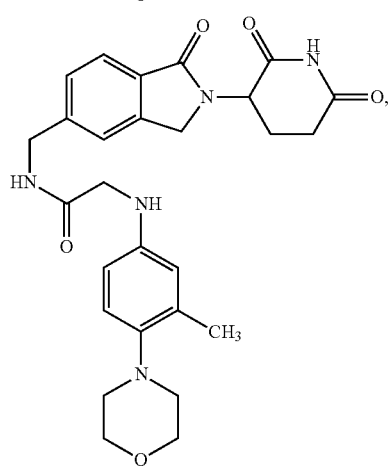
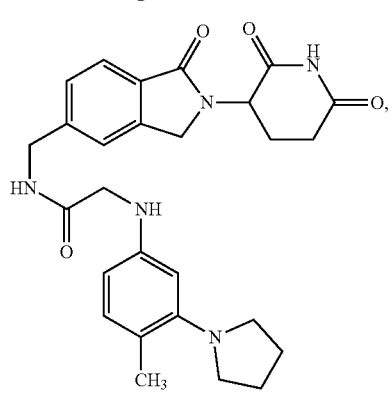
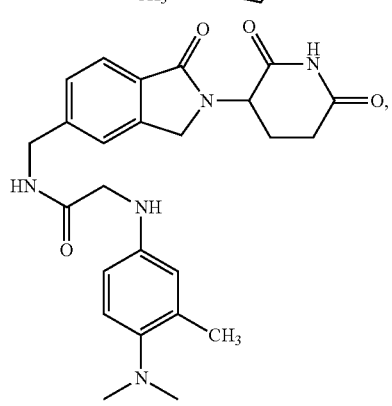
104
-continued
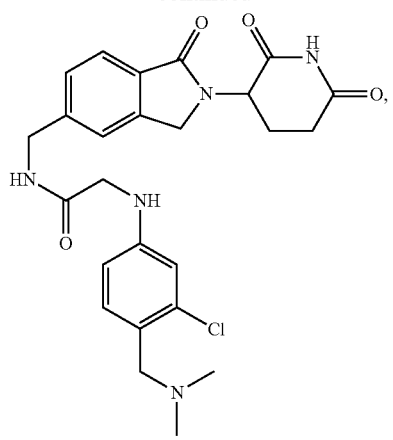
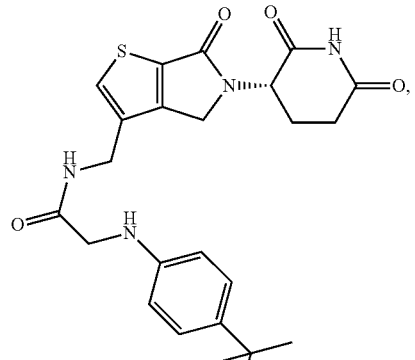
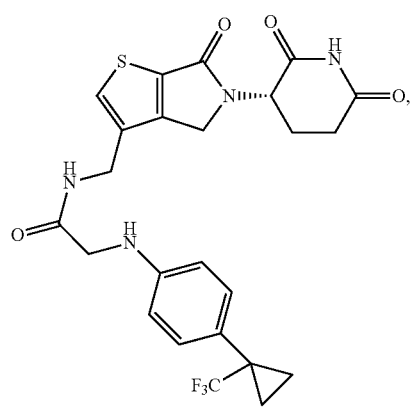
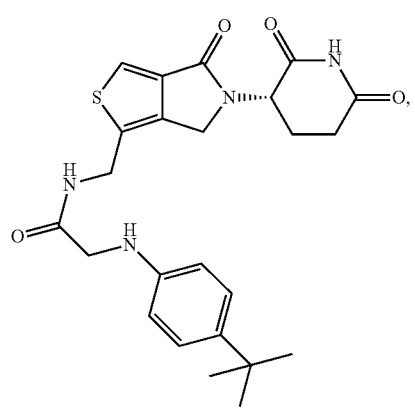

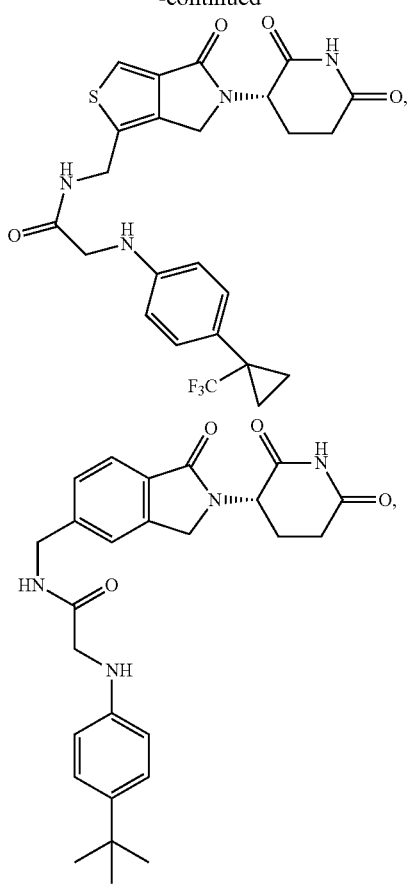

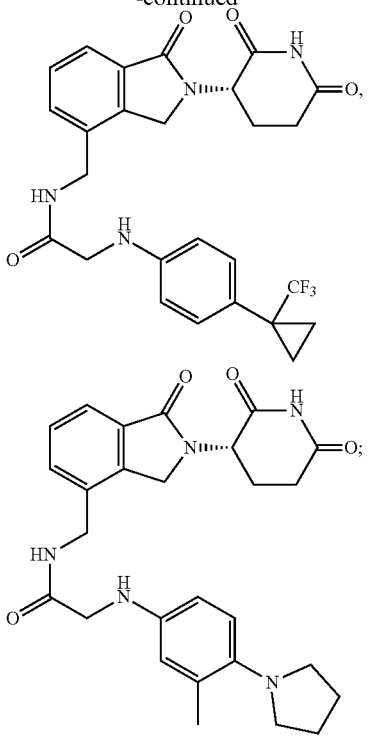

and pharmaceutically acceptable salts thereof.

22. A pharmaceutical composition, comprising a compound of claim 1, or a pharmaceutically acceptable salt thereof, and at least one pharmaceutically acceptable carrier or excipient.

23. The compound of claim 1, wherein the compound is a compound of Formula (Ig):

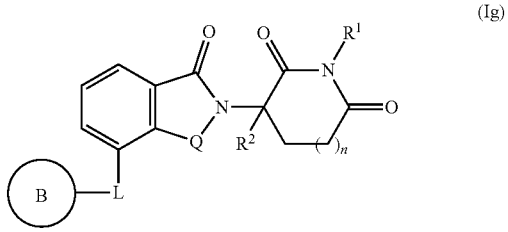

or a pharmaceutically acceptable salt thereof; wherein the phenyl moiety in Formula (Ig) is optionally substituted with one or more $R^A$.

24. The compound of claim 1, wherein the compound is a compound of Formula (Ig):

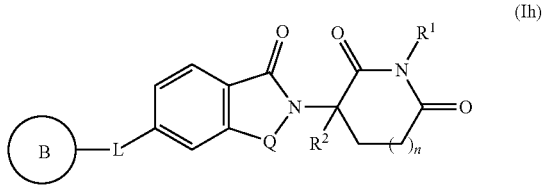

or a pharmaceutically acceptable salt thereof; and wherein the phenyl moiety in Formula (Ih) is optionally substituted with one or more $R^A$.

25. The compound of claim 1, wherein the compound is a compound of Formula (Ii):

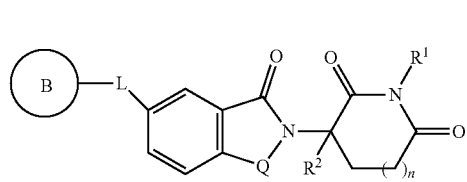

(Ii)

or a pharmaceutically acceptable salt thereof; and wherein the phenyl moiety in Formula (Ii) is optionally substituted with one or more $R^A$.

26. The compound of claim 21, wherein the compound is:

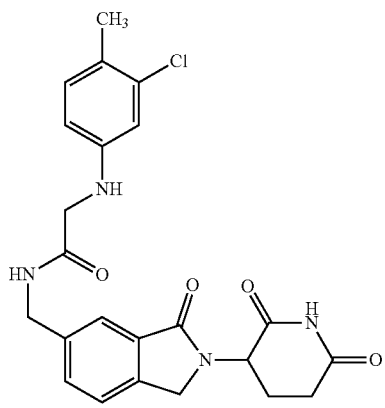 [SMILES: Cc1ccc(NCC(=O)NCc2ccc3c(c2)C(=O)N(C2CCC(=O)NC2=O)C3)cc1Cl]

or a pharmaceutically acceptable salt thereof.

27. The compound of claim 21, wherein the compound is:

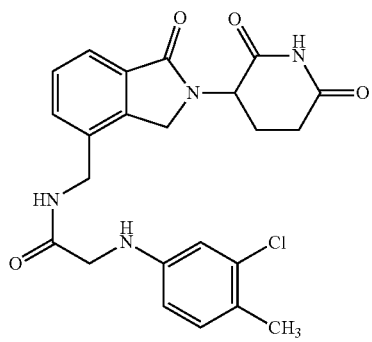 [SMILES: Cc1ccc(NCC(=O)NCc2cccc3c2CN(C2CCC(=O)NC2=O)C3=O)cc1Cl]

or a pharmaceutically acceptable salt thereof.

28. The compound of claim 21, wherein the compound is:

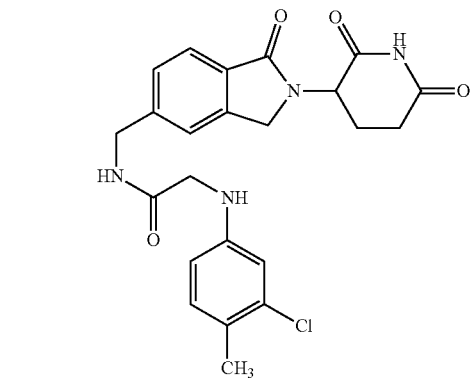

or a pharmaceutically acceptable salt thereof.

29. The compound of claim 21, wherein the compound is:

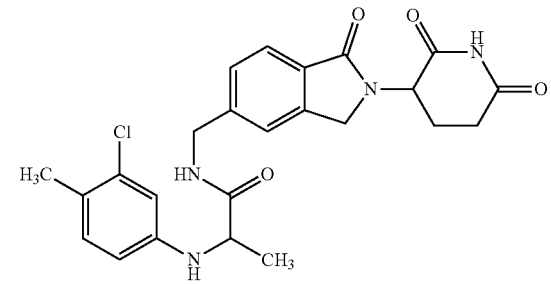 [SMILES: Cc1ccc(NC(C)C(=O)NCc2ccc3c(c2)CN(C2CCC(=O)NC2=O)C3=O)cc1Cl]

or a pharmaceutically acceptable salt thereof.

* * * * *